(12) United States Patent
Huh et al.

(10) Patent No.: US 11,008,546 B2
(45) Date of Patent: May 18, 2021

(54) SYSTEMS AND METHODS FOR IMMOBILIZING EXTRACELLULAR MATRIX MATERIAL ON ORGAN ON CHIP, MULTILAYER MICROFLUIDICS MICRODEVICES, AND THREE-DIMENSIONAL CELL CULTURE SYSTEMS

(71) Applicant: THE TRUSTEES OF THE UNIVERSITY OF PENNSYLVANIA, Philadelphia, PA (US)

(72) Inventors: Dongeun Huh, Villanova, PA (US); Mark Mondrinos, Philadelphia, PA (US); Cassidy Blundell, Cambridge, MA (US); Jeongyun Seo, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/748,066

(22) PCT Filed: Jul. 27, 2016

(86) PCT No.: PCT/US2016/044321
§ 371 (c)(1),
(2) Date: Jan. 26, 2018

(87) PCT Pub. No.: WO2017/019799
PCT Pub. Date: Feb. 2, 2017

(65) Prior Publication Data
US 2018/0223251 A1    Aug. 9, 2018

Related U.S. Application Data

(60) Provisional application No. 62/197,444, filed on Jul. 27, 2015, provisional application No. 62/348,036, filed on Jun. 9, 2016, provisional application No. 62/348,055, filed on Jun. 9, 2016.

(51) Int. Cl.
| | | |
|---|---|---|
| *C12N 5/00* | (2006.01) | |
| *A61L 27/22* | (2006.01) | |
| *A61L 27/18* | (2006.01) | |
| *A61L 27/38* | (2006.01) | |
| *C12M 3/00* | (2006.01) | |
| *C12M 1/00* | (2006.01) | |
| *C12M 1/12* | (2006.01) | |
| *A61L 27/52* | (2006.01) | |
| *C08L 83/04* | (2006.01) | |
| *A61L 27/36* | (2006.01) | |

(52) U.S. Cl.
CPC ............ *C12N 5/0068* (2013.01); *A61L 27/18* (2013.01); *A61L 27/22* (2013.01); *A61L 27/3633* (2013.01); *A61L 27/3804* (2013.01); *A61L 27/52* (2013.01); *C08L 83/04* (2013.01); *C12M 3/00* (2013.01); *C12M 21/08* (2013.01); *C12M 23/20* (2013.01); *C12M 25/14* (2013.01); *C12M 29/10* (2013.01); *C12N 5/0018* (2013.01); *C12N 5/0062* (2013.01); *C12N 2533/30* (2013.01); *C12N 2533/54* (2013.01); *C12N 2535/00* (2013.01); *C12N 2537/10* (2013.01)

(58) Field of Classification Search
None
See application file for complete search history.

(56) References Cited

U.S. PATENT DOCUMENTS

| | | | |
|---|---|---|---|
| 9,618,500 B2 * | 4/2017 | Giselbrecht | ........ G01N 33/5005 |
| 2004/0258571 A1 | 12/2004 | Lee et al. | |
| 2007/0092550 A1 | 4/2007 | Lui | |
| 2007/0224677 A1 | 9/2007 | Neumann | |
| 2010/0279268 A1 | 11/2010 | Neumann et al. | |
| 2011/0250585 A1 | 10/2011 | Ingber et al. | |
| 2012/0322097 A1 | 12/2012 | Charest et al. | |
| 2013/0309771 A1 | 11/2013 | Gevaert et al. | |
| 2013/0344529 A1 | 12/2013 | Giselbrecht et al. | |
| 2014/0093905 A1 | 4/2014 | Ingber et al. | |
| 2014/0147880 A1 | 5/2014 | Ingber et al. | |
| 2014/0158233 A1 | 6/2014 | Leslie et al. | |
| 2014/0335496 A1 | 11/2014 | Grego et al. | |
| 2014/0342445 A1 | 11/2014 | Ingber et al. | |
| 2014/0356849 A1 | 12/2014 | Wikswo et al. | |
| 2015/0087004 A1 | 3/2015 | Chen et al. | |

(Continued)

FOREIGN PATENT DOCUMENTS

| WO | WO 2014/127250 A1 | 8/2014 |
|---|---|---|
| WO | WO 2015/061907 A1 | 5/2015 |
| WO | WO 2015/138032 A2 | 9/2015 |

OTHER PUBLICATIONS www.nnerriann-webster.com/dictionary/tissue (accessed Feb. 24, 2020) (Year: 2020).*
Yum et al., Biotechnol. J., 9:16-27 (2014) (Year: 2014).*
Esch et al., Tiss. Eng. A, 17(23-24):2965-2971 (2011) (Year: 2011).*
Annab et al., Lab Chip, 13:3569-3577 (2013) (Year: 2013).*
Baker et al., Lab Chip, 13(16):3246-3252 (2013) (Year: 2013).*
Baranski et al., PNAS, 110(19):7586-7591 (2013) (Year: 2013).*
Bertassoni et al., Lab Chip, 14(13):2202-2211 (2014) (Year: 2014).*
Bischel et al., Biomater., 34(5):1471-1477 (2013) (Year: 2013).*
Choi et al., Bioprocess. Biosyst. Eng. (2013) (Year: 2013).*

(Continued)

*Primary Examiner* — Thomas J. Visone
(74) *Attorney, Agent, or Firm* — Baker Botts, L.L.P.

(57) ABSTRACT

The presently disclosed subject matter provides an approach to address the needs for microscale control in shaping the spacial geometry and microarchitecture of 3D collagen hydrogels. For example, the disclosed subject matter provides for compositions, methods, and systems employing N-sulfosuccinimidyl-6-(4'-azido-2'-nitro-phenylamino) hexanoate ("sulfo-SANPAH"), to prevent detachment of the hydrogel from the anchoring substrate due to cell-mediated contraction.

6 Claims, 41 Drawing Sheets

(56) References Cited

U.S. PATENT DOCUMENTS

2015/0104812 A1 4/2015 Grevesse et al.
2015/0329354 A1* 11/2015 Kato .................. B81C 1/00
                                                                427/271

OTHER PUBLICATIONS

Hammer et al., Tiss. Eng., C, 20(2):169-176 (2014) (Year: 2014).*
He et al., Mater. Sci. Eng. C, 59:53-60 (2016) (Year: 2016).*
Huh et al., Trends Cell Biol., 21(12):745-754 (2011) (Year: 2011).*
Jimenez-Torres et al., Adv. Healthc. Mater., 5(2):198-204 (2016) (Year: 2016).*
Kim et al., Lab Chip, 12:2165-2174 (2012) (Year: 2012).*
Liu et al., Int. J. Mol. Sci., 16:15997-16016 (2015) (Year: 2015).*
Park et al., Anal. Chem., 77:6571-6580 (2005) (Year: 2005).*
Ramadan et al, Lab Chip, 15:614-636 (2015) (Year: 2015).*
Stokol et al., ASME 9th Conf., ICNMM2011-58298 (2011) (Year: 2011).*
Yeon et al., Lab Chip, 12:2815-2822 (2012) (Year: 2012).*
U.S. Appl. No. 15/748,039, filed Jan. 26, 2018.
U.S. Appl. No. 15/748,087, filed Jan. 26, 2018.
Bhatia, et al., "Microfluidic organs-on-chips," Nature Biotechnology, 32(8):760-772 (2014).
Cagnin et al., "Overview of Micro- and Nano-Technology Tools for Stem Cell Applications: Micropatterned and Microelectronic Devices," Sensors, 12:15947-15982 (2012).
De Souza Carvalho et al., "Carrier interactions with the biological barriers of the lung: Advanced in vitro models and challenges for pulmonary drug delivery," Advanced Drug Delivery Reviews, 75:129-140 (2014).
Evans et al., "The role of material structure and mechanical properties in cell-matrix interactions," Journal of Materials Chemistry B, 2:2345-2356 (2014).
Golden et al., "Fabrication of microfluidic hydrogels using molded gelatin as a sacrificial element," Lab on a Chip, 7:720-725 (2007).
Huh et al., "Microfabrication of human organs-on-chips," Nature Protocols 8(11):2135-2157 (2013).
Huh et al., "Reconstituting Organ-Level Lung Functions on a Chip," Science, 328:1662-1668 (2010).
International Search Report dated Oct. 21, 2016 in International Application No. PCT/US2016/044321.
International Search Report dated Oct. 5, 2016 in International Application No. PCT/US2016/044313.
International Search Report dated Oct. 7, 2016 in International Application No. PCT/US16/44282.
Jorgensen et al., "Cigarette smoke induces endoplasmic reticulum stress and the unfolded protein response in normal and malignant human lung cells," BMC Cancer 8:229 (2008).
Kelsen et al., "Cigarette Smoke Induces an Unfolded Protein Response in the Human Lung: A Proteomic Approach," American Journal of Respiratory Cell and Molecular Biology 38:541-550 (2008).
Kenche et al., "Cigarette smoking affects oxidative protein folding in endoplasmic reticulum by modifying protein disulfide isomerase," FASEB J. 27:965-977 (2013).
Kramann et al., "Perivasculoar Gli1+ Progenitors Are Key Contributors to Injury-Induced Organ Fibrosis," Cell Stem Cell 16:51-66 (2015).
Neal et al., "Formation of elongated fascicle-inspired 3D tissues consisting of high-density, aligned cells using sacrificial outer molding," Lab Chip, 14:1907-1916 (2014).
Sakar et al., "Formation and optogenetic control of engineered 3D skeletal muscle bioactuators," Lab Chip, 12:4976-4985 (2012).
Wen et al., "Interplay of matrix stiffness and protein tethering in stem cell differentiation," Nature Materials, 13:979-987 (2014).
Wolz et al., "In vitro genotoxicity assay of sidestream smoke using a human bronchial epithelial cell line," Food and Chemical Toxicology, 40:845-850 (2002).
U.S. Appl. 15/748,087, Sep. 26, 2019 Non-Final Office Action.
Klein et. al., "An improved 3D tetraculture system mimicking the cellular organisation at the alveolar barrier to study the potential toxic effects of particles on the lung," Particle and Fibre Toxicology 10:31 (2013) available from: https://particleandfibretoxicology.biomedcentral.com/articles/10.1186/1743-8977-10-31.

* cited by examiner

Untreated

Day 1  Day 3  Day 5

Sulfo-SANPAH Treated

Day 1  Day 3  Day 5

FIG. 10B
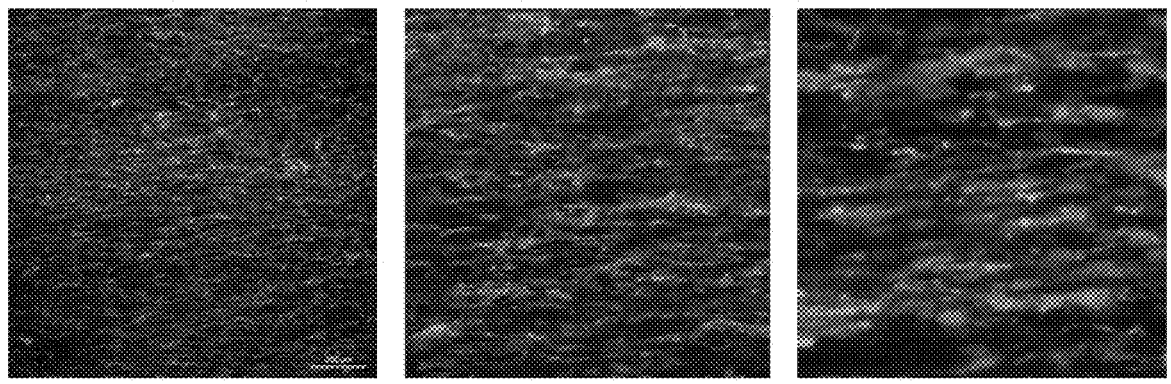
FIG. 11
|  | Fibronectin | | Nuclei | |
|---|---|---|---|---|
|  | Contracted | 2-node | Contracted | 2-node |
| Dominant Direction | 41.8 | 5.54 | 44.2 | 2.54 |
| Coherency | 0.035 | 0.613 | 0.012 | 0.395 |
FIG. 12A
Unpatterned/Contracted
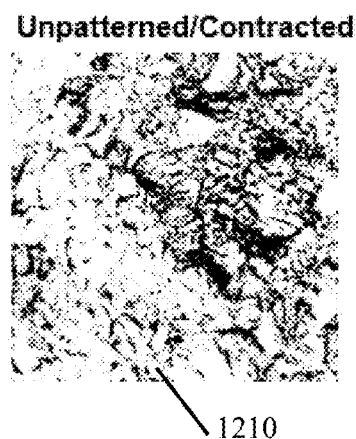
1210
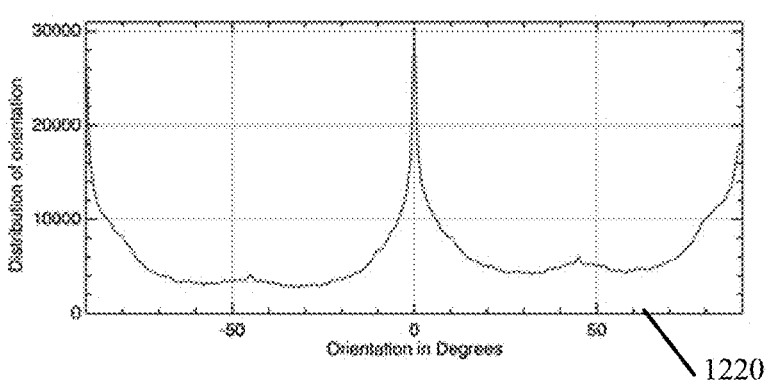
1220

FIG. 14A
FIG. 14B
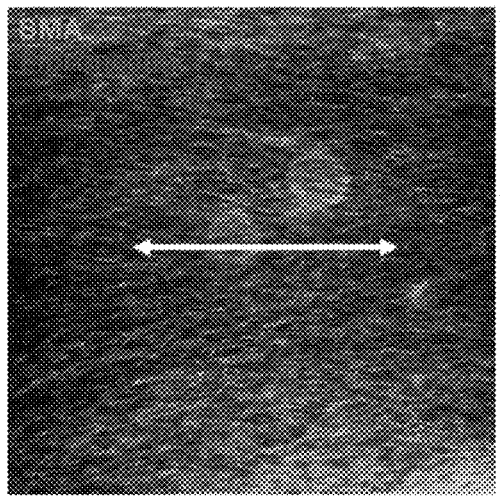
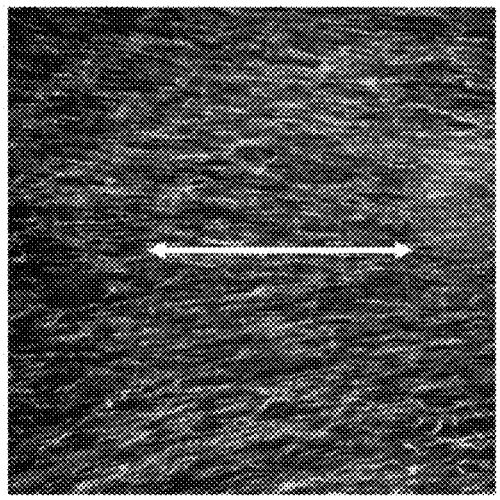
FIG. 15A
FIG. 15B
Un-patterned – 5d
Patterned – 5d
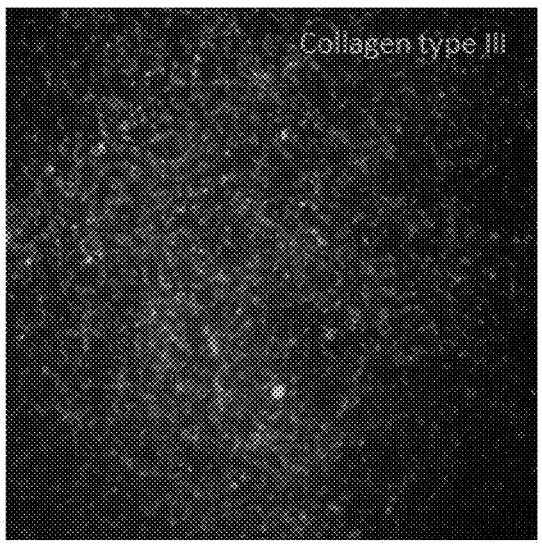
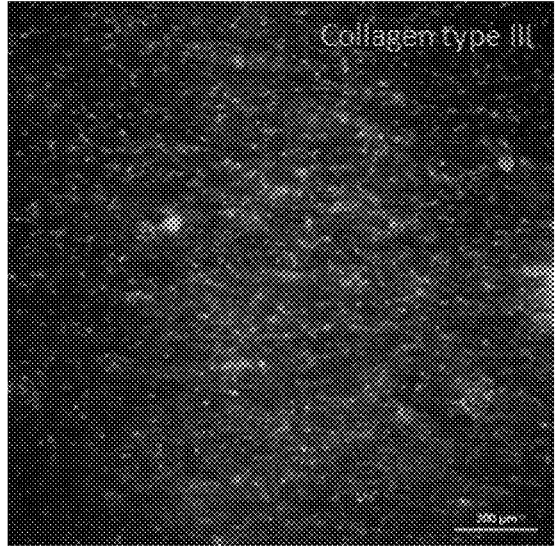
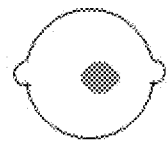
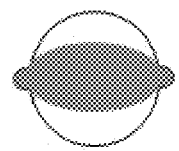

FIG. 15C
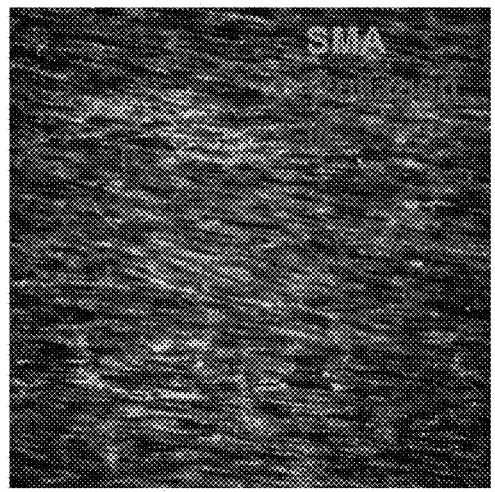
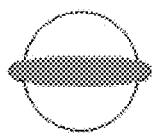
FIG. 16A
FIG. 16B
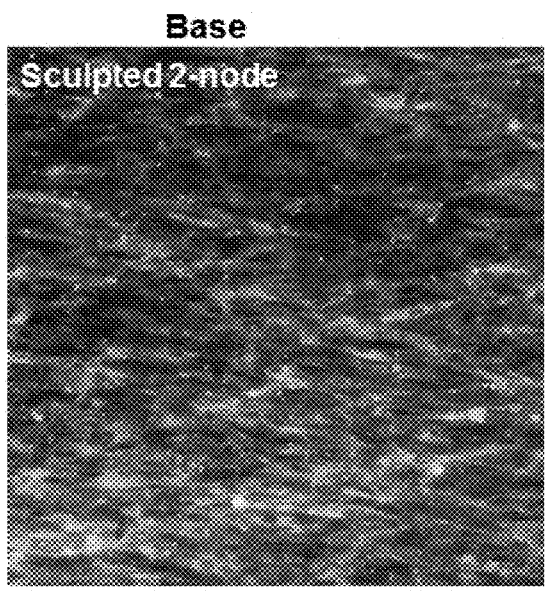
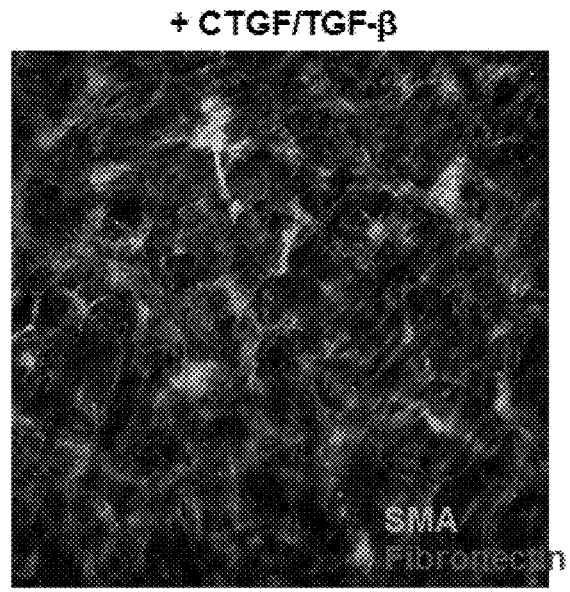

Center of construct

Near boundary

MSC 2-node 6 days

Center of construct

Near boundary

MSC 2-node 11 days

- Cultured for 14 days
- Nuclei / F actin / α-actinin
- Scale bar = 100 μm

ROI : 1270 x 1270 x 73 μm

FIG. 20B
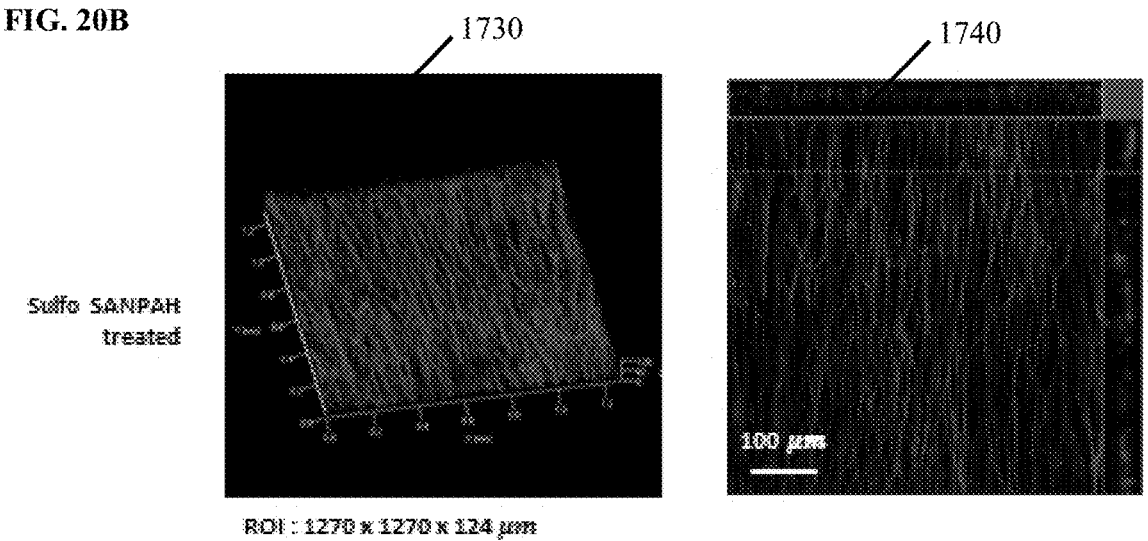
FIG. 21A  FIG. 21B
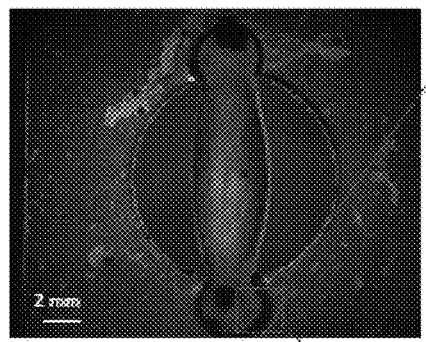
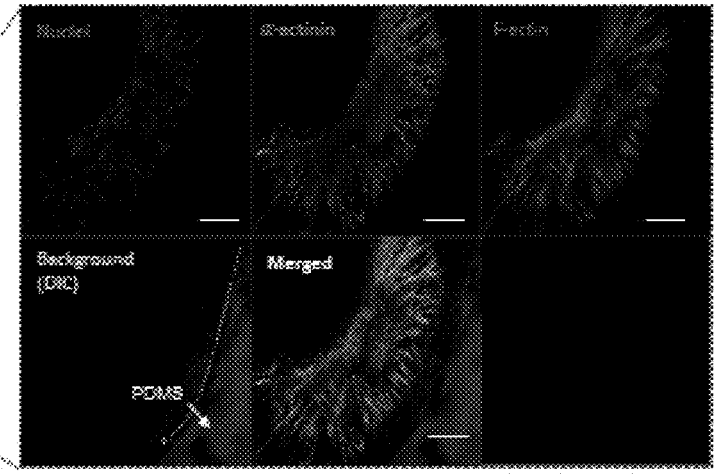

FIG. 22
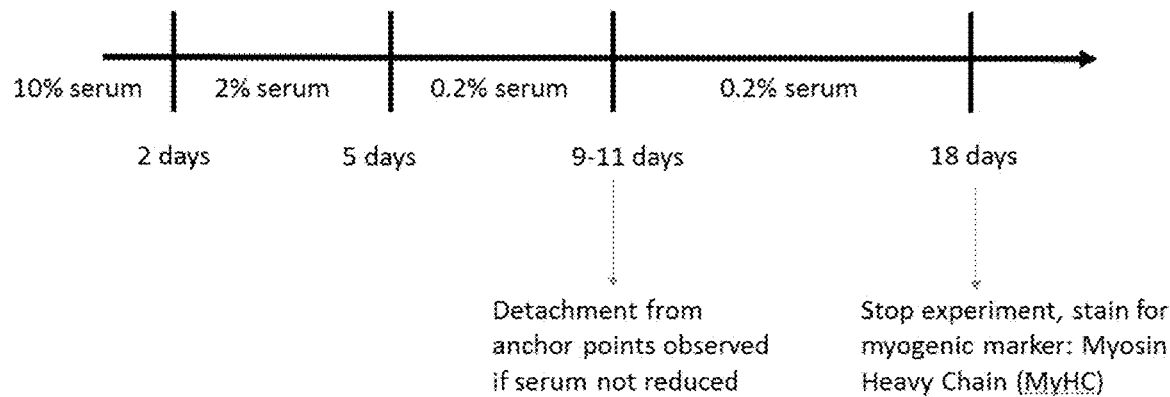
FIG. 23A
Myotube
FIG. 23B
FIG. 23C
Multi-Nucleated Myotube
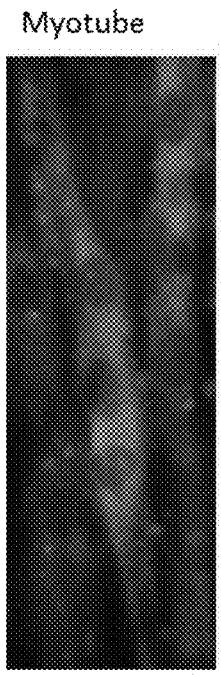
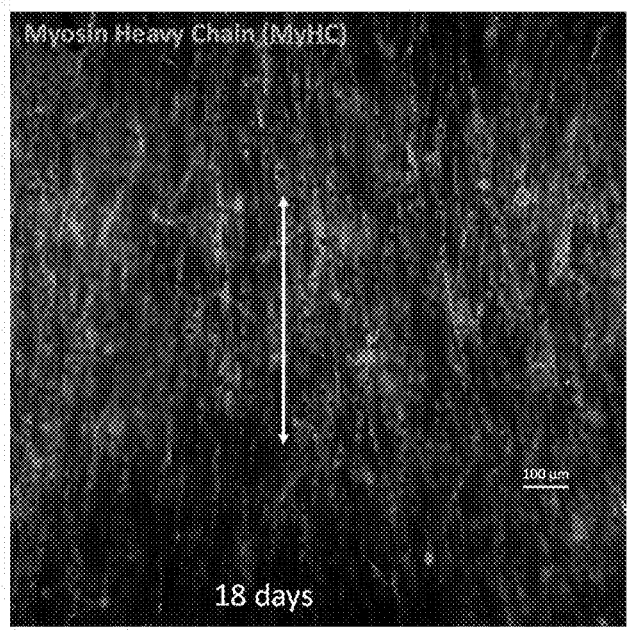
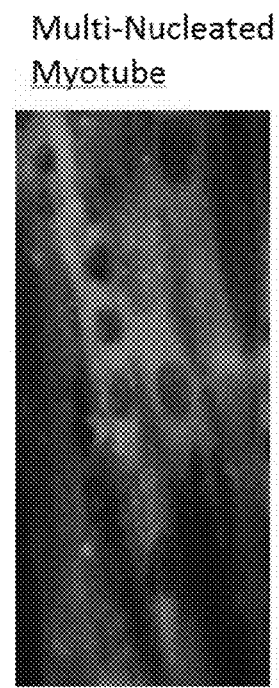

FIG. 36
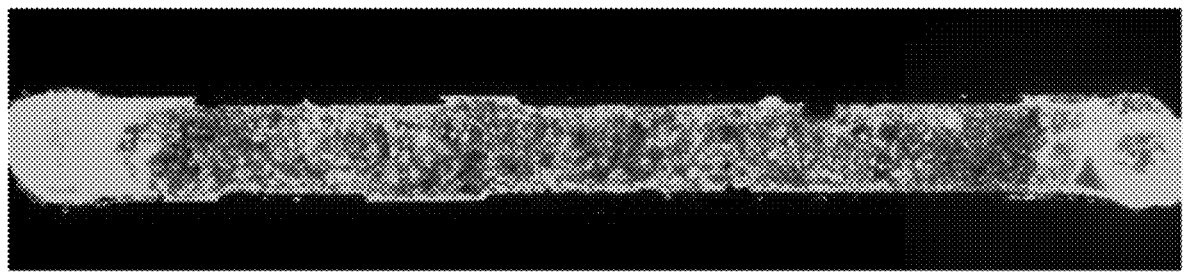
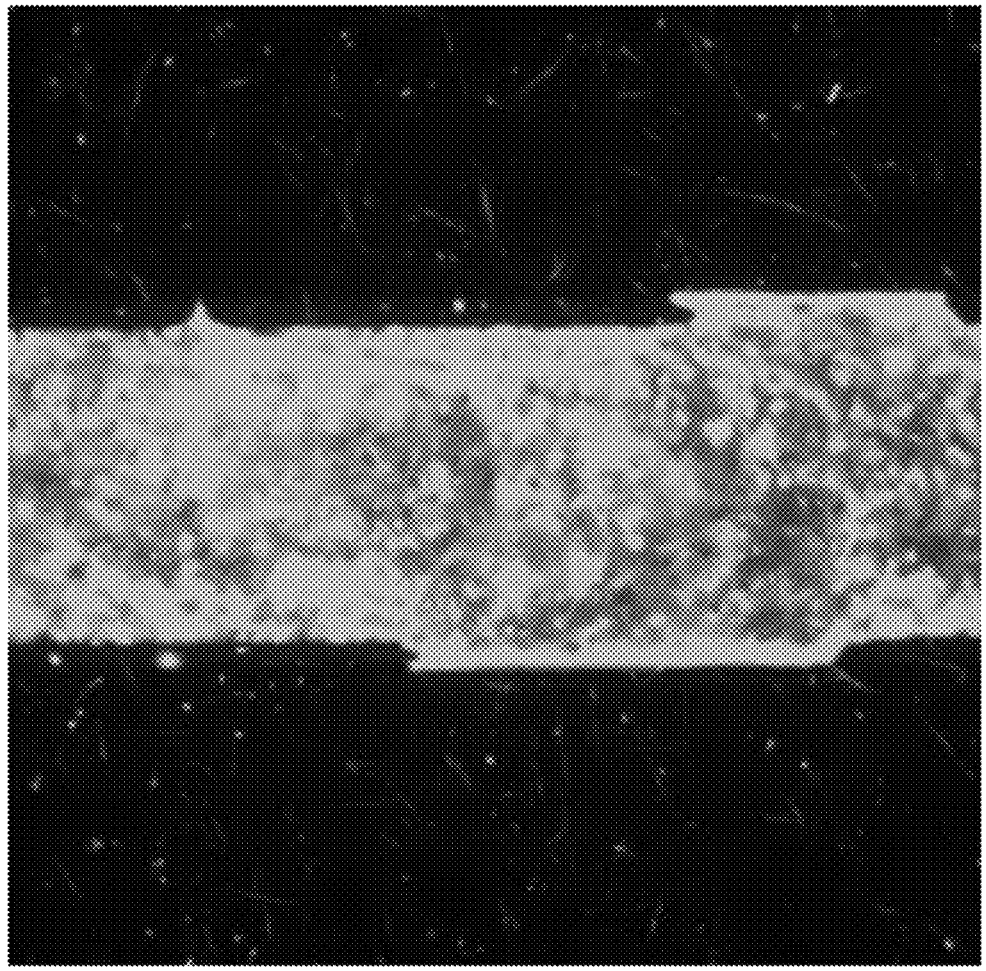

FIG. 47
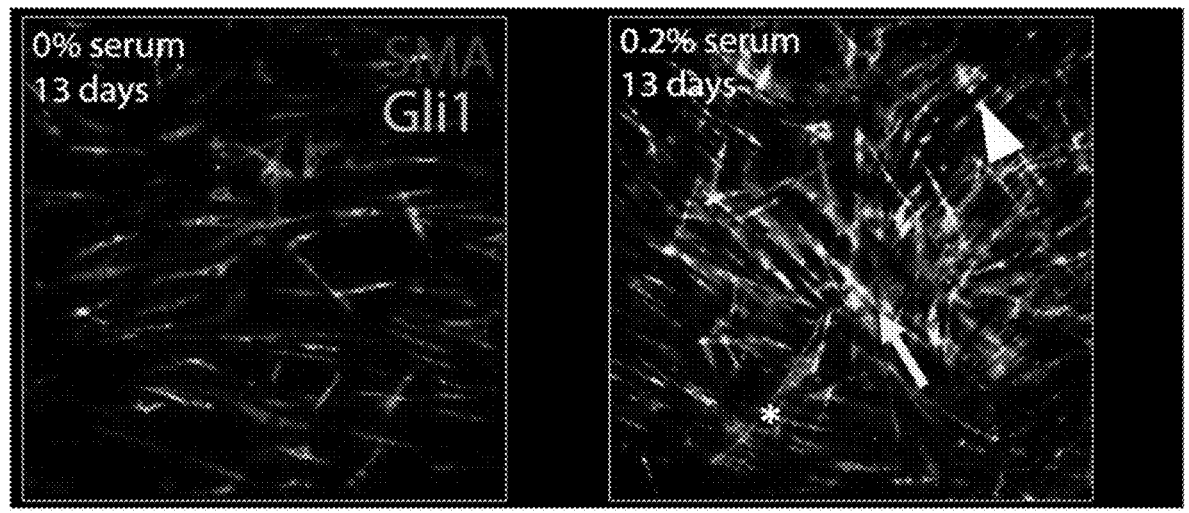
V.
Gold standard mouse
bleomycin model

SYSTEMS AND METHODS FOR IMMOBILIZING EXTRACELLULAR MATRIX MATERIAL ON ORGAN ON CHIP, MULTILAYER MICROFLUIDICS MICRODEVICES, AND THREE-DIMENSIONAL CELL CULTURE SYSTEMS

CROSS-REFERENCE TO RELATED APPLICATIONS

This application is a U.S. National Phase application under 35 U.S.C. § 371 of International Application No. PCT/US2016/044321, filed on Jul. 27, 2016, which claims priority to U.S. Provisional Application Ser. No. 62/197,444, filed on Jul. 27, 2015, U.S. Provisional Application Ser. No. 62/348,036, filed on Jun. 9, 2016, and U.S. Provisional Application Ser. No. 62/348,055, filed on Jun. 9, 2016, all of which are incorporated by reference herein in their entirety.

BACKGROUND

Recapitulating native three-dimensional (3D) organ microenvironments is a fundamental challenge in the development of biomimetic models of human physiology and disease. Microenvironmental cues such as local architecture, mechanical forces, and biochemical signals can define the physiological, or pathological situation in vivo. The extracellular matrix (ECM), serving as both a structural scaffold and cell adhesion substrate, possesses a tissue-specific composition and topology that can instruct diverse processes including growth, differentiation, and tissue morphogenesis/remodeling. In polarized tissues, such as the epithelium and endothelium, cells can interact with a planar layer of ECM called the basement membrane, while in tissues such as muscle and connective tissue/stroma, the cells reside in a truly 3D milieu of ECM and surrounding cells. By reconstituting the microenvironment, 3D models can facilitate investigation of-relevant human physiological and pathophysiological processes involving tissue elements such as stroma and their interfaces with epithelial and vascular components.

3D culture platforms have been developed that aim to model the native tissue microenvironment. Specific examples include hydrogels derived from native ECM or synthetic materials, solid state polymeric scaffolds, and matrix/scaffold-free systems such as spheroid cultures, with ECM gels being the most commonly employed. While such 3D hydrogel-based models can reconstitute the composition and mechanical properties of the native tissue microenvironment, critical aspects of organ structure such as patterned tissue-tissue interfaces and dynamic mass transport are absent in these models.

One approach to meet these challenges is to leverage biomimetic microengineering techniques to develop microphysiological models of human tissues and organs, termed "organs-on-chips." Comprised of 3D arrangements of perfusable microchannels, human organs-on-chips can allow for precise control of dynamic flow conditions and application of physical stimuli to cells and engineered tissues equivalents. Researchers have sought to create systems that incorporate 3D ECM gels, which mimic the in vivo stromal compartment to facilitate the study of angiogenesis, tumor cell invasion, and metastasis.

There remains a need to be able to control the spatial geometry and microarchitecture of the ECM hydrogel in these 3D culture organ-on-a-chip systems in order to develop improved microphysiological models. Furthermore, there remains a need to be able to prevent detachment of the ECM gel from the anchoring substrate due to cell-mediated contraction, resulting in the loss of the originally defined construct geometry and limited timeframes of experimentation.

The problem of cellular contraction of hydrogel matrices and detachment during 3D culture is a common obstacle to hydrogel anchorage in traditional cell culture models. A technique is needed that enables culture and maintenance of living cells in a 3D ECM environment for prolonged periods of time without causing significant changes to the volume of hydrogel and preventing loss to its structural integrity.

SUMMARY

The presently disclosed subject matter provides a method for anchoring of protein-composed 3D cell culture substrates in biomimetic microdevices and/or organ-on-a-chip platforms and/or general 3D cell culture systems. The presently disclosed subject matter can control the location at which a hydrogel construct detaches from the substrate, thereby creating a predictable geometric change. The presently disclosed subject matter can have specific applications beyond establishing construct stability, including but not limited to shaping the geometry of living tissues in vitro by harnessing cell-mediated contractile forces to contract the 3D tissue in a rationally designed manner by patterning the locations of tissue anchorage. In certain embodiments, the method can include selecting one or more substrates for tissue growth. In certain embodiments, the method can further include identifying desired tissue anchorage points on the one or more selected substrates to facilitate creation of rationally designed tissue geometries by allowing the natural process of cellular contraction to occur. In certain embodiments, the method can further include coating the one or more selected substrates with a heterobifunctional crosslinker at the identified desired tissue anchorage points. In certain embodiments, the method can further include curing the heterobifunctional crosslinker to the one or more substrates. In certain embodiments, the method can further include adding a gel layer embedded with at least one of tissue and cells to the one or more substrates. In certain embodiments, the method can further include allowing cell-mediated contractile forces to shape tissue geometry as the gel layer contracts between the fixed anchorage points.

In certain embodiments, the heterobifunctional crosslinker can be sulfo-SANPAH.

In certain embodiments, the substrate can be poly-dimethyl-siloxane (PDMS). In certain embodiments, the substrate can be sulfo-SANPAH. In certain embodiments, the substrate can be composed of different build materials that can be coated with a heterobifunctional crosslinker at the identified desired tissue anchorage points. In certain embodiments, the substrate on which the disclosed methods can be performed can be any polymeric, glass, and metal surfaces that are compatible with sulfo-SANPAH and/or any heterobifunctional crosslinkers that would serve the same function as sulfo-SANPAH.

In certain embodiments, the gel layer can include extracellular matrix proteins. In certain embodiments, the extracellular matrix proteins can be selected from the group consisting of, but not limited to, collagen, fibronectin, laminin, hyaluaronic acid, and mixtures thereof.

In certain embodiments, tissue and cells embedded within the gel layer can be fibroblasts. In certain embodiments, the tissue and cells embedded within the gel layer can be at stromal tissue and stromal cells. In certain embodiments, the tissue and cells embedded within the gel layer can be myoblasts. In certain embodiments, the tissue and cells embedded within the gel layer can be mesenchymal stem cells. In certain embodiments, the tissue and cells embedded within the gel layer can be vascular cells. In certain embodiments, the tissue and cells embedded within the gel layer can be epithelial cells. In certain embodiments, any other type of tissue and cells can be embedded within the gel layer.

In certain embodiments, the desired tissue anchorage points can be within a single horizontal plane. In certain embodiments, the desired tissue anchorage points can be within a plurality of horizontal planes. In certain embodiments, the desired tissue anchorage can be within a single vertical plane. In certain embodiments, the desired tissue anchorage can be within a plurality of vertical planes. In certain embodiments, the desired tissue anchorage can be within a single angled plane. In certain embodiments, the desired tissue anchorage can be within a plurality of angled planes. In certain embodiments, the desired tissue anchorage can be within a plurality of horizontal, vertical, and angled planes.

In certain embodiments, a first biopsy punch can be used to create a cell culture chamber in the substrate, and a second biopsy punch can be used to create outer nodes in the substrate that overlaps with a portion of the cell culture chamber. In certain embodiments, the outer nodes can be used as tissue anchorage points. In certain embodiments, a mold can be generated by 3D printing, photolithography, stereolithography, or other similar method(s). In certain embodiments, the mold can be used to create a cell culture chamber and anchorage points. In certain embodiments, a substrate can be directly etched and/or ablated using etchants, laser, and/or similar method(s) to create a cell culture chamber and anchorage points.

In certain embodiments, the presently disclosed subject matter further provides a technique to form and maintain 3D tissue in a microengineered cell culture device. In certain embodiments, the microengineered device can include a body having one or more cell culture chambers. In certain embodiments, the walls of the chamber can be treated with a heterobifunctional crosslinker and the chamber walls can form a substrate for hydrogel attachment and tissue growth. In certain embodiments, a hydrogel can be formed in the chamber and anchored to the walls of the chamber. In certain embodiments, the hydrogel can contain cells. In certain embodiments, a first microfluidic channel can be disposed above the gel layer. In certain embodiments, a second microchannel can be disposed under the gel layer. In certain embodiments, the microchannels can be perfused with culture media, blood, artificial blood, and other fluids to maintain and/or stimulate the cells embedded in the gel.

In certain embodiments, the presently disclosed subject matter further provides a microengineered perfusable lumen sculpted from engineered tissue. In certain embodiments, the perfusable lumen can include a body having a microchannel. In certain embodiments, the walls of the microchannel can form a substrate for tissue growth. In certain embodiments, the perfusable lumen can include a tissue embedded in a gel layer adhered to each of three different walls of the microchannel. In certain embodiments, the tissue can be unconnected to a fourth wall of the microchannel such that the tissue is shaped to create a semicircular opening within the microchannel. In certain embodiments, the semicircular opening can extends through a length of the microchannel and forms a conduit.

In certain embodiments, the conduit formed can be injected with a gel containing tissue, resulting in a tissue-to-tissue interface without using an intervening membrane.

In certain embodiments, the presently disclosed subject matter further provides methods of fabricating a microengineered perfusable lumen sculpted from tissue. In certain embodiments, the method can include fabricating a microchannel in a first body. In certain embodiments, the first body can form a substrate for tissue growth such that the microchannel is fabricated by bonding a second body to the first body. In certain embodiments, the method can further include injecting the microchannel with a heterobifunctional crosslinker. In certain embodiments, the method can further include curing and/or activating the heterobifunctional crosslinker. In certain embodiments, the method can further include replacing the second body with a third body to form a four-sided microchannel having three different sides treated with the heterobifunctional crosslinker. In certain embodiments, the method can further include injecting a gel layer embedded with at least one of tissues and cells into the microchannel. In certain embodiments, the method can further include allowing cell-mediated contractile forces to shape tissue geometry as the gel layer contracts, forming a semicircular conduit along a length of the microchannel.

In certain embodiments, the microchannel can be formed using photolithography.

In certain embodiments, upon formation of the conduit, the method can further include injecting the conduit with a gel containing tissue, resulting in a tissue-to-tissue interface without use of an intervening membrane.

BRIEF DESCRIPTION OF THE FIGURES

FIG. 10A illustrates exemplary images of dense regular connective tissue and FIG. 10B illustrates exemplary images of microengineered connective tissues that have been in vitro for nine to ten days.

FIG. 11 is a table illustrating orientation data for coherency and dominant direction of fibronectin and nuclei alignment.

FIGS. 12A and 12B illustrate examples of cell nuclei orientation analysis for unpatterned and/or contracted samples (FIG. 12A) and for 2-node aligned samples (FIG. 12B).

FIGS. 14A and 14B illustrates parallel cellular cytoskeleton and ECM in sculpted 2-node microtissues.

FIGS. 15A, 15B, and 15C illustrate images depicting sculpted connective tissue morphogenesis.

FIGS. 16A and 16B illustrate images depicting the SMA distribution for sculpted samples without any growth factors (16A) and plate-bound samples with growth factors (FIG. 16B).

FIGS. 20A and 20B are Z-stack images generated from F-actin staining the control sample (FIG. 20A) and the sulfo-SANPAH treated sample (FIG. 20B).

FIGS. 21A and 21B illustrate microscopic images of C2C12/collagen cultured in sulfo-SANPAH treated PDMS over 30 days using phase contrast microscope and confocal microscope.

FIG. 22 illustrates an experiment timeline for myogenic differentiation.

FIG. 23A illustrates the myotube after being stained with a myogenic marker.

FIG. 23B illustrates results of the samples being stained with the Myosin Heavy Chain marker at 18 days. FIG. 23C illustrates the multi-nucleated myotube after being stained with a myogenic marker.

FIG. 36 depicts the cell viability of the biomimetic model after 72 hours of incorporating the gel layer.

FIG. 47 depicts the presence of Gli-1 in the stromal layer of the five-layer model.

DETAILED DESCRIPTION

The presently disclosed subject matter provides systems and methods to form and maintain cell-laden 3D hydrogel constructs without gel detachment and contraction. The presently disclosed subject matter further enables cell laden 3D hydrogel constructs to be firmly anchored to the substrate, allowing for tissue patterning and shaping using such hydrogel constructs. The presently disclosed subject matter further allows the 3D hydrogel constructs to have long-term stability without significant deformation in shape and/or binding to the substrate. The presently disclosed subject matter further provides an approach to address the needs for microscale control in shaping the spatial geometry and microarchitecture of 3D collagen hydrogels. In certain embodiments, the disclosed subject matter provides for methods and systems that use N-sulfosuccinimidyl-6-(4'-azido-2'-nitro-phenylamino)hexanoate, hereinafter also referred to as sulfo-SANPAH, as a covalent crosslinker between collagen type I hydrogels and poly(dimethylsiloxane), hereinafter referred to as PDMS, a commonly used building material for organ-on-a-chip devices.

Figure 1:
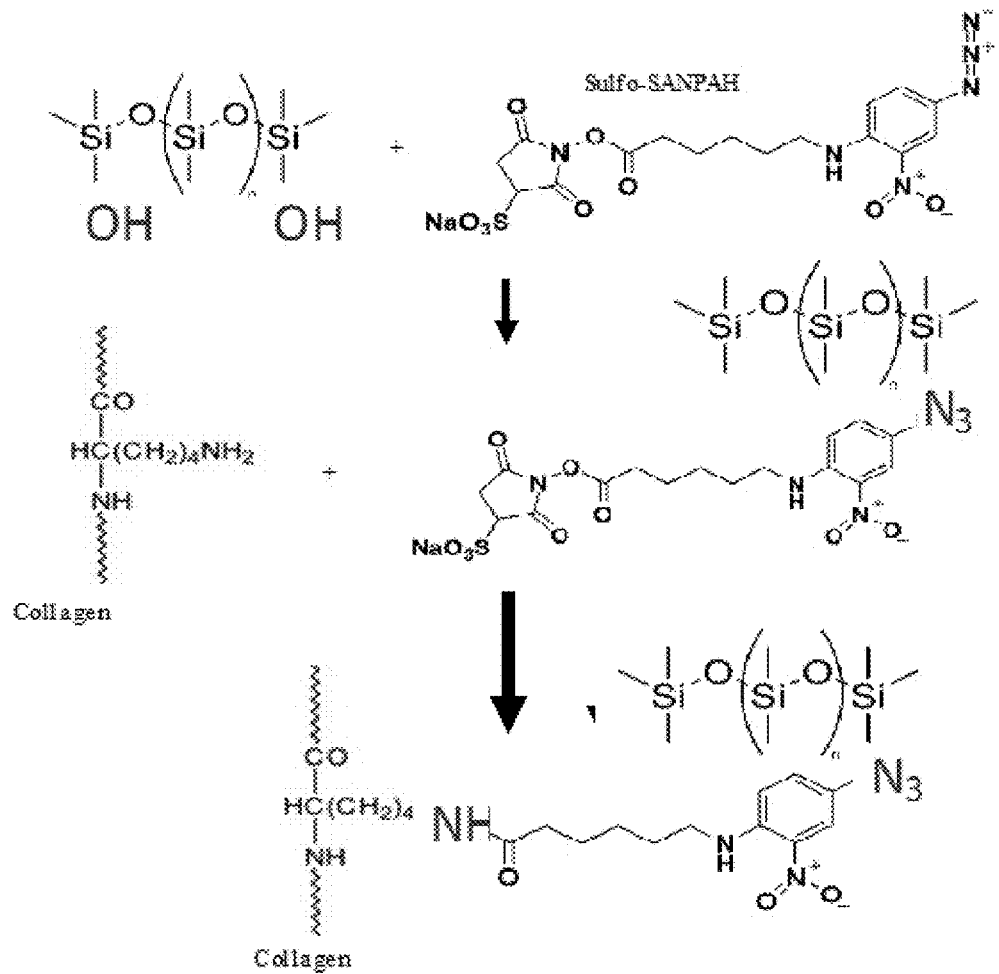
FIG. 1 is a diagram illustrating the chemical structure of sulfo-SANPAH and a two-step reaction scheme depicted illustrating collagen being chemically tethered to the surface of PDMS.

FIG. 1 is a diagram illustrating the chemical structure of sulfo-SANPAH. Sulfo-SANPAH is a heterobifunctional cross-linker that contains an amine-reactive NHS ester and a photoactivatable nitrophenylazide group. It is water soluble and reactive to amine groups and nucleophiles. In certain embodiments, the disclosed subject matter provides a simple and rapid means of improving ECM hydrogel anchorage to PDMS surfaces (e.g., substrates), thereby allowing researchers to curtail gel contraction and/or detachment in certain applications, or by patterning differential anchorage strength in innovative ways. For example, the two step reaction scheme depicted in FIG. 1 illustrates how the collagen is chemically tethered to the surface of PDMS.

Figure 2A:
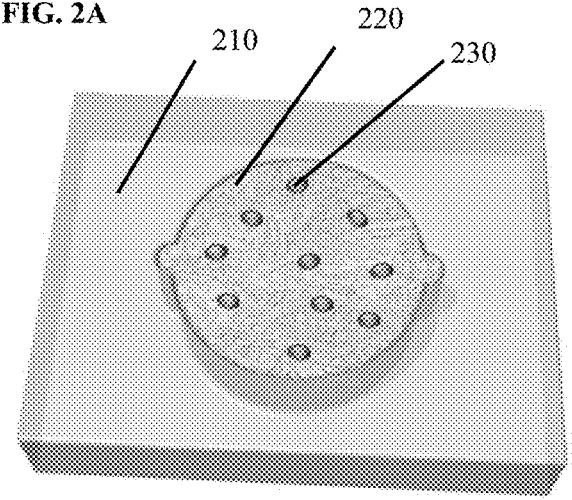
FIGS. 2A and 2B are diagrams illustrating schematics of 2-D patterning for microtissue sculpting.
Figure 2B:
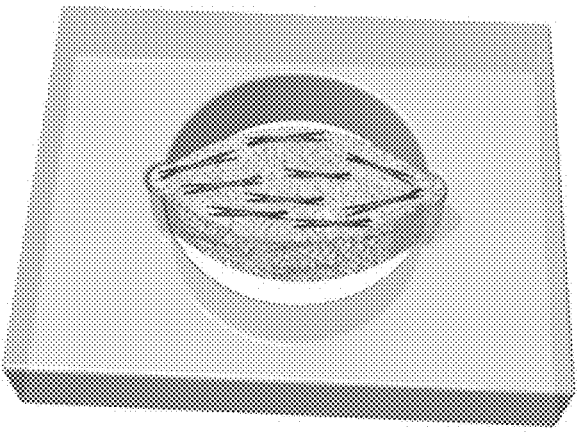
Figure 2C:
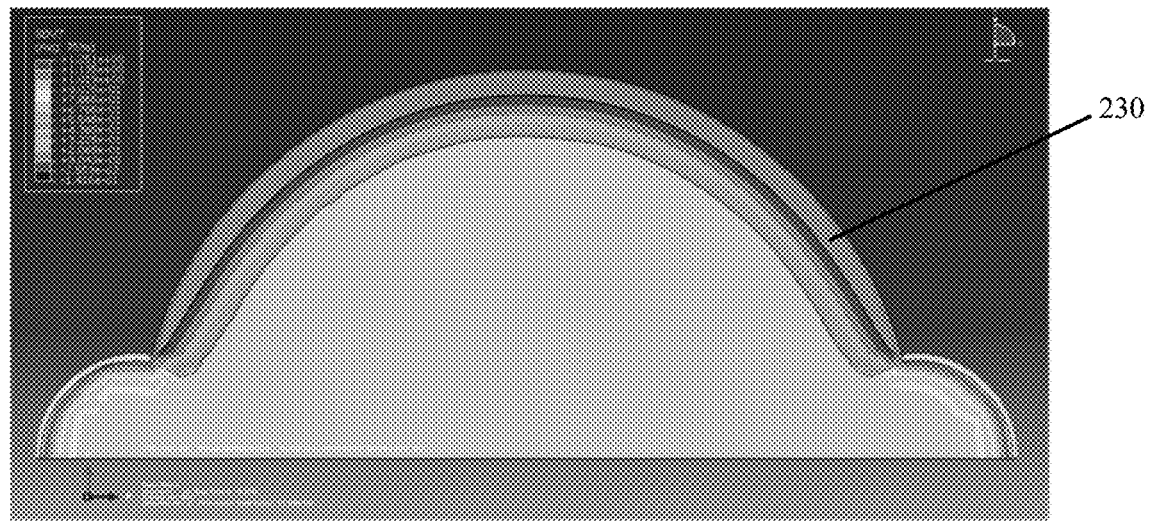
FIG. 2C is a diagram illustrating a computational model predictions of gel detachment from untreated surfaces due to cell-mediated contraction.

FIGS. 2A and 2B are diagrams illustrating schematics of 2-D patterning for microtissue sculpting. While the patterning shown in FIGS. 2A and 2B are in a 2-D plane, the construct disclosed can fit the definition of a 3-D tissue, commonly referred to as 3-D patterning, which entails anchoring points in different horizontal planes, even though both situations involve culture of cells within a 3-D gel matrix. FIG. 2A illustrates the sample at 0 days when the gel 220 is in contact with all surfaces in the PDMS well 210, but only the semi-circular nodes 230 have been sulfo-SANPAH treated. FIG. 2B illustrates the sample at 2-3 days of being cultured, when the stromal cells have spread in the gel and have generated traction forces via their adhesions to the collagen matrix. This cell-generated force can lead to detachment of the gel matrix from the untreated surfaces, followed by contraction and compaction to align along the axis created by the two anchoring nodes. FIG. 2C is a diagram illustrating a computational model predictions of gel detachment from untreated surfaces due to cell-mediated contraction. The diagram of FIG. 2C illustrates the correlation of experimental results with mathematical theory. Simulation results illustrated in FIG. 2C depict that summed cellular traction forces in the two-node configuration can drive alignment (x-direction in FIG. 2C) and compaction (y-direction in FIG. 2C). The rim along the top indicates space where the gel has detached from the PDMS wall and contracted after 2 days in the simulations.

In certain embodiments, cellular contraction of hydrogel matrices, typically considered to be an obstacle to hydrogel anchorage in conventional methods and systems, can be used by the presently disclosed subject matter to control the location at which a hydrogel construct detaches, thereby creating a predictable geometric change. In certain embodiments, collagen-to-PDMS anchorage can provide improved increases in mechanical integrity over conventional methods, which can be used to 'sculpt' diverse microtissue geometries. In certain embodiments, the presently disclosed subject matter facilitates engineering of various shapes including aligned microtissues with skeletal muscle-like cellular architecture and ultrastructure by patterning nodes of increased local surface area for anchorage into the initial construct geometry. By selectively patterning sulfo-SANPAH on surfaces of collagen-filled microchannels while allowing cell-mediated contraction to detach collagen from others, perfusable lumens can be created within stromal microtissues.

In certain embodiments, the presently disclosed subject matter can mimic the contraction and movements of embryonic tissues, following similar tissue patterning as those in organismal development during the embryonic stage. For example, contractile forces generated by cells can have a pivotal role in the formation of specialized tissue patterns and structures during embryonic development (e.g., the development of aligned tissues such as musculoskeletal and connective tissues). In certain embodiments, the presently disclosed subject matter provides methods inspired by this biomechanical process of tissue morphogenesis to pattern three-dimensional (3D) living tissues in vitro.

In certain embodiments, mechanical forces can control biological processes that drive tissue and organ development during embryogenesis. For example, various different types of forces can act in concert with genes and soluble morphogens to induce the transformation of cellular aggregates in an early embryo into complex 3D tissues having unique architectures and specialized functions. In particular, intracellular mechanical forces generated by actin-myosin contraction can be transmitted to neighboring cells and the extracellular environment to drive tissue assembly and pattern formation during morphogenesis. For example, traction forces exerted by mesenchymal cells can induce contraction and reorientation of the ECM, leading to tissue compaction and alignment that typically occur during the development of certain types of connective tissues.

In certain embodiments, fibroblast-generated traction forces can wrinkle underlying silicon substrates and deform collagen gels, causing morphogenesis of aligned tissue structures including tendons, ligaments, and muscles. These dynamic morphological changes due to cell-generated forces can occur while contractile tissues are mechanically constrained. These constraints often arise from the geometry and physical properties of adjacent tissues, and have a profound influence on morphogenesis by creating spatial variations in traction forces. Studies have shown that this type of non-uniform, multiaxial mechanical loading due to boundary constraints gives rise to various modes of structural deformation such as folding, extension, and contraction that sculpt living tissues into different shapes. This geometric modulation of multicellular contractility through mechanical boundary constraints represents a key biophysical mechanism underlying the emergence of distinct tissue morphologies during the development of complex living organisms.

In certain embodiments, the disclosed subject matter provides a novel 3D cell culture strategy inspired by this fundamental principle of morphogenesis to engineer the shape of 3D living tissues in vitro. In certain embodiments, this strategy is based on the use of heterobifunctional crosslinking chemistry to spatially pattern surface anchorage of cell-laden ECM hydrogel scaffolds. The well-defined and readily adjustable boundary constraints attainable in this approach facilitate variation in the spatial distribution of cell contractility and therefore allow control over the change and evolution of tissue morphology due to traction force-induced hydrogel contraction and detachment. In certain embodiments, the disclosed surface engineering techniques also provide for stable tethering and long-term maintenance of 3D tissue constructs, providing capacity for direct visualization and morphometric analysis during the course of tissue pattern formation. For example using collagen hydrogels that encapsulate stromal fibroblasts or myoblasts, spatially guiding contractive deformation of ECM scaffolds can be used to sculpt 3D tissues into various simple shapes. In certain embodiments, muscle constructs can be formed to exhibit morphological properties that closely match those of native tissue. Additionally, In certain embodiments, the disclosed subject matter provides microengineered systems that model vascular perfusion of stromal tissue to enable physiological tissue microarchitecture in tissue- and organ-on-a-chip microdevices.

In certain embodiments, engineering the surface anchorage of cell-laden extracellular matrix (ECM) hydrogels can be used to control the spatial distribution of cellular traction forces and the resultant matrix contraction. In certain embodiments, 3D tissue constructs can be actively shaped and maintained long term by culturing contractile cells such as fibroblasts and myoblasts in collagen scaffolds. In certain embodiments, 3D tissues can additionally or alternatively be sculpted with physiological microarchitecture by creating microengineered stroma that includes perfusable lumen-like structures. In certain embodiments, the presently disclosed subject matter can provide a simple yet robust 3D culture platform for the development of cell-based screening assays and physiological tissue models for a wide variety of applications.

Detachment and shrinkage of 3D tissue constructs have been a long-standing obstacle to hydrogel anchorage in traditional cell culture models, making it extremely difficult, if not impossible, to recapitulate compaction of living tissue in vivo. As tissue develops, cellular constituents can proliferate and can secrete extracellular matrix proteins to remodel their matrices, and these natural development processes can lead to significant increases in the density of cells and matrices. Mimicking this physiological compaction process in vitro has not previously been possible in conventional systems and technique due to the technical challenges of culturing and maintaining cells (e.g., contractile cells such as fibroblasts found in the connective tissue, muscle cells, etc.) in a 3D hydrogel environment for prolonged periods without gel shrinkage and detachment from culture substrates. However, the presently disclosed subject matter can overcome this obstacle by controlling the location at which a hydrogel construct detaches, thereby creating a predictable geometric change.

Sulfo-SANPAH Protocol

For the purpose of illustration and not limitation, an exemplary method for cross-linking sulfo-SANPAH to a PDMS substrate is provided herein. In certain embodiments, the sulfo-SANPAH (hereinafter also referred to as ProteoChem) can be dissolved in deionized water at a concentration of 10 mM and then diluted in deionized water to a desired working concentration (e.g., 1 mg/mL). In certain embodiments, the sulfo-SANPAH solution can be placed on the PDMS substrate to fully cover the contact surface for the ECM hydrogel and exposed to UV light for 5 minutes. This solution can be aspirated and the previous step repeated for another 5 minutes of UV exposure. The PDMS surface can then be thoroughly washed with a phosphate buffered saline (PBS) solution and prepared for collagen deposition.

Figure 3:
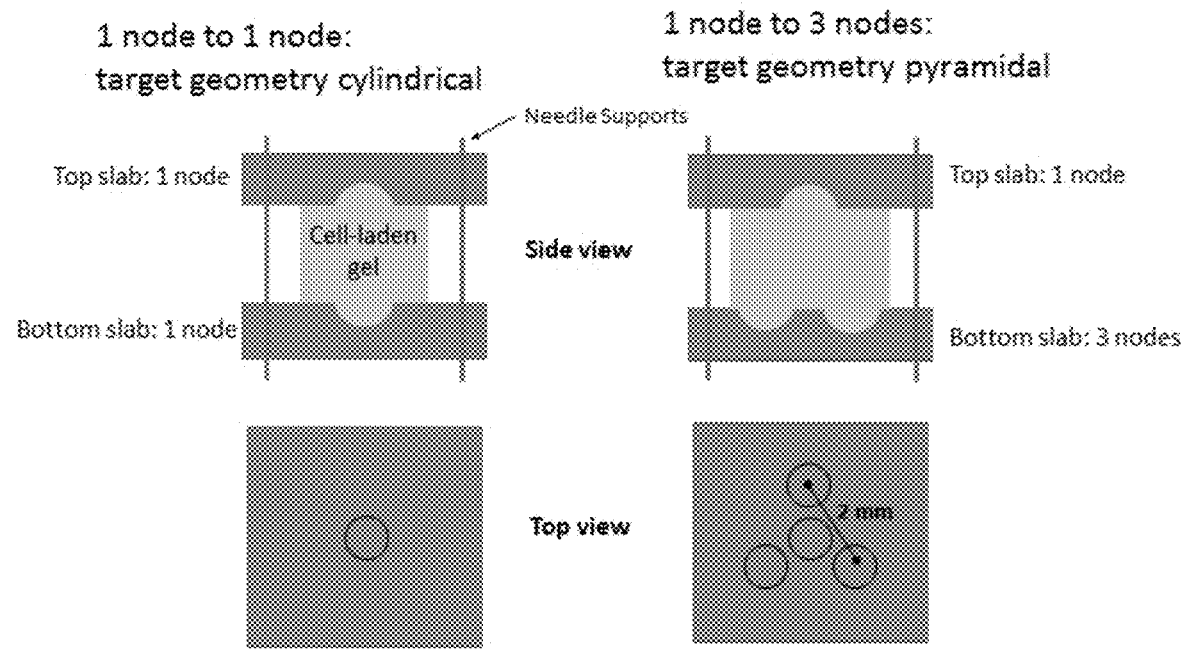
FIG. 3 illustrates a schematic of 3-D patterning for microtissue sculpting.
Figure 4:
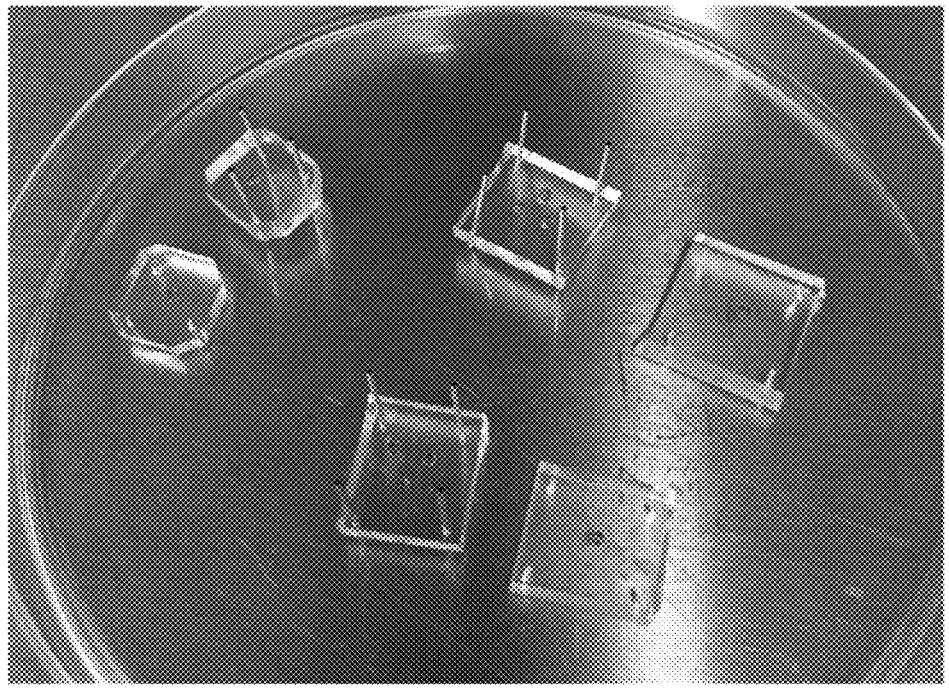
FIG. 4 illustrates a photograph in which the sulfo-SANPAH solution is seen pipetted into each node.
Figure 5A:
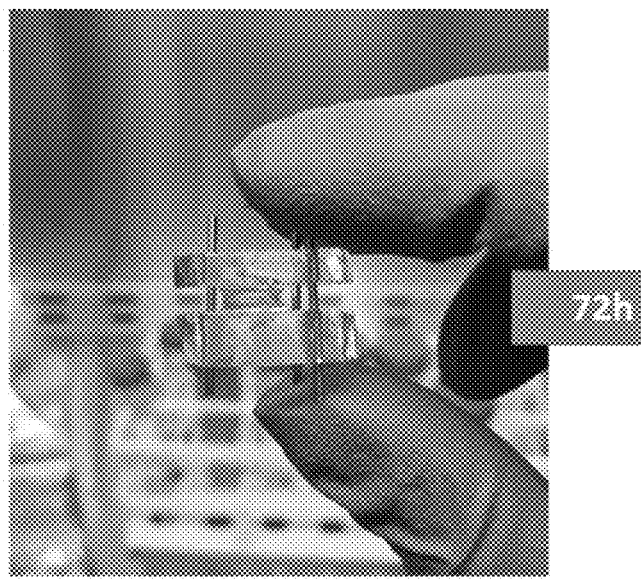
FIGS. 5A-5D are photographs illustrating the collagen gel layer being sandwiched between two PDMS layers.
Figure 5B:
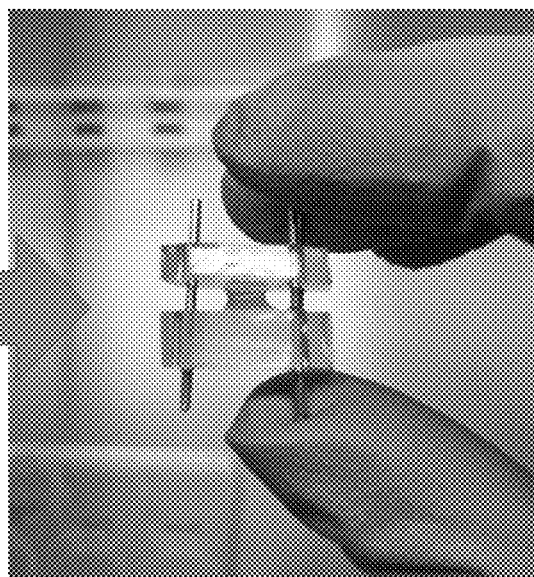
Figure 5C:
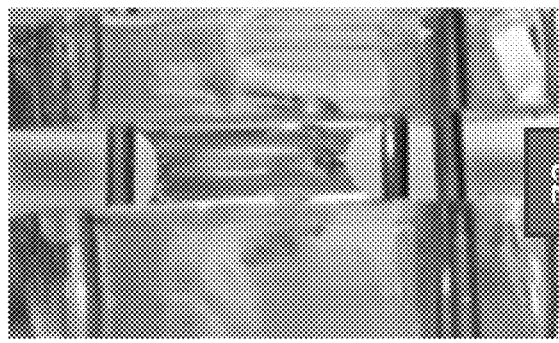
Figure 5D:
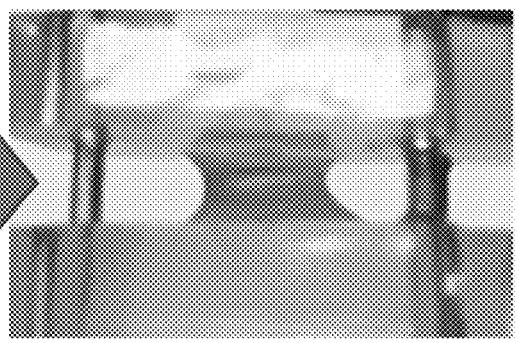

FIG. 3 illustrates a schematic of 3-D patterning for microtissue sculpting. In certain embodiments, an additional layer of complexity for engineering complex tissue and organ architecture can be incorporated by introducing anchorage points in multiple horizontal planes. Examples are illustrated of 1:1 and 1:3 designs for 3-D patterning. As shown in FIG. 3, sulfo-SANPAH can be used to treat nodes in upper and lower PDMS slabs. In certain embodiments, the cell-laden collagen precursor solution can be placed on the lower slab and using needle supports, the upper slab can be placed in contact with the gel, after which the sample can be incubated at 37° C. for gelation. After gelation, the samples can be placed in a 6-well plate and bathed in media for culturing. FIG. 4 illustrates a photograph in which the sulfo-SANPAH solution is seen pipetted into each node. In certain embodiments, after UV treatment, the collagen gel layer is sandwiched between the two PDMS layers as illustrated in FIGS. 5A-5D. FIG. 5A is a photograph of the construct at the start of the experiment at 0 hours. FIG. 5B is a photograph of the construct after 72 hours. FIG. 5C and FIG. 5D are zoomed in versions of FIGS. 5A and 5B, respectively.

Collagen Tear-Off and Fluorescence Quantification

In certain embodiments, in order to prepare bottom PDMS slabs for both Sulfo-SANPAH treated and untreated groups, PDMS pre-polymer (e.g., Sylgard 184) can be mixed at a 10:1 ratio with curing agent, poured into a petri dish, and subsequently can be cured at 65° C. For the treated group, the PDMS surface can be covered with sulfo-SANPAH and treated following the steps outlined above. In certain embodiments, the untreated group can be left as a control group without any surface treatments performed on the samples. To create circular PDMS wells, a top PDMS well with 2 mm hole punches can be conformally bonded to the bottom PDMS slab, followed by filling of the wells with a 2 mg/ml collagen type I precursor solution. In certain embodiments, after gelation, the top well layer can be peeled away and the molded collagen gel droplets can be manually detached from the surface using a Pasteur pipette. The resulting residual collagen layer, which can be detectable by immunohistochemistry, is an indicator that collagen to PDMS tethering has successfully occurred.

Collagen Droplet Detachment Assay

In certain embodiments, upon preparation of PDMS slabs and sulfo-SANPAH treatment method described herein, a collagen type I solution with PBS and 1N NaOH can be prepared and then deposited as 50 uL droplets in a 6×7 array on the PDMS surface of each dish. In certain embodiments, the droplets can be incubated at 37° C. in a cell culture incubator for 45 minutes for gelation. In certain embodiments, each dish can be filled with sufficient volume of canola oil, chosen due its increased viscosity, to fully cover the droplet surfaces and placed on an orbital shaker set at 150 rpm. In certain embodiments, these samples can be exposed to rotation for 6 hours and the detachment of droplets can be recorded.

Cell Culture

In certain embodiments, mouse embryonic NIH/3T3 fibroblasts and mouse C2C12 myoblasts can be employed in the cell shaping studies. For example, the NIH/3T3 cells can be cultured in Dulbecco's Modified Eagle Medium (DMEM) supplemented with 10% fetal bovine serum and 1% Penicilin-Streptomycin. In certain embodiments, cultures can be maintained in a tissue culture incubator at 37° C. and 5% $CO_2$.

Cell-Mediated Collagen Shaping

In certain embodiments, scaffolds for collagen shaping experiments can be prepared from a 1 mm thick PDMS slab, which can be cured in the manner described previously. For example, ell culture chambers can be cut into the PDMS slab with symmetrical outer nodes (number of nodes (n)=1, 2, 3, 4 and 5). In certain embodiments, the central portion of the chamber can be created using a 6 mm biopsy punch. In certain embodiments, outer nodes can be added in a symmetrical fashion using a 2.5 mm biopsy punch. In certain embodiments, the Sulfo-SANPAH solution can be prepared at a concentration of 1 mg/mL in diH$_2$O and pipetted into the outer nodes of each culture chamber in the treated group. In certain embodiments, the sulfo-SANPAH UV treatment can be performed as detailed above. In certain embodiments, the untreated group of samples can be left without any surface treatment.

In certain embodiments, the collagen precursor solution with a final concentration of 2.0 mg/mL can be prepared by mixing type I collagen, 10×DMEM, 1N NaOH, and PBS at ratios specified in the manufacturer's protocol. In certain embodiments, the collagen precursor solution can be mixed with mouse embryonic NIH/3T3 fibroblasts (e.g., having a concentration of 3×10$^6$ cells/mL), loaded into the PDMS culture chambers, and incubated for 1 hour at 37° C. for gelation. In certain embodiments, cultures can be immersed in culture medium and maintained in a 12-well plate within a tissue culture incubator at 37C/5% CO$_2$. In certain embodiments, cultures can be imaged daily over the course of seven days of culture using a Zeiss Axio Observer microscope.

Myoblast Alignment in PDMS Wells

In certain embodiments, C2C12 myoblast embedded collagen gel can be aligned in a PDMS well. In certain embodiments, in order to form such an alignment, a set concentration of sulfo-SANPAH (e.g., 1.0 mg/ml) can be selectively treated into a PDMS well containing a central chamber and two symmetric outer nodes. In certain embodiments, the PDMS well can be fabricated in the same manner with collagen shaping experiment. For example, the diameter of outer nodes and central chamber can be 2 mm and 6 mm, respectively. In certain embodiments, in order to initiate crosslinking between PDMS and Sulfo-SANPAH, a high power UV lamp can be used to photoactivate the crosslinker. In certain embodiments, following sulfo-SANPAH treatment, the PDMS chamber can be filled with collagen I precursor solution (e.g., at a concentration of 2.0 mg/mL) containing C2C12 myoblasts (e.g., at a concentration of 3×10$^6$ cells/mL) and then can be incubated for 30 min at 37° C. for gelation. In certain embodiments, the cell-laden collagen gel can be maintained at 37° and 5% CO$_2$ in DMEM containing 10% FBS for 2-3 days. In certain embodiments, the culture medium can then be replaced with DMEM supplemented with 10% horse serum to induce myotube differentiation over a period of 7 days.

In certain embodiments, the C2C12 collagen constructs can be prepared for immunostaining to assess cell alignment. In certain embodiments, the constructs can be fixed in 4% paraformaldehyde for 15 minutes. In certain embodiments, after thorough washing in PBS, the cells can be permeabilized in 0.5% Triton-X and then blocked in 1% bovine serum albumin (BSA). In certain embodiments, the constructs can then be incubated with primary anti-alpha-actinin antibody overnight at 4° C. followed by secondary antibody-fluorescein isothiocyanate (FITC), which can be treated for overnight at 4° C. In certain embodiments, both antibodies can be diluted in 1% BSA (e.g., at a ratio of 1:200). In order to stain nuclei and F-actin, the samples were incubated with 4',6-diamidino-2-phenylindole (DAPI) (e.g., which can be diluted at a ratio of 1:500) and phalloidin (e.g, which can be diluted at a ratio of 1:200) for 2 hours at room temperature. To remove the remaining reagents in a washing step, lx DPBS can be applied for 3 minutes for three times. In certain embodiments, the samples can then be imaged using a LRSM confocal microscope.

In certain embodiments, the samples can be imaged using a scanning electron microscopy (SEM). For example, in SEM imaging, aligned C2C12 collagen constructs can be fixed in 1% glutaraldehyde in 0.1M cacodylate buffer (e.g., having pH 7) for 5 minutes. In certain embodiments, dehydration can be gradually conducted with 50%, 75%, 90%, and 99.9% ethanol for 5 minutes each and the sample can be dried using critical point dryer. In certain embodiments, the sample can be sectioned longitudinally and imaged using the SEM.

Microfluidic Lumen Formation

In certain embodiments, a straight channel microdevice can be fabricated by casting a PDMS pre-polymer against a photolithographically prepared master that contained a micropattern made of photoresist. In certain embodiments, the microdevice can include a straight channel having dimensions of 1 mm (width)×450 μm (height). In certain embodiments, in order to selectively treat three surfaces of the microchannel with sulfo-SANPAH, the microdevice can be conformally bonded onto a temporary PDMS slab. The sulfo-SANPAH solution can be injected into the microchannel and two side walls and a ceiling of the microchannel can be treated with the sulfo-SANPAH solution. Subsequently, the microchannel slab can then be removed from the temporary PDMS slab and then transferred to a fresh PDMS substrate, thus leaving only the bottom of the microchannel untreated. By using such a method, selective treatment of sulfo-SANPAH solution can be achieved inside the microchannel.

In certain embodiments, following sulfo-SANPAH treatment of the device, a collagen gel precursor containing NIH3T3 fibroblasts can be injected into the microchannel. Specifically, the collagen precursor solution can be prepared by mixing 10×DMEM, rat tail collagen Type I, 0.2N NaOH, and 1×DMEM to achieve final collagen concentration of 2.0 mg/mL and cell density of 3 million cells/mL. In certain embodiments, after filling the microchannel with the precursor solution, the device can be placed in a cell culture incubator (e.g., at 37° C. and 5% CO$_2$) for 1 hour to allow for collagen polymerization. Once gelation is completed, the fibroblast culture can be maintained by diffusing medium for 3 days while gel contraction is monitored.

In certain embodiments, the presently disclosed subject matter provides for visualizing lumen geometry and cellular distribution in the collagen gel. In certain embodiments, the collagen gel fibers and nuclei of the fibroblasts can be fluorescently stained. In certain embodiments, the collagen gel and fibroblasts in the microdevice can be fixed overnight by filling the lumen with 4% paraformaldehyde. In certain embodiments, after thoroughly rinsing with PBS, the cells can be permeabilized with 0.25% Triton-X and blocked with 0.1% BSA in PBS. The sample can be incubated with anti-collagen I primary antibody followed by secondary antibody staining to stain the collagen fibers. Cell nuclei can be labeled with DAPI prior to mounting in Fluoroshield medium.

In certain embodiments, in order to demonstrate the functionality of the lumen, fluorescent microspheres can be perfused through the microchannel of a device still in active culture. In certain embodiments, the microsphere solution can be manually injected into the microchannel and the microsphere movement can be tracked by imaging using a microscope. Time lapse images can be recorded to track bead movement through the lumen that form within the device.

Statistical significance analysis of these samples can be performed using a two-tailed Student's t-test. The results of such an analysis can be presented as the mean±standard error of mean (S.E.M.). Differences can be considered statistically significant at a value of p<0.05 and/or of p<0.01 although other differences may also be statistically significant as known in the art.

EXAMPLES

Example 1: Sulfo-SANPAH-Mediated Collagen-to-PDMS Anchorage

In certain embodiments, sulfo-SANPAH can be used to conjugate collagen to poly(methyl methacrylate) and/or Arginylglycylaspartic acid (RGD) peptide to PDMS. Sulfo-SANPAH is cross-linked to PDMS via its nitrophenylazide group. During the UV treatment procedure described above (e.g., the sulfo-SANPAH solution being placed on the PDMS substrate and exposed to UV light for 5 minutes), a highly reactive nitrene can be formed from the nitrophenylazide group, which can then be cross-linked to double bonds on the PDMS surface. When a collagen solution is gelled in contact with a sulfo-SANPAH-coated surface, collagen fibers are crosslinked to the PDMS surface via the open NHS ester, as shown in FIG. 1.

Figure 6A:
FIGS. 6A and 6B show images in which a droplet of collagen gel was cast on PDMS that was either untreated (FIG. 6A) or sulfo-SANPAH-treated (FIG. 6B).
Figure 6B:
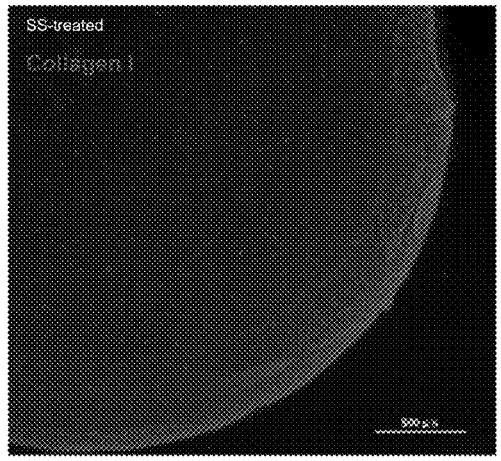

In this experiment, the functional strength (e.g., resistance to mechanical failure) of the interfacial bond between collagen and PDMS was assessed. FIGS. 6A and 6B show images in which a droplet of collagen gel was cast on PDMS that was either untreated (FIG. 6A) or sulfo-SANPAH-treated (FIG. 6B). The collagen was mechanically dislodged from the PDMS surface, followed by immunofluorescent staining to confirm the presence of anchored collagen in the SS-treated group.

Figure 6C:
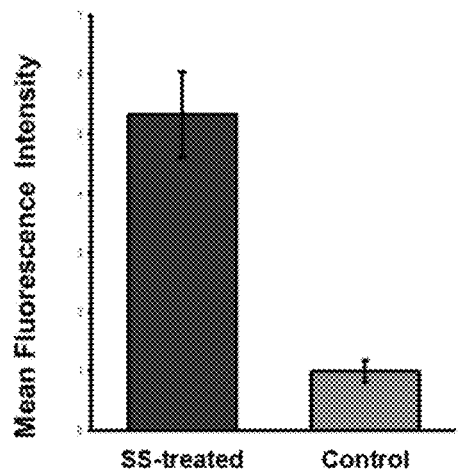
FIG. 6C illustrates a chart depicting the mean fluorescence intensity over the entire original surface area of gel anchorage.

After gelation, collagen gel droplets can be mechanically dislodged on SS-treated and untreated control PDMS surfaces, and then probed for the presence of residual collagen indicative of mechanical failure in the bulk gel and not at the interface as shown in FIG. 6B. Low levels of faint fluorescence can be observed throughout untreated PDMS surfaces with no discernable layer of residual fiber network except for sparse patches near the droplet boundaries (FIG. 6A), suggesting that the gel detached at the collagen-to-PDMS interface. By contrast, SS-treated PDMS surfaces retained a macroscopically visible collagen film, which appeared as a thin layer of fibrous collagen type I network with a greater than 5-fold increase in mean fluorescence intensity over the entire original surface area of gel anchorage (as shown in FIG. 6C). Thus, gel breakage can occur within the collagen fiber matrix, while the collagen-to-PDMS bonding at the interface can remain intact.

Figure 7A:
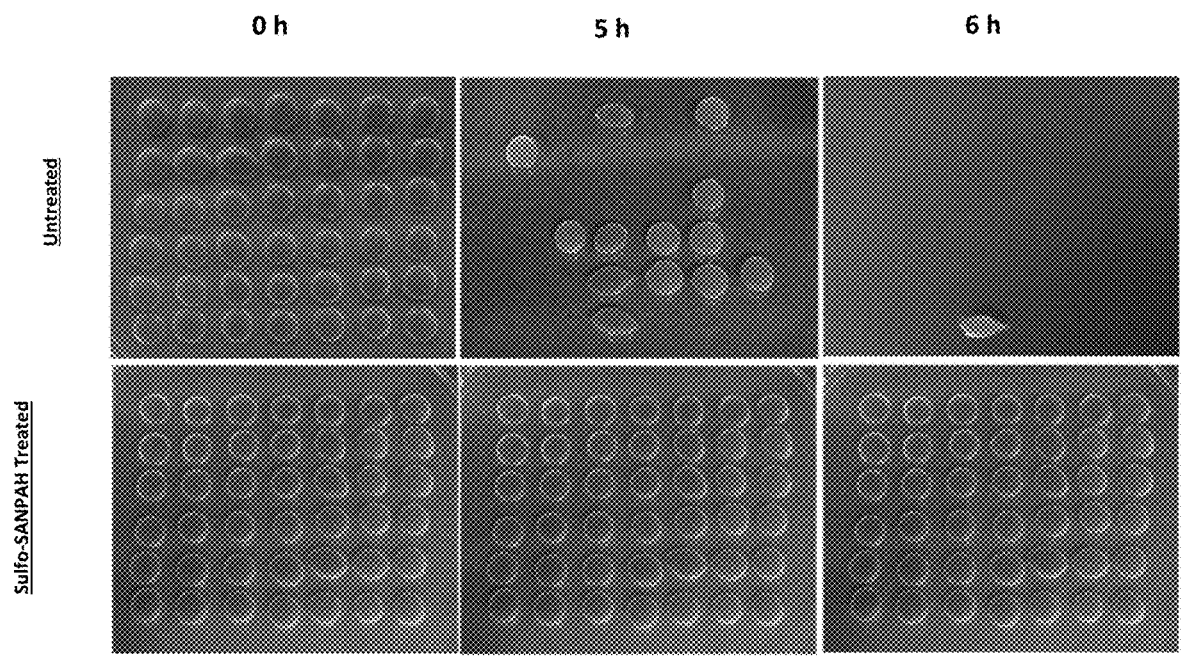
FIGS. 7A and 7B, which illustrate the results of an experiment investigating the effect of continuous mechanical strain on the collagen-to-PDMS anchorage.
Figure 7B:
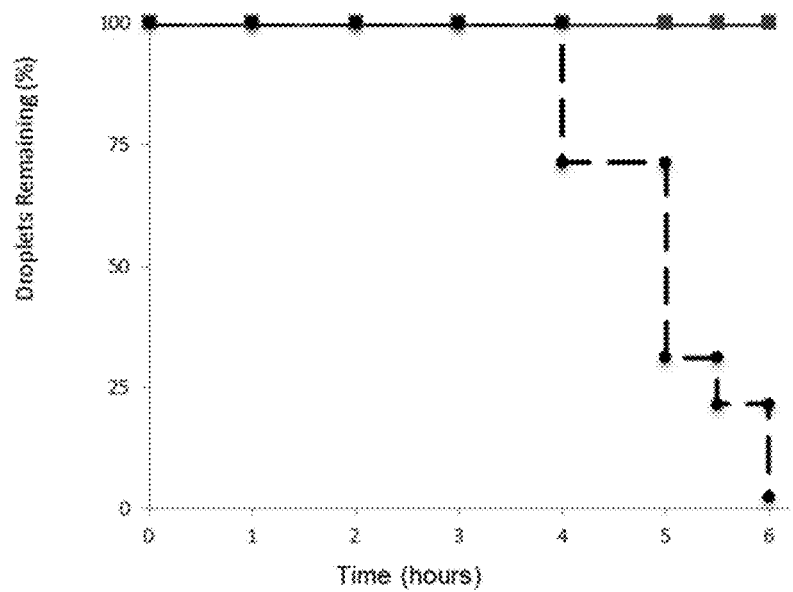

In certain embodiments, a similar approach can be used to investigate the effect of continuous mechanical strain on the collagen-to-PDMS anchorage. In certain embodiments, collagen droplets can be dropped on SS-treated and/or control PDMS substrates to continuous rotational shear stress over 6 hours in an oil medium, by being exposed to mechanical agitation using an orbital shaker As observed from FIGS. 7A and 7B, which illustrate the results of this experiment, no droplets detached in either group detached for the first 4 hours, suggesting that simple absorptive bonding of collagen to PDMS can provide a degree of short-term resistance to mechanical failure. However, 98% of droplets detached from the control surfaces between 4 and 6 hours. By 6 hours, essentially 100% of the collagen droplets on untreated PDMS surfaces had detached, while sulfo-SANPAH treatment successfully anchored collagen without any observable detachment. As observed from FIGS. 7A and 7B, sulfo-SANPAH treatment of PDMS surfaces can abrogate collagen droplet detachment in this assay, further confirming the mechanical integrity of collagen-to-PDMS anchorage using the disclosed method.

In certain embodiments, such functional demonstrations can extend to other specific applications of microengineered collagen hydrogels (e.g., stabilizing the bond between collagen gels and microchannel walls when exposing an incorporated lumen or one side/surface of a gel to fluid shear forces). In addition, the improved resistance to mechanical failure at the interface can aide in preventing gel detachment due to cell-mediated contractile forces, which can be especially prominent under pathological conditions required to model myriad fibrotic diseases.

Example 2: Harnessing Patterned Collagen Anchorage to Sculpt Microtissue Geometry Having confirmed the integrity of collagen anchorage to PDMS surfaces, FIG. 8 illustrates results of applying the above-described techniques to sculpt the form of microengineered tissue constructs. Such microengineered tissue constructs can be sculpted by fabricating circular PDMS wells with patterns of between 1 and 5 evenly spaced anchoring nodes that provide increased local surface area of collagen anchorage in those areas of the gel boundary, as shown in FIG. 8. By incorporating contractile cells, 3T3 mouse embryonic fibroblasts can selectively detach the collagen gel from the PDMS surfaces between anchoring nodes due to decreased local surface area of anchorage, creating a tissue construct with axial connections between neighboring nodes and a predictable resultant geometry (e.g., linear for 2-node, triangular for 3-node, etc). This approach can provide a novel paradigm for tuning cell-mediated sculpting of collagen gel-based microtissue constructs.

Figure 8A:
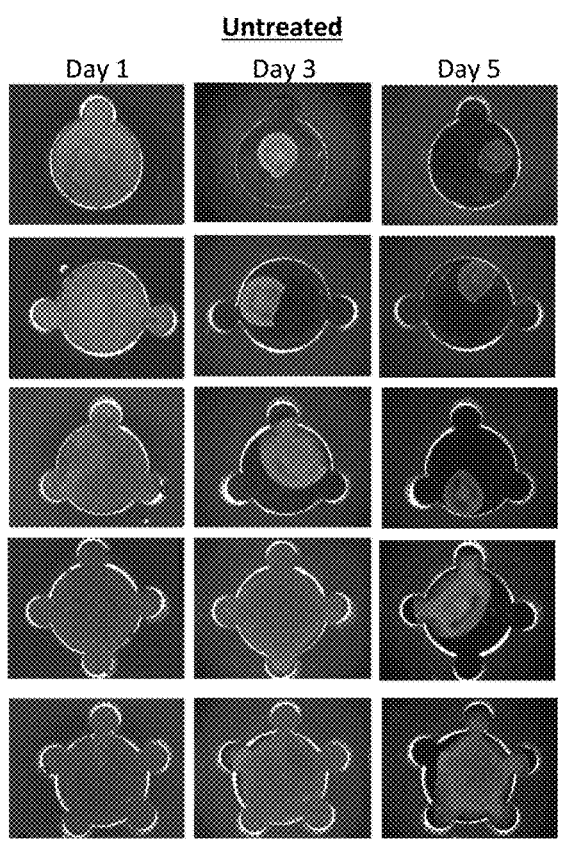
FIGS. 8A and 8B are photographs depicting the time course of patterned microtissue sculpting by embryonic mouse fibroblasts in multiple geometries.
Figure 8B:
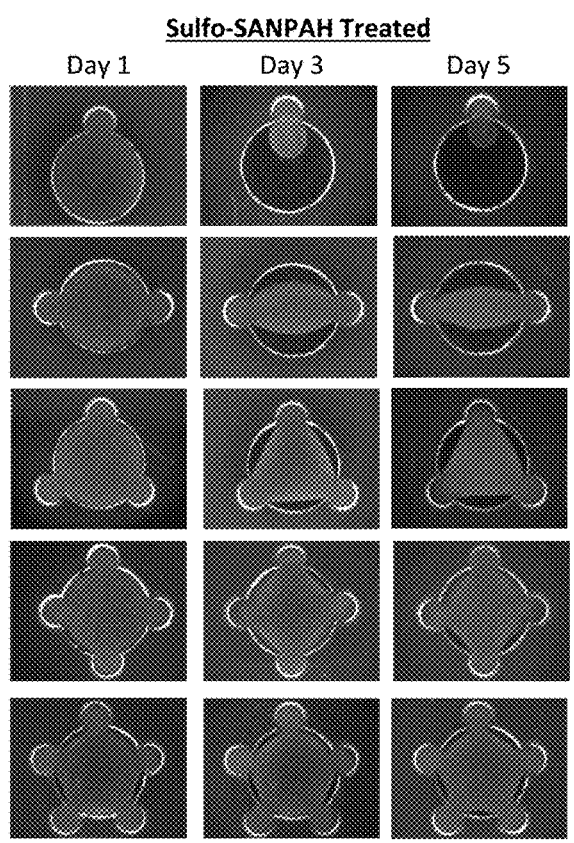

FIGS. 8A and 8B are photographs depicting the time course of patterned microtissue sculpting by embryonic mouse fibroblasts in multiple geometries. FIGS. 8A and 8B demonstrate that rationally designed geometries can be engineered via cell force-mediated gel sculpting. In certain embodiments, increasing the number of anchoring nodes delayed bulk gel detachment in untreated PDMS surfaces. However, detachment from nodes and intervening boundaries was observed by day 5 for all designs tested (FIGS. 8A and 8B). By comparison, no gel detachment from anchoring node surfaces was observed in the SS-treated group for all designs tested. For the single node design, by day 5 gel was observed to be only attached to the nodal surface, with the remainder of the gel boundary completely detached and contracted to a small fraction of the original area/volume (FIGS. 8A & 8B, top row). As illustrated in FIGS. 8A and 8B, the 2-node design can result in the formation of an aligned/linear construct, while the 3-, 4- and 5-node designs can produce triangular, diamond-shaped and pentagonal constructs, respectively. By introducing nodes of increased local surface area for anchorage that had been treated with sulfo-SANPAH, locations of gel detachment were able to be controlled in a predictable fashion, thereby using contractile stromal cells as a microengineering tool to sculpt defined microtissue construct geometries. This platform can also be used to sculpt aligned connective microtissues using human fibroblasts.

Figure 9:
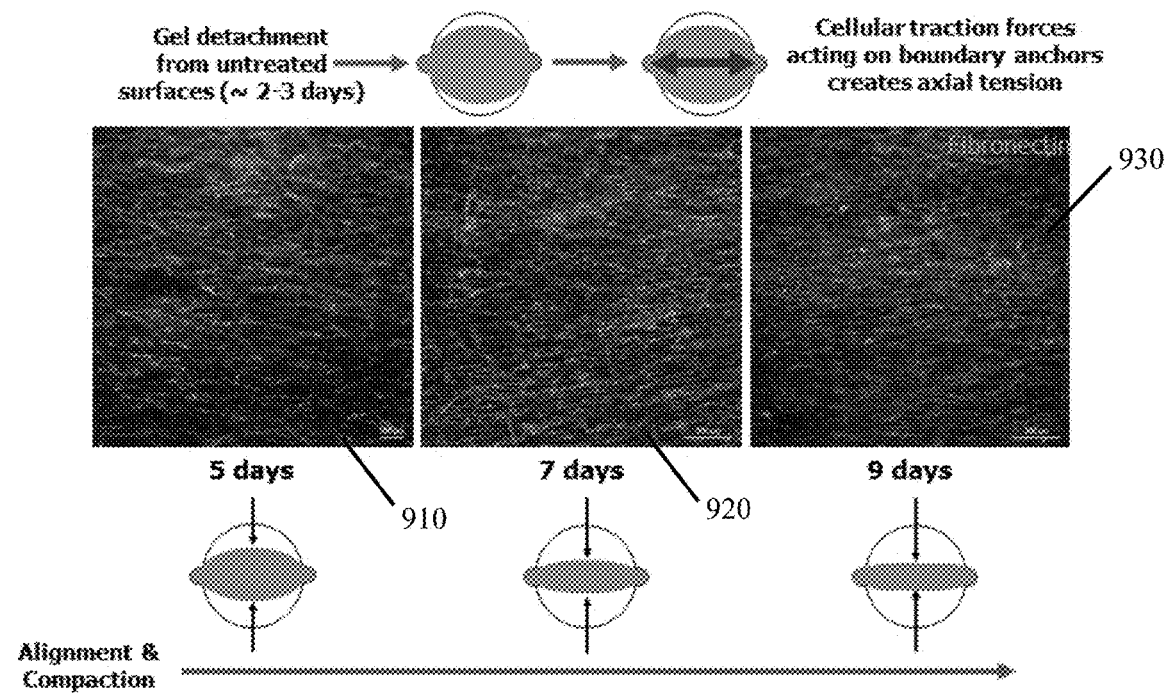
FIG. 9 illustrates results of the experiment in which connective tissue microtissue was sculpted using human fibroblasts.

During tendon development, bone and muscle elongation can progressively load tendons axially, parallel to the direction of tendon insertion, promoting cell elongation and/or alignment and increased production of ECM. Similarly, experiments in chick embryos demonstrate that tendons fail to develop in immobilized (e.g., mechanically isolated)

tibiofemoral and tibiotarsal joints, demonstrating the requirement of constant load from bone and muscle elongation in tendon organization. Using highly contractile human lung fibroblasts, axial boundary constraints in the two-node design can focus cellular traction forces, promoting fibroblast alignment, increased ECM synthesis and parallel alignment of newly deposited ECM. Computational models developed for studying cell and ECM alignment and contraction based on cell-generated traction forces can be used to simulate the time course of construct morphogenesis, as shown in FIG. 2C. Corroborating modeling simulations, detachment from untreated surfaces occurred by 2-3 days of culture, with compaction and alignment along the central axis progressing over 9-11 days in culture, as shown in FIG. 9. FIG. 9 illustrates results of the experiment in which connective tissue microtissue was sculpted using human fibroblasts. These constructs can be stable for up to thirty days in culture depending on the cell type used and the serum concentration of the cell culture medium. Image 910 depicts the construct at 5 days, image 920 depicts the construct at 7 days, and image 930 depicts the construct at 9 days. As FIG. 9 illustrates, gel can detach from untreated surfaces within two to three days and cellular traction forces acting on the boundary anchors can create axial tension. FIG. 9 also illustrates that over time the alignment and compaction changes.

Figure 10A:
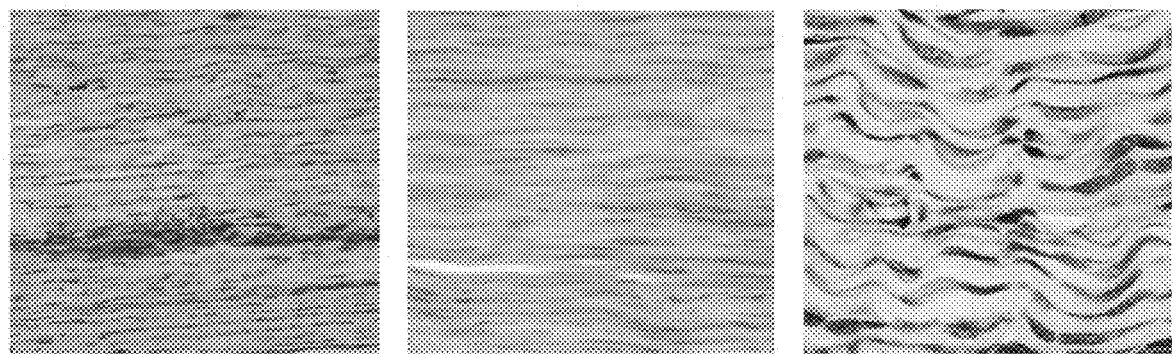

FIG. 10A illustrates exemplary images of dense regular connective tissue and FIG. 10B illustrates exemplary images of microengineered connective tissues that have been in vitro for nine to ten days. FIGS. 10A and 10B illustrate that microtissue organization resulting from autonomous cell-mediated collagen gel sculpting yields structures highly reminiscent of dense regular connective tissues in vivo.

FIG. 11 is a table illustrating orientation data for coherency and dominant direction of fibronectin and nuclei alignment. The dominant direction of 0 degrees indicates a horizontal alignment while a value of 45 degrees with low coherency indicates totally random orientation. Coherency (e.g., how similar the orientation is over the entire image) can have a value between 0 and 1, a value of 1 indicating identical orientation throughout. Such data illustrated in FIG. 11 provide quantification of cell and extracellular matrix alignment in the sculpted two node configuration vs. unpatterned tissues. The data shown in the table of FIG. 11 can demonstrate alignment in the two-node configuration, an example of the platform described by the disclosed subject matter.

Figure 12B:
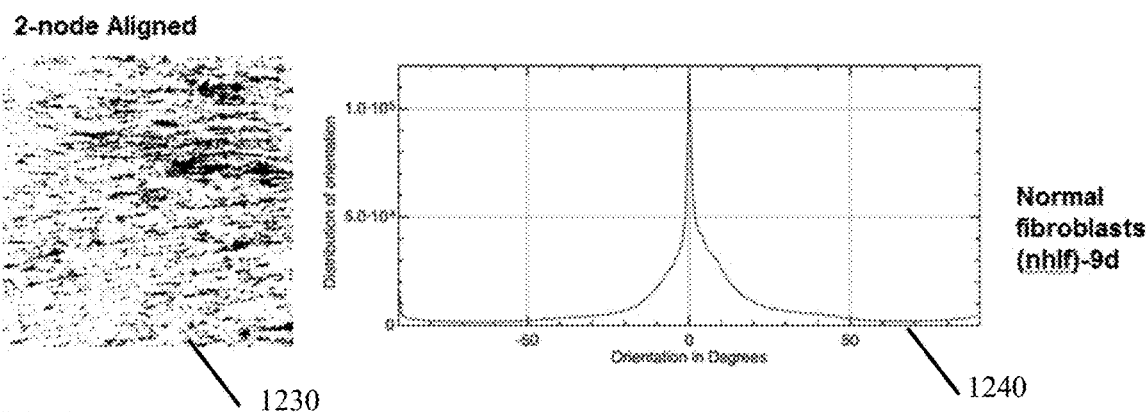

FIGS. 12A and 12B illustrate examples of cell nuclei orientation analysis for unpatterned and/or contracted samples (FIG. 12A) and for 2-node aligned samples (FIG. 12B). Photo 1210 illustrates an image of the unpatterned sample while graph 1220 illustrates a graph plotting the distribution of orientation against the orientation of the cell nuclei for unpatterned samples. Photo 1230 illustrates an image of the 2-node aligned sample while graph 1240 illustrates a graph plotting the distribution of orientation against the orientation of the cell nuclei for 2-node aligned samples.

Figure 13A:
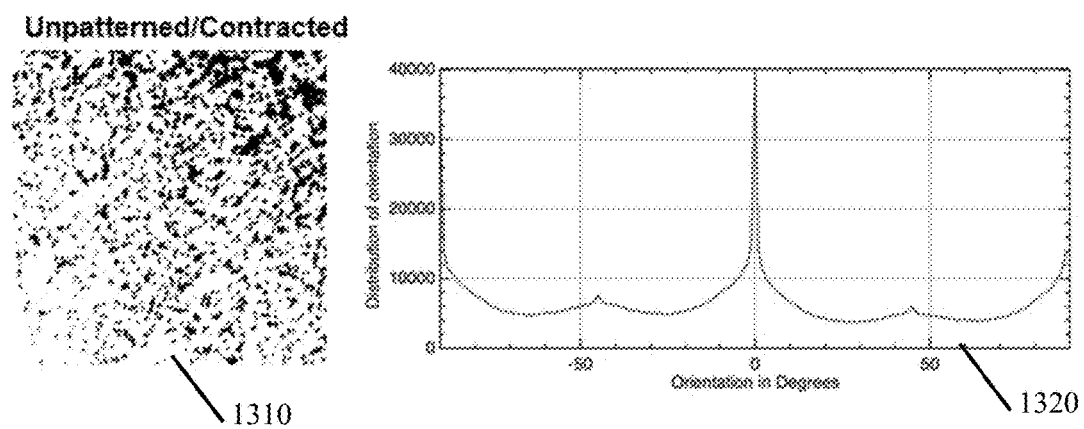
FIGS. 13A and 13B illustrate examples of fibronectin orientation analysis for unpatterned and/or contracted samples (FIG. 13A) and for 2-node aligned samples (FIG. 13B).
Figure 13B:
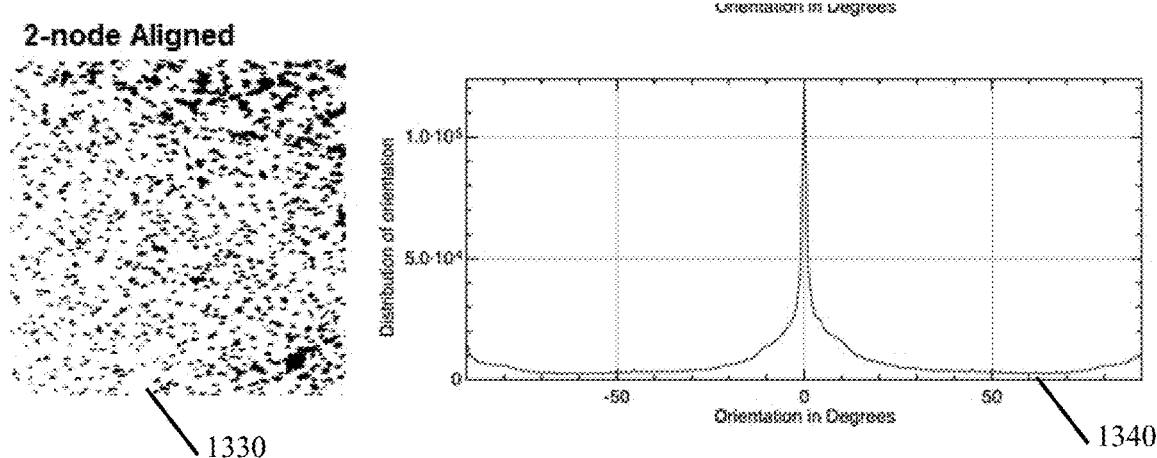

FIGS. 13A and 13B illustrate examples of fibronectin orientation analysis for unpatterned and/or contracted samples (FIG. 13A) and for 2-node aligned samples (FIG. 13B). Photo 1310 illustrates an image of the unpatterned sample while graph 1320 illustrates a graph plotting the distribution of orientation against the orientation of the fibronectin for unpatterned samples. Photo 1330 illustrates an image of the 2-node aligned sample while graph 1340 illustrates a graph plotting the distribution of orientation against the orientation of the fibronectin for 2-node aligned samples.

In certain embodiments, fibroblast and fibronectin alignment in the axial direction was accompanied by robust deposition of collagen type III, an integral fibrillar collagen in connective tissues that is not readily produced by fibroblasts in vitro. This can be of critical importance to connective tissue development and maturation.

FIGS. 14A and 14B illustrates parallel cellular cytoskeleton and ECM in sculpted 2-node connective microtissues. FIGS. 14A and 14B illustrate normal fibroblasts and 2-node samples that have been cultured for 9 days. The portions of these images marked in green depict cytoskeleton stained with smooth muscle actin antibody and the portions of these images marked in red depict ECM labeled with fibronectin antibody. FIGS. 14A and 14B show that the gel can be anchored and can be cultured for 9 days or longer durations without tearing off.

FIGS. 15A, 15B, and 15C illustrate images depicting sculpted connective tissue morphogenesis. FIG. 15A illustrates an unpatterned sample at 0 days. FIG. 15B illustrates a patterned sample at 5 days, and FIG. 15C illustrates a patterned sample at 9 days. As shown by FIGS. 15A, 15B, and 15C, sculpted connective tissue morphogenesis alone increases collagen type III production. Collagen type III production can be difficult to achieve in vitro. In certain embodiments, sculpted connective tissues can create a physiological environment that promotes collagen type III production and deposition, further illustrating the utility of the disclosed subject matter for engineering human connective tissues for a myriad of applications.

As shown in the previous examples for skeletal and connective tissues, the 2-node anchoring configuration can result in a highly aligned tissue architecture characteristic of connective tissues such as tendons, ligaments and fascia, as well as muscle tissue and other examples. The integration of mesenchymal stem cells into healing and/or scarring tissue structures is an area of intense research interest, both in the context of regenerative medicine and fibrotic disease. The disclosed subject matter provides for integration of MSC into aligned tissues, where they can differentiate to acquire a more contractile and aligned morphology that is characteristic of their integration in the aforementioned tissue structures.

In certain embodiments, in addition to fibroblast cell and matrix alignment in response to mechanical loading (e.g., the response of differentiated cells to microenvironmental cues), the differentiation of human mesenchymal progenitor cells (e.g., cells that are isolated from specific tissues or derived from the bone marrow) to a contractile fibroblast phenotype can be examined in the context of connective tissue development and can also be relevant in adult wound healing and pathological fibrosis. To test the utility of the disclosed methods and systems for inducing differentiation of mesenchymal stem cells (MSCs), lung fibroblasts can be replaced with human MSC in the 2-node design. Directed cellular traction forces can drive MSC alignment and differentiation to a more contractile phenotype. MSC can be derived from healthy individuals and/or from patients with various diseases to create connective and musculoskeletal tissue disease models.

FIGS. 16A and 16B illustrate images depicting the SMA distribution for sculpted samples without any growth factors (16A) and plate-bound samples with growth factors (FIG. 16B). As can be observed by comparing FIGS. 16A and 16B, the dynamic mechanical environment during sculpting can drive a contractile phenotype (e.g., SMA) in MSC, even more potently than a static culture with growth factor-based approaches. However, the dynamic mechanical environment can drive the contractile phenotype in a more natural, autonomous fashion based on initial geometry and patterned boundary constraints than a static culture with growth factor-based approaches. In certain embodiments, such as the ones depicted in FIGS. 16A and 16B, efficient alignment and markedly increased numbers of SMA+ cells can be observed in aligned sculpted microtissues versus plate bound control tissues with amorphous geometry.

Figure 17A:
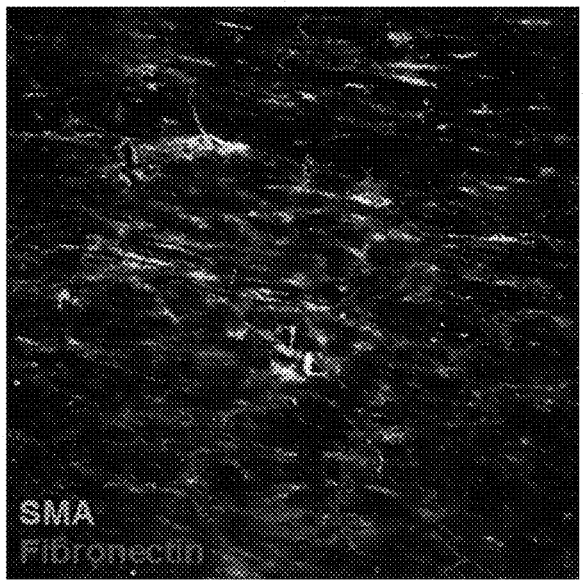
FIGS. 17A-17D are images that illustrate mesenchymal stem cell differentiation to a contractile phenotype in aligned microtissues.
Figure 17B:
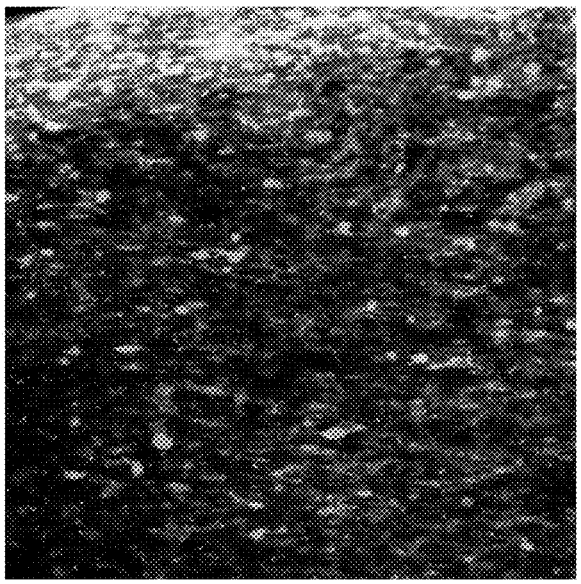
Figure 17C:
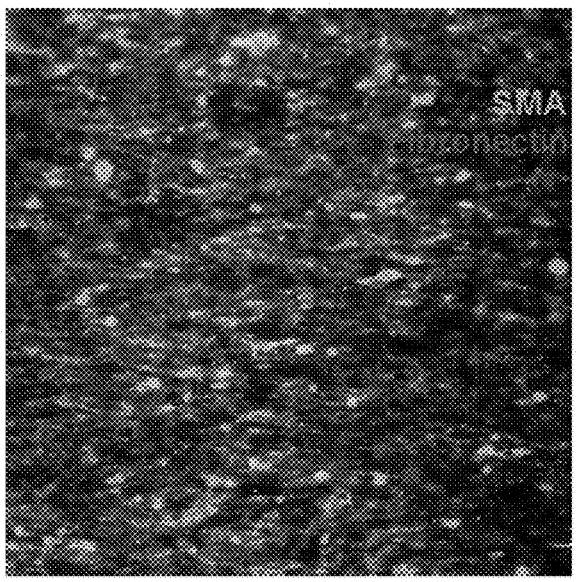
Figure 17D:
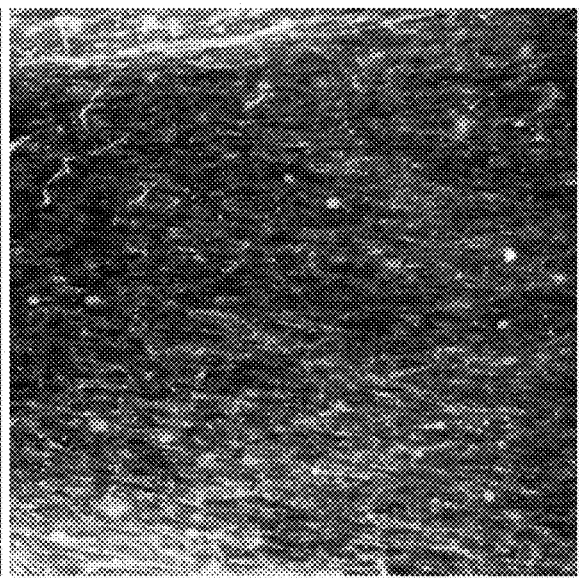

FIGS. 17A-17D are images that illustrate mesenchymal stem cell differentiation to a contractile phenotype in aligned microtissues. FIG. 17A illustrates MSC two-node samples at 6 days at the center of the construct and FIG. 17B illustrates MSC two-node samples at 6 days near the boundary. FIG. 17C illustrates MSC two-node samples at 11 days at the center of the construct and FIG. 17D illustrates MSC two-node samples at 11 days near the boundary. As shown in the previous examples for skeletal and connective tissues, the two-node anchoring configuration can result in a highly aligned tissue architecture characteristic of connective tissues such as tendons, ligaments and fascia, as well as muscle tissue and other examples. The disclosed methods and systems can provide for integration for MSC into aligned tissues, where they differentiate to acquire a more contractile and aligned morphology that is characteristic of their integration in the aforementioned tissue structures.

Due to the observed spatial heterogeneity of smooth muscle actin expression in differentiating MSC, with much lower levels of expression along the center region of constructs as shown in FIGS. 17A-D, cells along the detached boundaries can be determined to be the most active 'sculptors' (e.g., the most contractile cells primarily responsible for contracting the edges). In certain embodiments, increases in integrin expression can be a molecular output reflective of mechanosensitive, activated phenotypes in a myriad of cell types. In certain embodiments, increased alpha-5 integrin (fibronectin receptor) expression at construct boundaries can be a driving force of the increased abundance of SMA+ cells in these regions.

Figure 18:
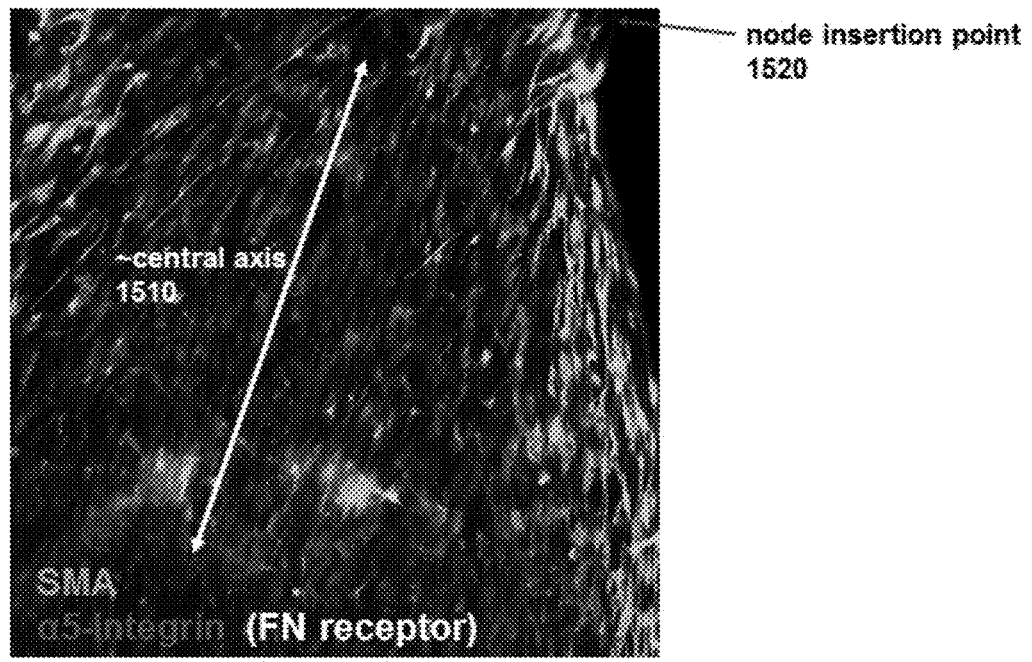
FIG. 18 is an image illustrating fibronectin receptor phenotypes of MSC-derived 'sculpting cells' on construct boundaries near a node insertion point.

FIG. 18 is an image illustrating fibronectin receptor (e.g., SMA+/α5-integrin+) phenotypes of MSC-derived 'sculpting cells' on construct boundaries near a node insertion point. FIG. 18 illustrates the construct at 3 days total, approximately 24 hours after the construct has fully detached from the un-treated side walls, during early compaction and alignment. As expected based on the observed contraction behavior, several layers of MSC along the tissue border can co-express high levels of SMA and alpha-5 integrin, suggestive of the aforementioned mechanosensitive, highly contractile phenotype. In certain embodiments, mechanical cues during compaction and alignment can instruct mesenchymal stem cells to adopt a contractile (e.g., SMA) and adhesive (e.g., alpha-5) phenotype required to generate traction forces and sculpt the tissue. Based on the SMA staining for later time points shown previously, expression of SMA can progress inward from construct boundaries due to the buildup of tension making its way to the central axis as the compaction progresses. For example, by 9-11 days, SMA cells can be more evenly distributed, but at ~3 days they can be restricted mostly to the boundaries.

In certain embodiments, in order to expand upon the paradigm of cell-mediated microtissue sculpting in a more application-specific context, the two-node design can be utilized to generate an aligned skeletal myotube construct. Using the C2C12 myoblast cell line, a formation of aligned microtissue constructs can be observed having a cellular architecture and ECM ultrastructure reminiscent of skeletal myotubes as illustrated in FIGS. 19A, 19B, 20A, 20B, 21A, and 21B.

Figure 19A:
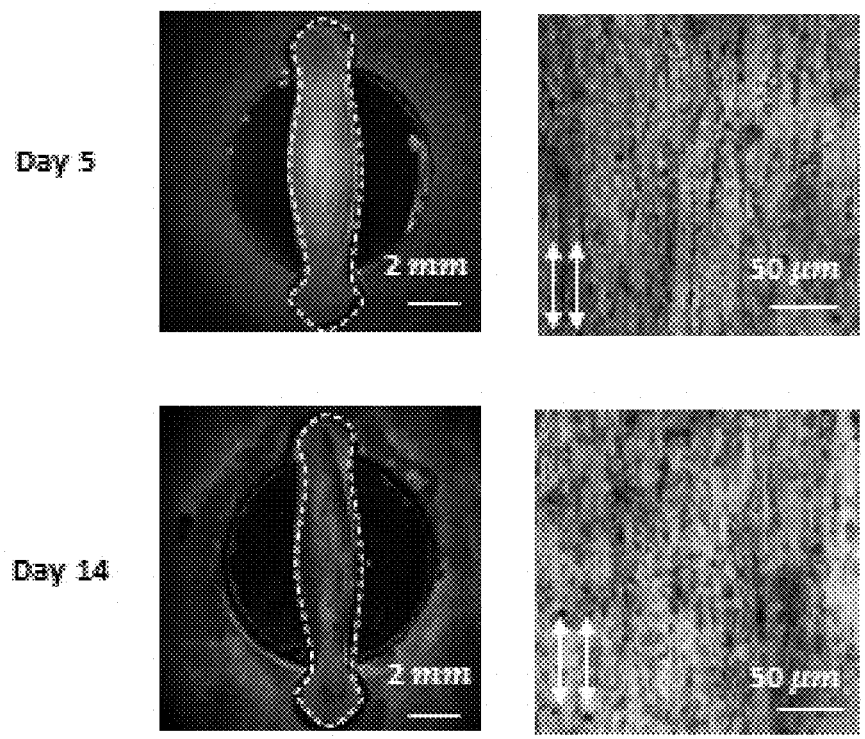
FIGS. 19A and 19B are images illustrating collagen skeletal muscle-like microtissues sculpted in sulfo-SANPAH treated PDMS devices.]
Figure 19B:
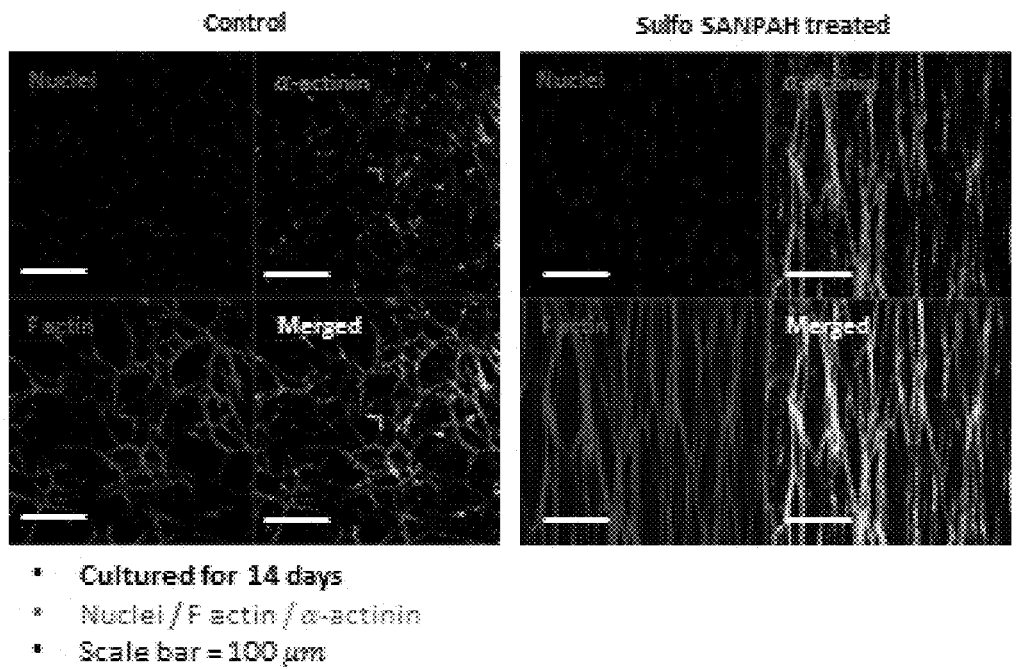

FIGS. 19A and 19B illustrate collagen skeletal muscle-like microtissues sculpted in sulfo-SANPAH treated PDMS devices. In particular, FIGS. 19A and 19B illustrate myotube differentiation and/or maturation as the sulfo-SANPAH treated PDMS devices were monitored over 2 weeks. As illustrated in FIGS. 19A and 19B, some of samples were immunestained to investigate intracellular cellular behavior, specifically α-actinin expression. As illustrated in FIGS. 19A and 19B, in control samples, complete gel detachment and contraction were observed to a small volume by day 4, with embedded myoblasts exhibiting a randomly oriented stellate appearance, while the aligned microtissues in the SS-treated group were comprised of uniformly aligned C2C12 cells.

Figure 20A:
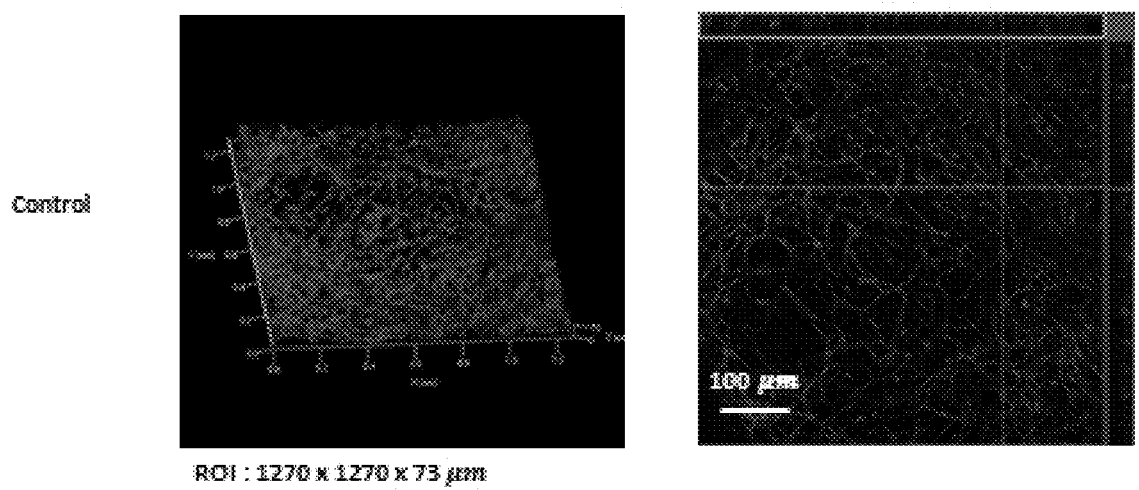

FIGS. 20A and 20B are Z-stack images generated from F-actin staining the control sample (FIG. 20A) and the sulfo-SANPAH treated sample (FIG. 20B) that have been generated by confocal imaging and image processing the constructs. FIGS. 20A and 20B illustrate confocal imaging results that can be used to investigate the 3D morphology of cell and/or collagen complex.

FIGS. 21A and 21B illustrate microscopic images of C2C12/collagen cultured in sulfo-SANPAH treated PDMS over 30 days using phase contrast microscope and confocal microscope. FIG. 21B is zoomed in portion of the cut-section of FIG. 21A. As can be seen in FIGS. 21A and 21B, the sulfo-SANPAH treated PDMS surface can retain its binding characteristics, even in long term cell culture processes. FIGS. 21A and 21B exhibit its long term cell anchoring performance and confirm the binding stability of Sulfo SANPAH between collagen and PDMS.

In certain embodiments, organotypic alignment of skeletal myoblasts in the disclosed sculpted microtissues can promote differentiation toward a more mature myotube-like phenotype. For example, in the examples discussed above, C2C12 cells in aligned microtissues of varying thickness consistently expressed α-actinin, a marker of muscle cell differentiation, while randomly oriented C2C12 in control group constructs (e.g., completely detached from all PDMS surfaces) did not express α-actinin. With otherwise equivalent culture conditions, the muscle-like aligned geometry and resultant axial strains created by patterning of cell-mediated microtissue sculpting can induce α-actinin expression. Examining the ultrastructure of aligned skeletal muscle-like microtissues by SEM can confirm the presence of aligned extracellular fibers, as illustrated in FIGS. 20A and 20B. The presence of collagen fiber bundles from the original gel, as observed in FIGS. 20A and 20B can confirm that cell-mediated microtissue sculpting confers defined geometries from the macro (e.g., the whole construct) down to the micro (e.g., the cells and ECM) scale.

FIGS. 22-24 illustrate results for myogenic differentiation of MSCs. FIG. 22 illustrates an experiment timeline for myogenic differentiation. As illustrated in FIG. 22, over time, the percentage of serum decreases from 10% serum to 0.2% serum (e.g., over a time period of 18 days). At 9-11 days into the experiment, detachment from the anchor points can be observed if the serum is not reduced. At 18 days, experiment is stopped and samples are stained for the myogenic marker: Myosin Heavy Chain (MyHC). FIG. 23B illustrates results of the samples being stained with the Myosin Heavy Chain marker at 18 days. FIG. 23A illustrates the myotube and FIG. 23C illustrates the multi-nucleated myotube.

Figure 24A:
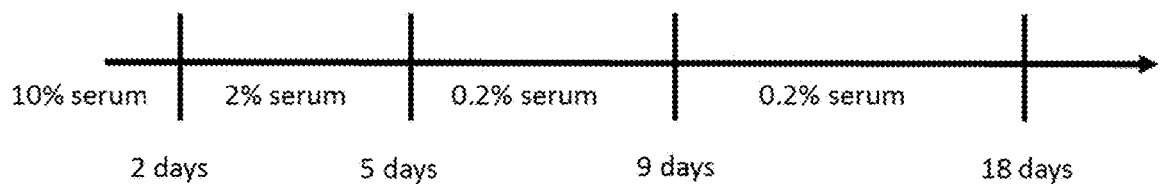
FIG. 24A-24C illustrate results for myogenic differentiation without exogenous stimulating factors.
Figure 24B:
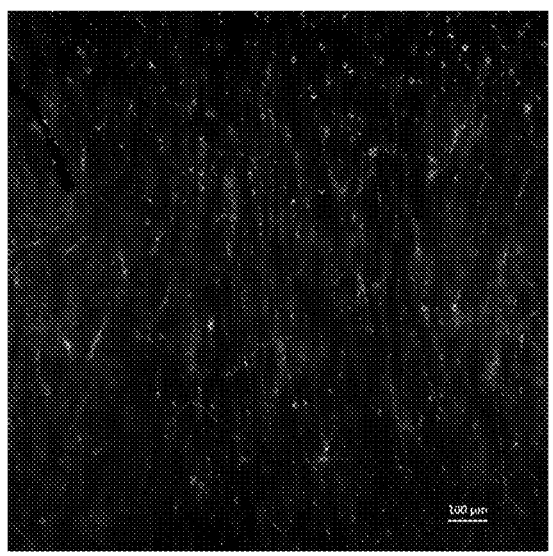
Figure 24C:
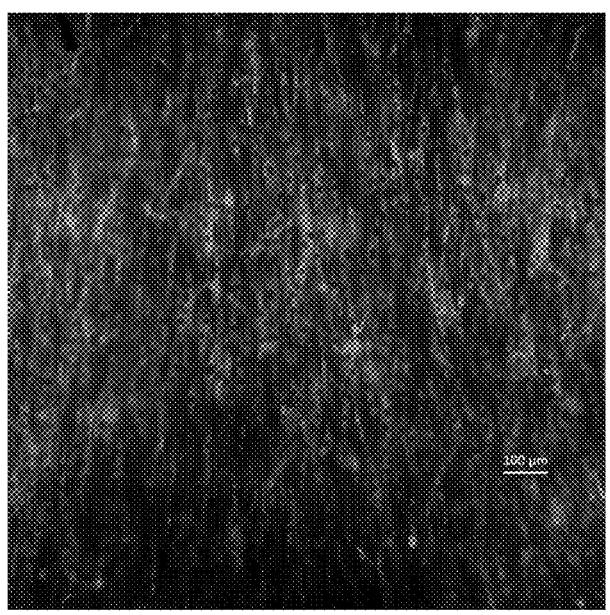

FIG. 24A-24C illustrate results for myogenic differentiation without exogenous stimulating factors. As the timeline (FIG. 24A) illustrates, myogenic differentiation without exogenous stimulating factors requires extended culture and is ongoing with 18 days. Longer culture periods can lead to further maturation. Comparing the results observed at 9 days (FIG. 24B) and at 18 days (FIG. 24C), it can be observed that increase in the level of green fluorescence from 9 to 18 days indicates myogenic differentiation.

In certain embodiments, the microengineering of the pattern of collagen gel anchorage to a PDMS substrate, cell-mediated contractile forces which have typically been viewed as an impediment to engineering tissues with predefined geometries, can actually be harnessed to sculpt desired shapes. The disclosed subject matter has extended and improved upon previous efforts aimed at modifying surface interactions with cells to apply similar technology toward engineered 3D microtissue architectures.

Example 3: Sculpting Perfusable Microfluidic Lumens in Microengineered Stromal Tissues The ability to generate a perfusable microfluidic lumen within a stromal microtissue can have a variety of applications, such as engineering direct, membrane-free endothelial-stromal or epithelial-stromal interfaces. Lumens within ECM gel-filled microchannels have been reported using methods such as needle withdrawal and on a larger scale using sacrificial materials such as water-soluble printed polysaccharides. The presently disclosed subject matter provides a system in which three walls of a rectangular microchannel can be sulfo-SANPAH treated. Selective cell-mediated detachment of the untreated wall can be allowed, which can result in the formation of a longitudinal, perfusable channel within the gel.

Figure 25A:
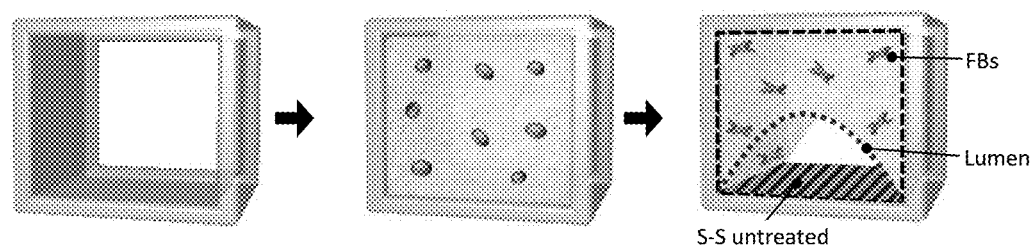
FIG. 25A-25D illustrate the method (FIG. 25A) for fabricating perfusable sculpted lumens and measurement images of the lumen (FIGS. 25B-D).
Figure 25B:
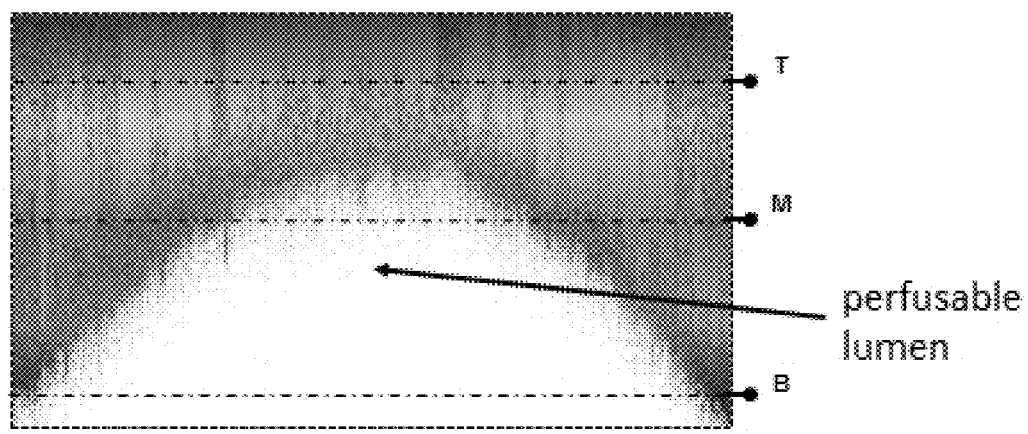
Figure 25C:
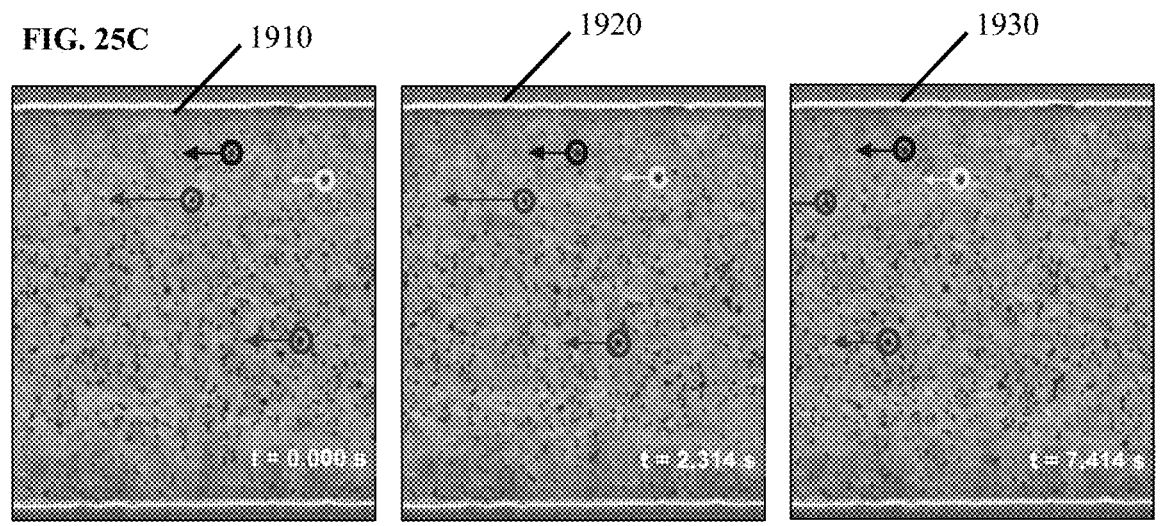
Figure 25D:
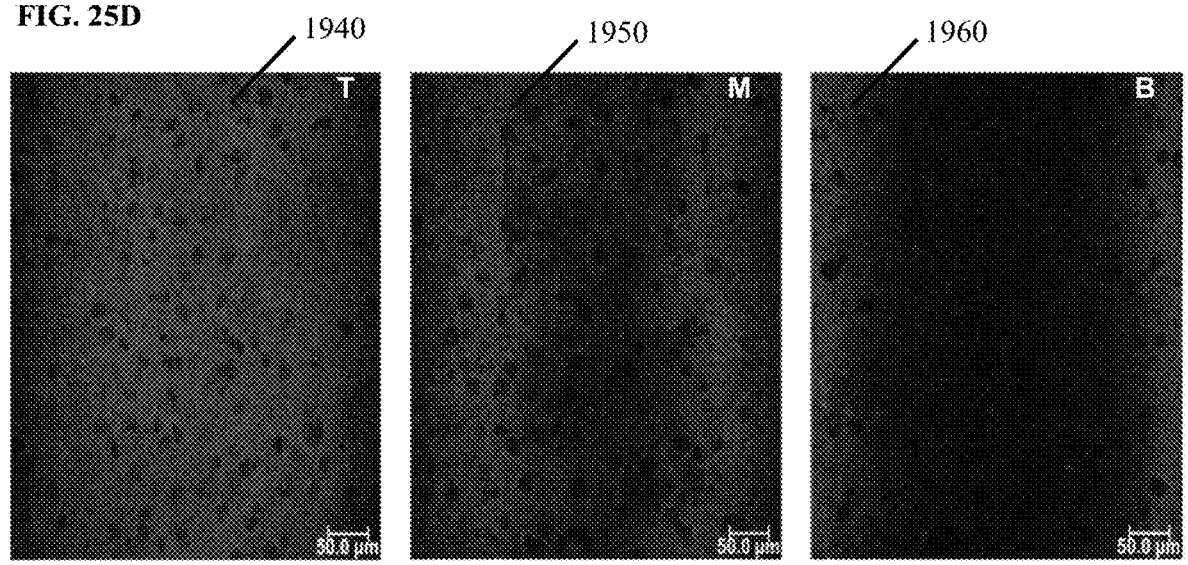

FIG. 25A-25D illustrate the method for fabricating perfusable sculpted lumens (FIG. 25A) and measurement images of the lumen (FIGS. 25B-D).

In certain embodiments, the SS method of gel anchoring can be leveraged to sculpt tissue geometries within the spatially constrained environment of a PDMS microchannel. Filling microchannels with a cell and gel mixture can require interfacing with a parallel "feeding channel" via a porous membrane. However, by using the SS-mediated collagen anchoring approach, a perfusable lumen space within the gel itself can be created by harnessing the sculpting phenomena. Three out of the 4 walls of a PDMS channel can be treated with sulfo-SANPAH according to the embodiments above, allowing the cells to detach the gel from the untreated surface, which upon contraction results in the formation of perfusable semi-circular lumen between the gel and the untreated PDMS surface.

In certain embodiments, stromal microtissues can be generated using 3T3 cells to fill the entire volume of a rectangular microchannel, where only three of the four channel walls had been treated with sulfo-SANPAH. Following 72 hours of culture, gel detachment can be observed from the untreated wall only, resulting in the formation of a semi-circular lumen, as illustrated in FIG. 25B. This lumen can be visualized in cross-sectional planes of 3D z-projections in samples labeled with anti-collagen I antibody, staining collagen fibers, and DAPI, which stained fibroblast cell nuclei, as seen in FIG. 22B.

FIG. 25C illustrates microscopy images 1910, 1920, and 1930 depicting directional changes of five different microspheres introduced into the microfluidic lumen. In the certain embodiment illustrated in FIG. 25C, the functionality of cell-sculpted lumens for perfusion applications can be determined by tracking the position of microspheres suspended in cell culture medium introduced to the cell-sculpted microfluidic lumen. In three sequential time-lapsed images 1910, 1920, and 1930, which were still frames captured from a video file, directional changes of five different spheres were tracked, as illustrated in FIG. 25C, confirming free movement of the microspheres with the bulk fluid through the lumen space. This functional demonstration that the cell-sculpted lumen is perfusable can indicate the utility of the lumen as a conduit to deliver nutrients and oxygen to cells embedded in the collagen gel within the confined geometry of a microfluidic device. This lumen sculpting technique can be used to engineer stromal interfaces with an epithelium or endothelium without the use of an intervening membrane, which is commonly employed in organ-on-a-chip microsystems. To engineer such stromal interfaces, a second cells of a desired cell type can be injected into the lumen space subsequent to its cell-mediated formation. The cells can then adhere to the ECM hydrogel surface, creating a direct tissue-tissue interface.

FIG. 25D illustrates top-down images in three different focal planes (e.g., top (T) 1940, middle (M) 1950, and bottom (B) 1960) to illustrate that collagen fibers and cells can uniformly fill the space near the top plane and cover half of the space, leaving the center portion empty. Additionally, FIG. 25D illustrates that in the bottom-most plane, the fibers and cells can cover only the narrow side edges.

Lung Disease Models

The following examples relate to microengineered biomimetic lung models that can use the disclosed methods to provide for stable tethering and long-term maintenance of 3D tissue constructs in the biomimetic lung models. Sulfo SANPAH treatment of the entire surface of the gel compartment of the biomimetic lung model can anchor the original geometry of the 3D tissue constructs in the biomimetic lung model. By harnessing cell-mediated traction, the 3D tissue constructs of biomimetic lung models can be shaped. For example, the geometry and microarchitecture of 3D collagen hydrogels and living tissues can be shaped in vitro by harnessing cell-mediated contractile forces described above. The following examples are offered to more fully illustrate the disclosure, but are not to be construed as limiting the scope thereof.

Example 4: Smoking-Induced Disease Model of a Human Small Airway

Figure 26:
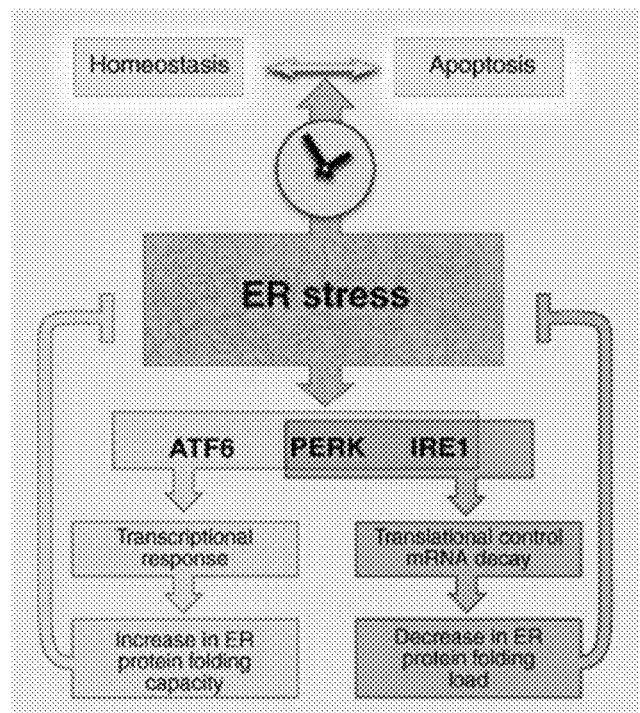
FIG. 26 depicts a schematic of Unfolded Protein Response (UPR) stress response.

Cigarette smoking-induced pathology involves induction of cellular stress responses in the epithelial cells lining the airways of human lungs, including activation of endoplasmic reticulum (ER) stress responses which result from the cell's inability to cope with its protein production demands. Acute smoke exposure causes oxidative stress, a consequence of which is disrupted proteostasis. Cells have evolved various mechanisms for coping with disrupted proteostasis, one of which is the Unfolded Protein Response (UPR) (FIG. 26). Stress tolerance leads to the return to homeostasis (proteostasis). Failure to restore homeostasis prompts a cell death program. Typically the apoptosis is immunologically silent; however, during heavy stress proinflammatory necrosis is prevalent. Thus, the cells either recover, or they don't and die, which is part of the beginning of the disease process that leads to chronic obstructive pulmonary disease (COPD), fibrosis or other lung diseases.

It has been shown that the UPR is activated in the lungs of smokers with COPD (Jorgensen et al., 2008; Kelsen et al., 2008) and in the lungs of laboratory animals after exposure to the smoke of a single cigarette (Kenche et al., 2013).

The body of the model was formed using soft lithography techniques, in which the PDMF mixture was poured over the mold, and the body was allowed to cure. The microchannels were etched into the body, with the dimensions of 1 mm×1 mm×1 mm.

In this example, non-diseased small airway epithelial cells from Lonza were used. These are from healthy people, human small airway cells. Fibronectin was applied to the membrane prior to seeding of the cells. A 2-8 million cells/ml density cell suspension was introduced to the channel and allowed to incubate under static conditions for 2-4 hours. After the period of attachment, flow was initiated to wash away unattached cells. After cell proliferation was allowed to occur for 1-3 days, the medium was removed to initiate air-liquid interface culture.

Figure 27:
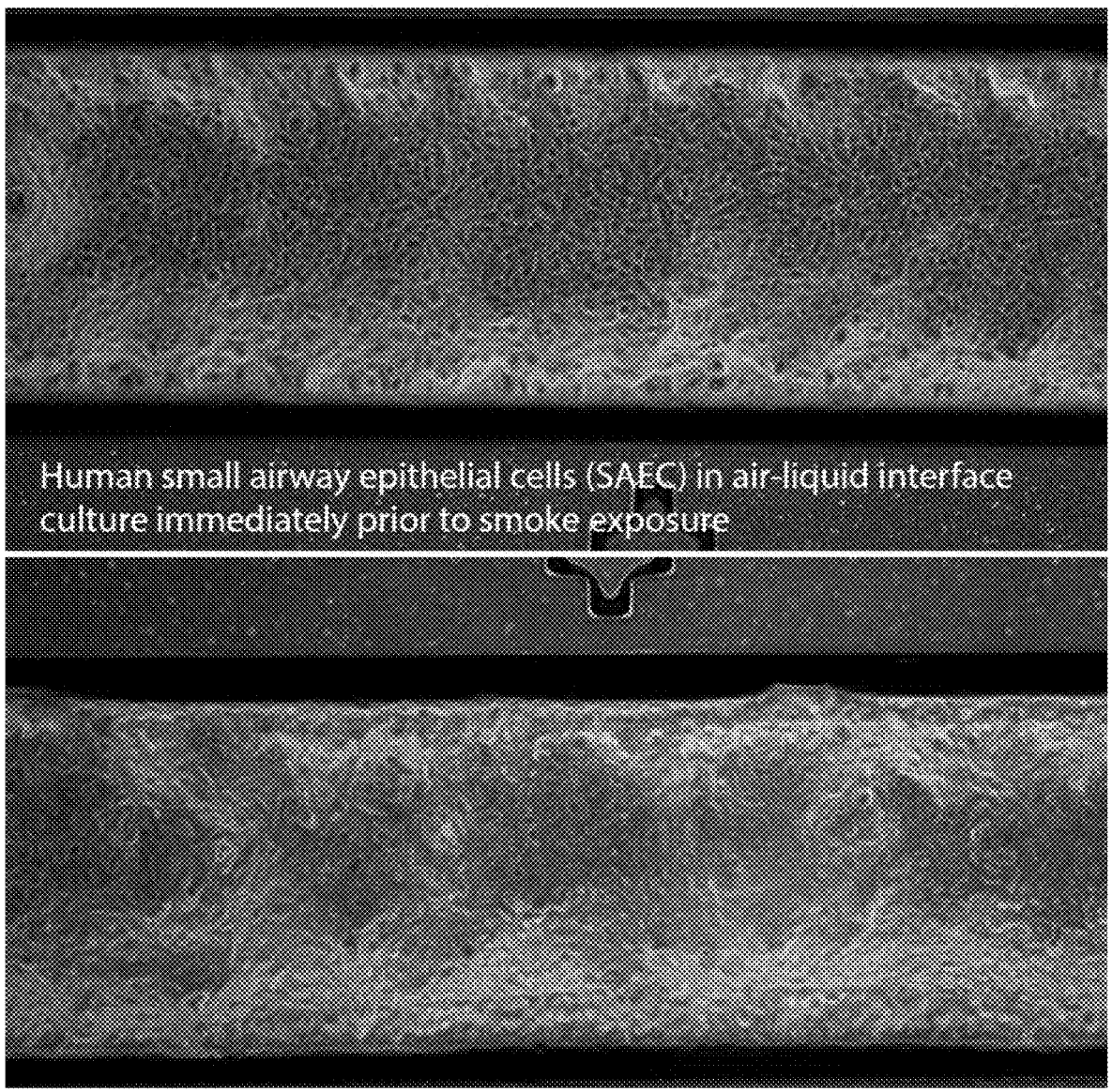
FIG. 27 depicts the cellular physiology of the biomimetic model before the exposure to an agent.

The device delivering the cell culture medium to the microchannels was disconnected from the body of the model before smoke was delivered to the microchannel above the membrane. Cell culture media remained in the lower microchannel to nourish the cells. A picture of the membrane was taken and shown in FIG. 27.

A lit cigarette was placed into a chamber to allow the smoke to accumulate. The air with smoke was channeled over the cells by pulling the smoke from the chamber through the upper microchannel of the model via a syringe device attached to the body of the model via a connecting tube.

UPR activation was measured by examining biomarkers ATF6 and EIF2a via immunohistochemistry and fluorescence microscopy.

Figure 28:
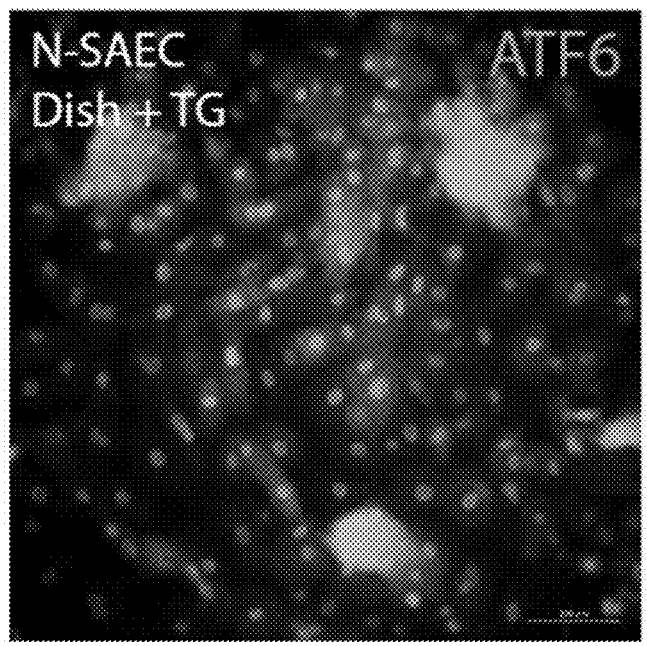
FIG. 28 depicts UPR induction via the staining of AFT6.
Figure 29:
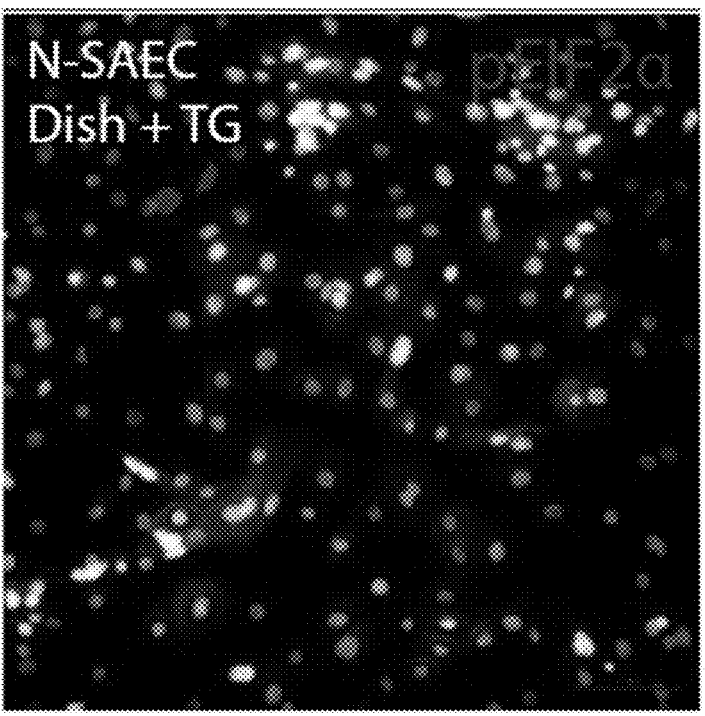
FIG. 29 depicts UPR induction via the staining of phosphorylated EIF2a (pEIF2a).

Up-regulation and nuclear translocation of ATF6 was observed (FIG. 28). Phosphorylation of EIF2a was also observed (FIG. 29) following exposure to smoke for approximately 2-3 minutes.

Figure 30A:
FIG. 30A-30B depict UPR induction via staining of AFT6 and pEIF2a in (FIG. 30A) control/air treated cells and (FIG. 30B) smoke exposed cells.
Figure 30B:
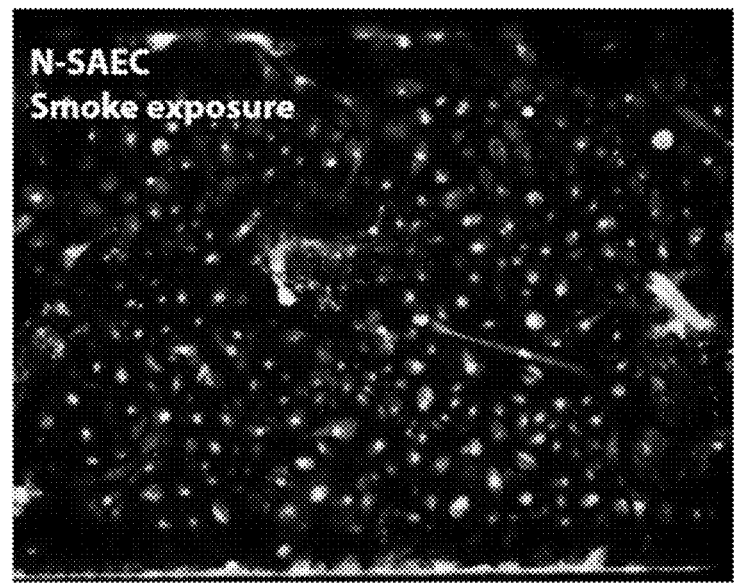

FIGS. 30A-30B depicts UPR induction via staining of AFT6 and pEIF2a in (FIG. 30A) control/air treated cells and (FIG. 30B) smoke exposed cells.

Figure 31A:
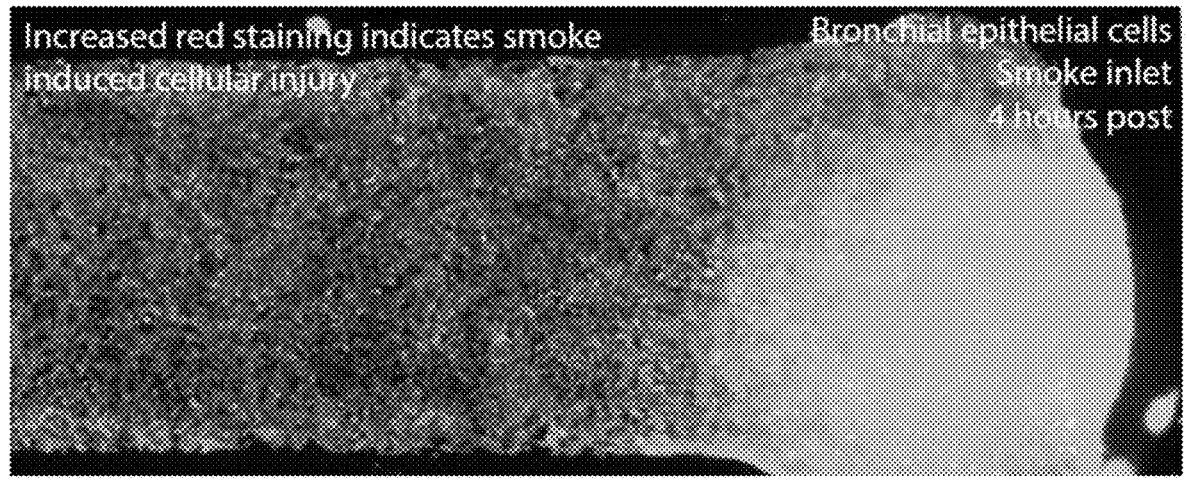
FIGS. 31A-31B depict cellular injury via staining of viable cells with calcein AM (green) and labeling of dead/dying cells with ethidium bromide (red) in (FIG. 31A) cells exposed to smoke for 4 hours and (FIG. 31B) cells exposed to air for 4 hours.
Figure 31B:
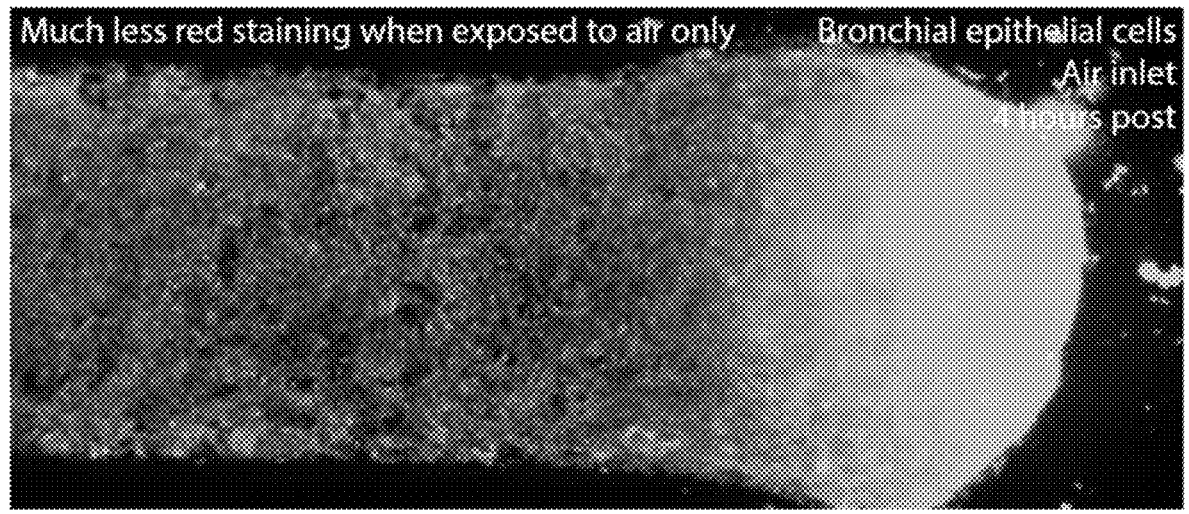

Even after exposure to tine amounts of cigarette smoke (fractions of individual puffs), an increase in UPR protein staining (AFT6 green, pEIF2a red) was induced (FIG. 31B).

After 4 hours of smoke exposure at a dilution ration of 1-10% an increase in cellular injury was observed (FIG. 31A) as compared to cells exposed only to air (FIG. 31 B).

Figure 32:
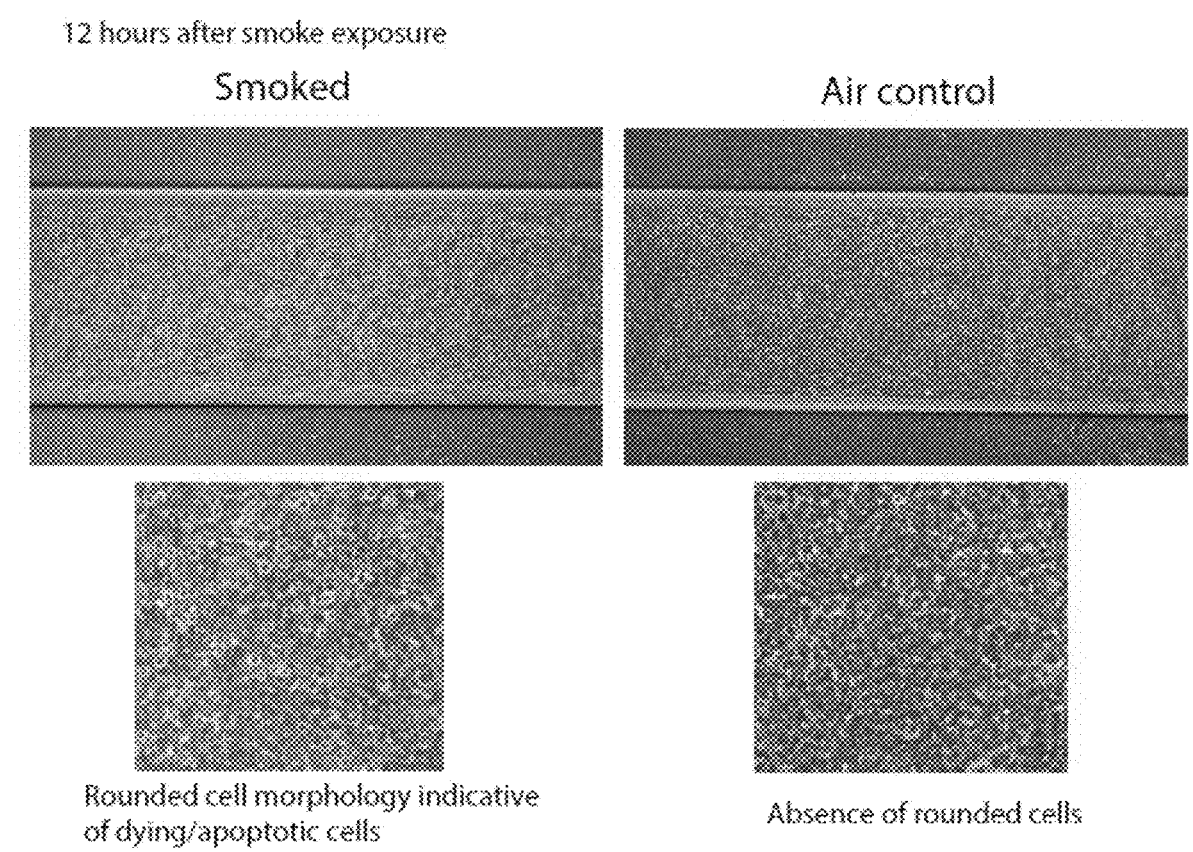
FIG. 32 depicts cell morphology in cells exposed to either air or smoke for 12 hours.

After 12 hours of smoke exposure at a dilution ration of 1-10% there was a dramatic change in the cellular morphology of the airway epithelial cells. In particular, a greater percentage of the cells were rounded, which indicated that the cells were undergoing apoptosis (FIG. 32).

Figure 33A:
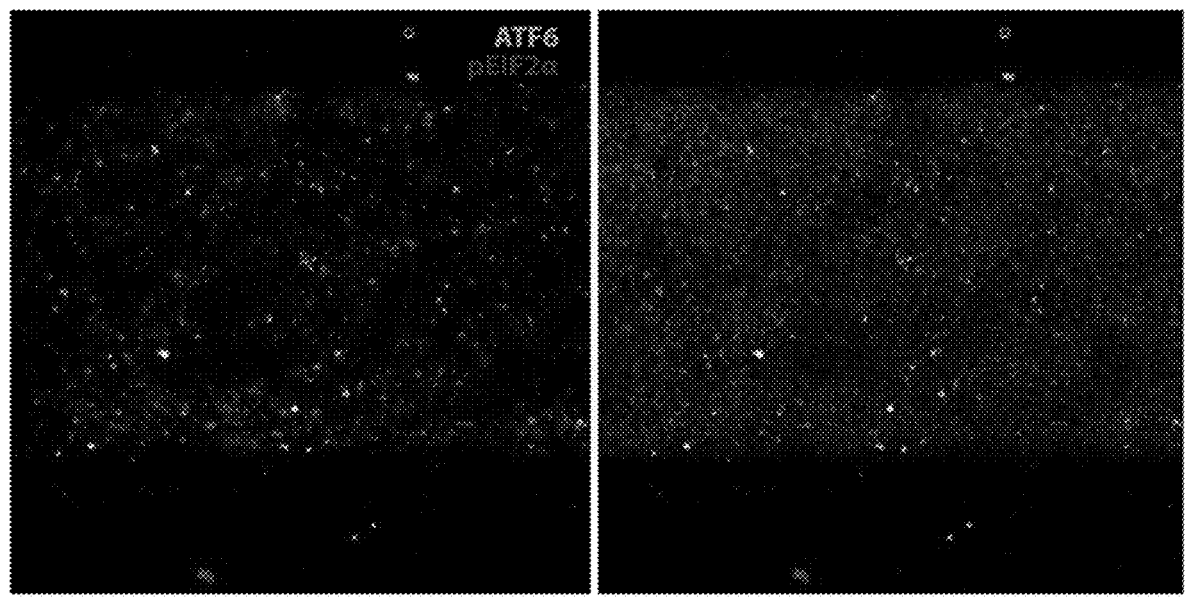
FIG. 33A-33B depict UPR induction via staining of AFT6 and pEIF2a in (FIG. 33A) cells exposed to air for 16 hours and (FIG. 33B) cells exposed to smoke for 16 hours.
Figure 33B:
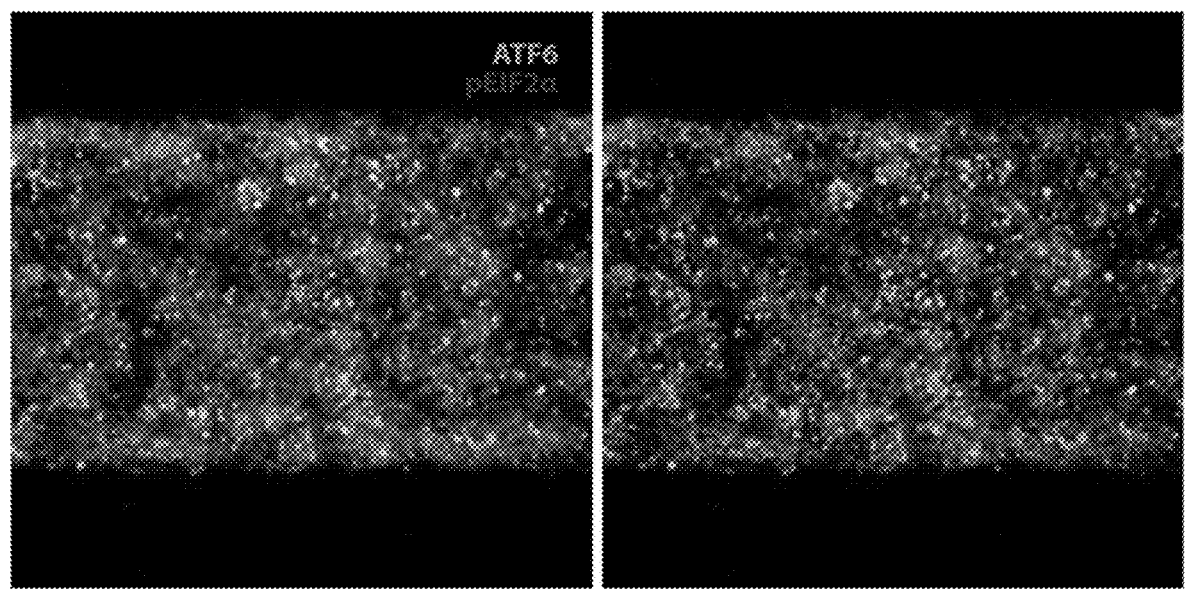

After 16 hours, very low levels of UPR activation (i.e., stress response) is seen in the control, air treated, cells (FIG. 33A). On the other hand, after 16 hours of exposure to smoke there was robust UPR activation in the exposed bronchial epithelial cells (FIG. 33B).

Single smoke exposure induced acute injury of human bronchial epithelial cells and small airway epithelial cells, leading to significant loss of epithelial integrity and barrier function. This injurious response was accompanied by increased stress in the endoplasmic reticulum, as manifested by robust activation of the unfolded protein response.

Example 5: COPD Disease Model

A biomimetic lung model was fabricated to mimic COPD in small airway cells. This model can be used to study modulation of the dysfunctional state in the epithelial cells, and to potentially discover/develop new therapeutics.

The body of the model was formed using soft lithography techniques, in which the PDMF mixture was poured over the mold, and the body was allowed to cure. The microchannels were etched into the body, with the dimensions of 1 mm×1 mm×1 mm.

Cells isolated from the lungs of smokers with COPD small airway cells were obtained from Lonza. A 2-8 million cells/ml density cell suspension was introduced to the channel and allowed to incubate under static conditions for 2-4 hours. After the period of attachment, flow was initiated to wash away unattached cells. After cell proliferation was allowed to occur for 1-3 days, the medium was removed to initiate air-liquid interface culture.

A lit cigarette was placed into a chamber to allow the smoke to accumulate. The air with smoke was channeled over the cells by pulling the smoke from the chamber through the upper microchannel of the model via a syringe device attached to the body of the model via a connecting tube.

Cells were stained for expression of ATF6 and pEIF2a, which are markers of the UPR response. They show high levels of activation in all conditions, which is indicative of their pathology. When smoked was delivered to the regular/normal airway cells, they started to express these same proteins found constitutively in the COPD cells.

Figure 34:
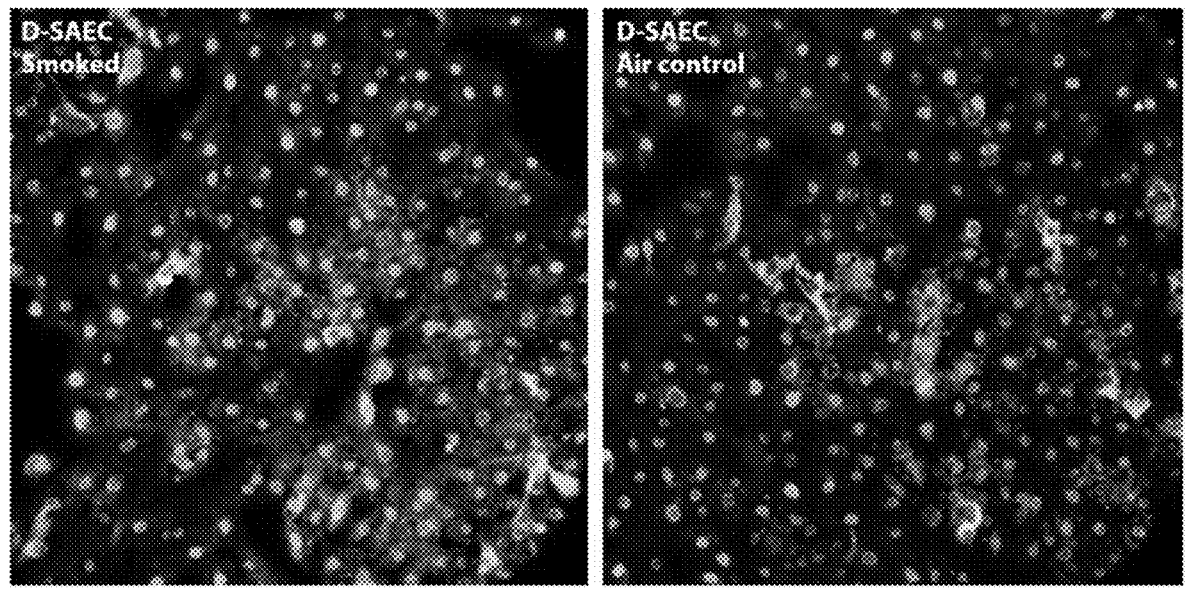
FIG. 34 depicts UPR induction via staining of AFT6 and pEIF2a in COPD cells exposed to smoke.

The cells were examined by immunohistochemistry and fluorescence microscopy. The similarity of the staining in both the control and the smoke exposed COPD cells demonstrated that the COPD cells have the disease characteristics regardless of in vitro smoke exposure (FIG. 34).

Figure 35:
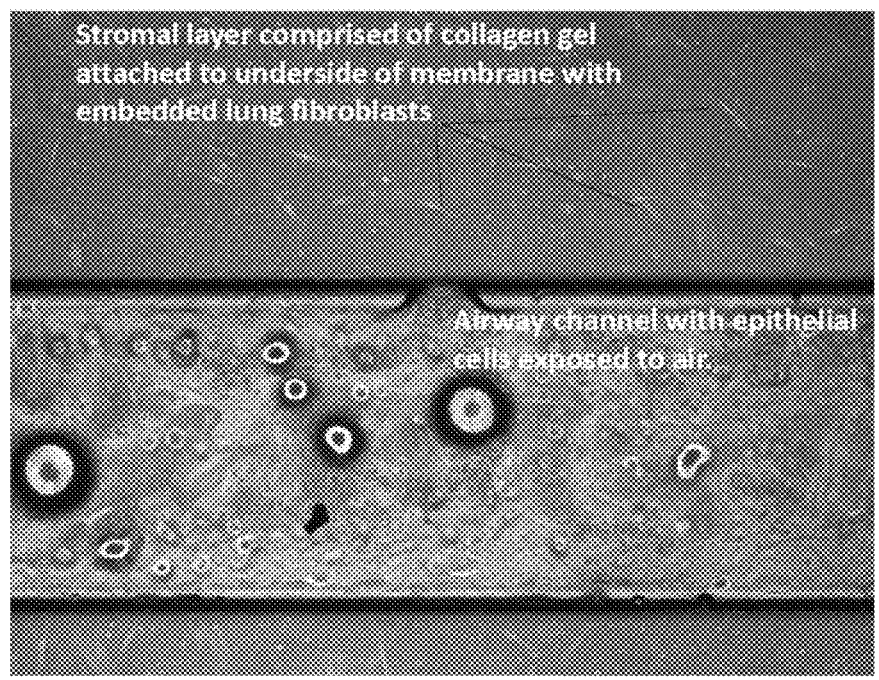
FIG. 35 depicts the cellular physiology of the biomimetic model according to certain embodiments, wherein the model incorporates the gel layer.

Example 6: Biomimetic Lung Model with Basal Stromal Tissue and Airway Lumen Macrophages A biomimetic lung model was fabricated to include both basal stromal tissue and airway lumen macrophages (FIG. 35).

The body of the model was formed using soft lithography techniques, in which the PDMF mixture was poured over the mold, and the body was allowed to cure. The microchannels were etched into the body, with the dimensions of 1 mm×1 mm×1 mm.

In this example, non-diseased small airway epithelial cells from Lonza were used. These are from healthy people, human small airway cells. A 2-8 million cells/ml density cell suspension was introduced to the channel and allowed to incubate under static conditions for 2-4 hours. After the period of attachment, flow was initiated to wash away unattached cells. After cell proliferation was allowed to occur for 1-3 days, the medium was removed to initiate air-liquid interface culture.

The gel was created by adding 1-8 mg of collagen to water, depending on the desired thickness, and the liquid gel was kept at 4° C. Instances when cells were added to the gel, they were added during this liquid phase. The membrane was treated with sulfo-sanpah to promote collagen/ECM anchorage. The gel was pipetted onto the underside of a membrane that had been stamped to the microchannel while the device was flipped upside down. Once the gel layer solidified by incubating at 37° C., the upper channel portion—now with a cast gel under the membrane—was flipped back over and placed over the reservoir layer to complete the device assembly.

The epithelial cells remained viable once the gel layer was attached to the underside of the membrane. In particular, FIG. 36 shows that after 72 hours after the attachment of the gel layer, the epithelial cells and stromal cells (fibroblasts) in the air-liquid interface remained viable. Viability studies were conducted with an alive/dead stain (calcein-AM and ethidium bromide) for simultaneous fluorescence staining of viable and dead cells.

Figure 37:
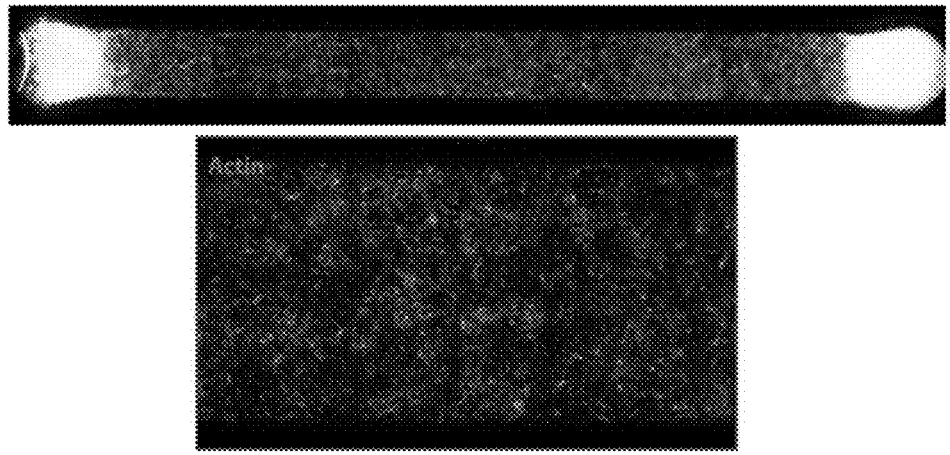
FIG. 37 depicts the incorporation of macrophages among the airway epithelial layer.

A THP-1 monocyte/macrophage cell line was also seeded onto the bronchial epithelial cell-lined channel. Staining with cell tracker die indicated that adherent/crawling macrophage-like cells were present on the surface of the airway epithelium, mimicking the multicellular complexity of the in vivo airway niche (FIG. 37).

Fibrosis Disease Models

The following examples related to organ models that are fabricated to mimic fibrosis. In certain embodiments, such models can be used to study modulation of the dysfunctional state in the fibroblasts and epithelial cells, and to potentially discover/develop new therapeutics. In such models, the epithelial cells can be seeded onto the first side of the membrane within the upper microchannel. Fibroblasts can be added to the gel layer prior to being cast and set upon the second side of the membrane as described above. Furthermore, the following examples are offered to more fully illustrate the disclosure, but are not to be construed as limiting the scope thereof.

Example 7: Five-Layer Organ Model

The first and second channel slabs and the chamber slab of the model were formed using soft lithography techniques, in which the PDMS mixture was poured over the mold, and the slabs were allowed to cure. The microchannels were etched into each of the channel slabs, with the dimensions of 10 mm×1 mm×0.15 mm (length×width×height). The chamber was etched into the chamber slab, with the dimensions of 6 mm×3 mm×1 mm (length×width×height). See FIG. 38 for a picture of the five-layer model.

Figure 38:
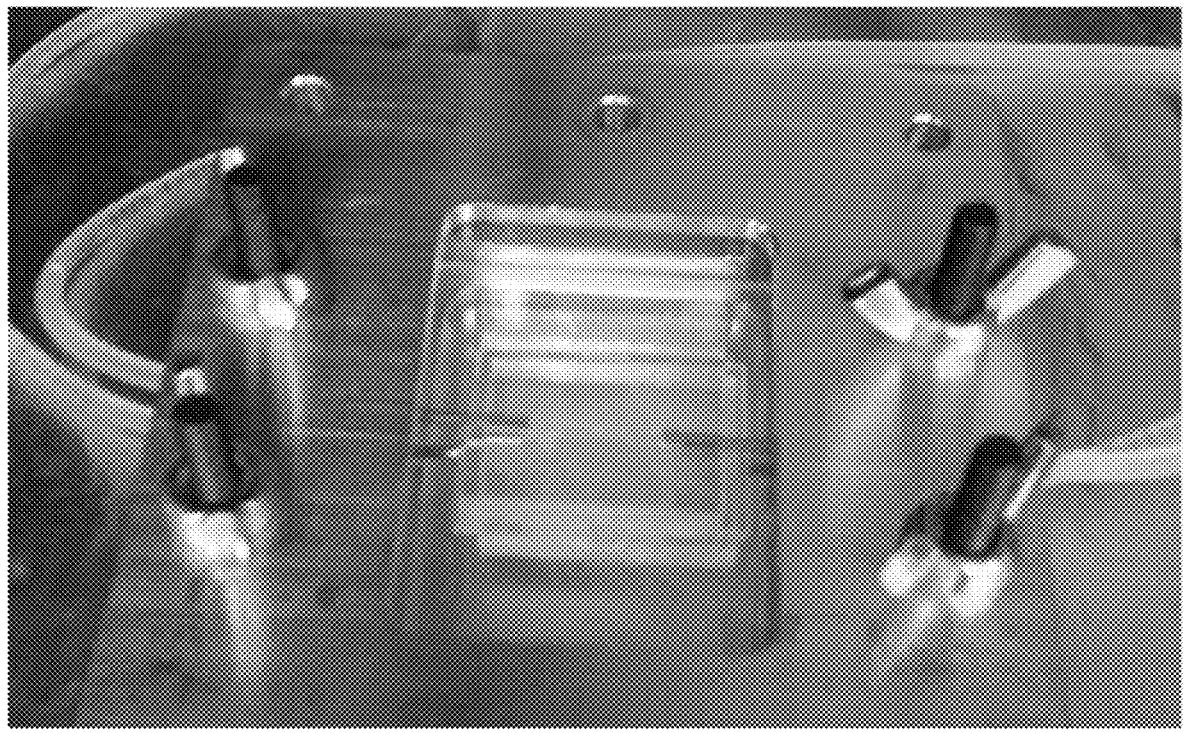
FIG. 38 depicts an exemplary clamp apparatus for mechanically bonding the different layers of the biomimetic organ model together.
Figure 39:
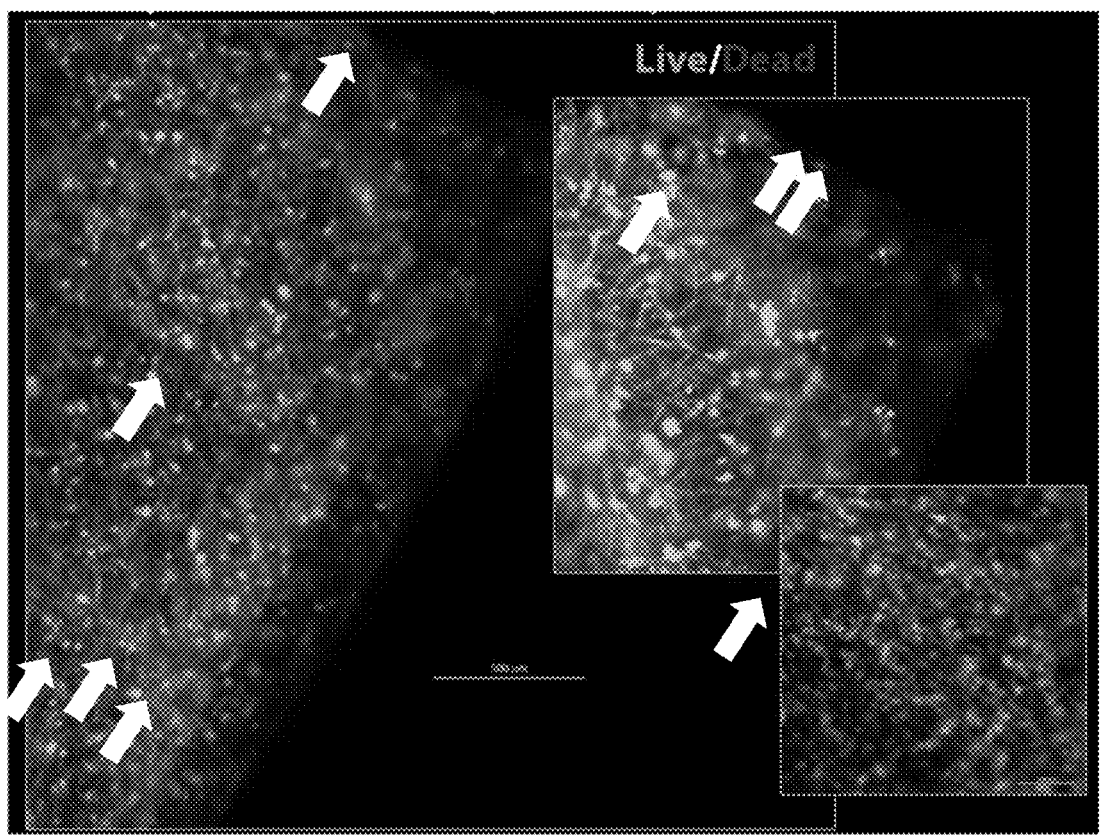
FIG. 39 depicts the cellular physiology of the stromal cells after 5 days in culture. The arrows denote dead cells.

In order to test whether the cells in the gel layer can be fed via the channels, one experiment was conducted with only cells in the gel layer (FIG. 39). In particular, human lung fibroblasts and THP-1 macrophage cells were included in the gel layer. The gel was created by adding collagen to physiological aqueous buffer. Additionally or alternatively, any aqueous buffer (e.g., phosphate buffered saline (PBS) buffer) can be used. The aqueous buffer can be kept at a concentration between 0.1 and 2 mg/ml and kept at 4° C. Human lung fibroblasts (100 K cells/ml) and THP-1 macrophage (50 K cells/ml) cells were added to the gel during the liquid phase. The side of the membranes facing the chamber slab (e.g. 242 and 251) were treated with sulfo-sanpah to promote collagen/ECM anchorage. The lower channel slab, lower membrane, and chamber slab were stacked. The gel was then pipetted into the chamber (e.g., 231). After the upper membrane and upper channel slab was placed on top, the biomimetic organ model was clamped and the biomimetic organ model was placed in the incubator at 37° C. A picture of the clamp apparatus is shown in FIG. 38. The biomimetic organ model was incubated for five days. For continuous perfusion of culture medium at 200 μL/hr in each channel, FGM-2 can be used as the medium having a reduced serum (e.g., between 0-2% and 2%). The stromal cells in the gel layer of the five-layer model exhibited greater than 99% viability (FIG. 39). Thus, it was demonstrated that the cells in the gel layer can be fed via the channels in the full five-layer assembly.

Figure 40:
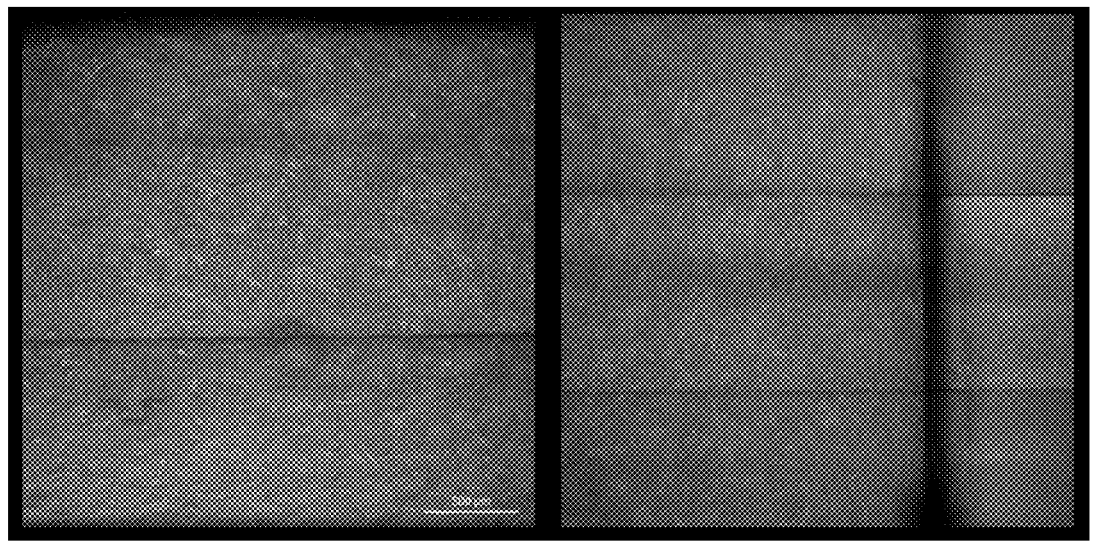
FIG. 40 depicts one embodiment of the cellular physiology of the cell-lined fluidic channels with the gel layer of the 5-layer model.

Next, the cellular physiology of the cell-lined fluidic channels with the gel layer of the five-layer model was examined (FIG. 40). In this instance, the upper channel contained human lung endothelial cells cultured with commercially available medium from the supplying vendor of the cells. The lower channel contained small airway epithelial cells with similar specific medium, both from same vendor. The gel was created by adding collagen to physiological aqueous buffer at a concentration of 2 mg/ml and kept at 4° C. Human lung fibroblasts (100 K cells/ml) were added to the gel during the liquid phase. The side of the membranes facing the chamber slab were treated with sulfo-sanpah to promote collagen/ECM anchorage. The lower channel slab, lower membrane, and chamber slab were stacked. The gel was then pipetted into the chamber. After the upper membrane and upper channel slab was placed on top, the biomimetic organ model was clamped. The endothelial and epithelial cells were then introduced via injection into the channel after presoaking with medium and ECM coating. FIG. 40 is a phase contrast image, taking during the culture period, depicting the interface between the gel and two membranes. The culture period, in this example, was 1 week. However, the culture period can have a longer duration (e.g., several weeks).

Example 8: Five-Layer Lung Fibrosis Model

This example presents a microengineered modular platform that leverages three-dimensional cell culture in a compartmentalized microdevice to replicate organ-specific alterations in the micromechanics of stromal tissue during fibrosis. This system combines tissue-engineered hydrogel constructs impregnated with human fibroblasts with perfusable microchannels to mimic the stromal-vascular and stromal-epithelial interface.

The ability to tune fibrotic responses using this model was demonstrated by varying the microenvironment to form a normal stroma consisting of quiescent human lung fibroblasts (HLFs) or to induce the development of fibrotic foci comprised of proliferating HLFs and a dense ECM. Furthermore, this example demonstrated the potential of this system for therapeutic screening by showing attenuated fibrotic responses via inhibition of integrin-mediated signaling known to promote organ fibrosis in vivo.

The first and second channel slabs and the chamber slab of the model was formed using soft lithography techniques, in which the PDMF mixture was poured over the mold, and the slabs were allowed to cure. The microchannels were etched into each of the channel slabs, with the dimensions of 10 mm×1 mm×0.15 mm (length×width×height). The chamber was etched into the chamber slab, with the dimensions of 6 mm×3 mm×1 mm (length×width×height).

Figure 41:
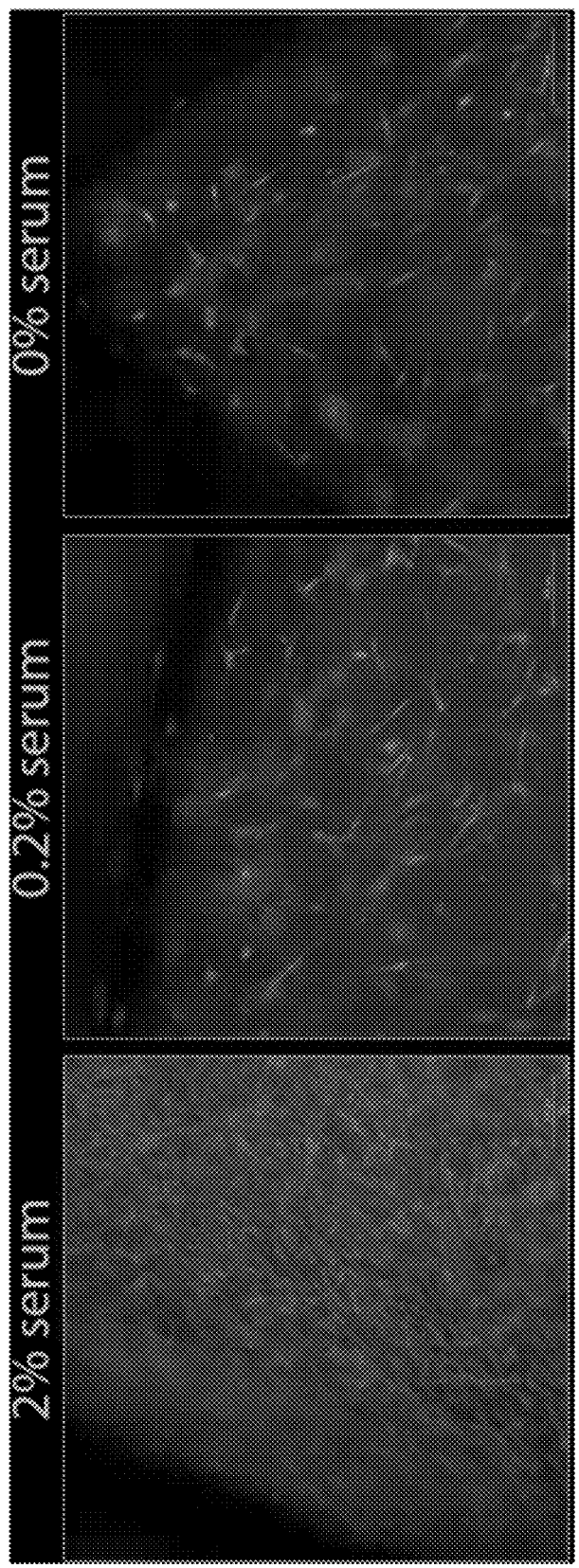
FIG. 41 depicts the effect of serum concentrations on cell viability and density.
Figure 42:
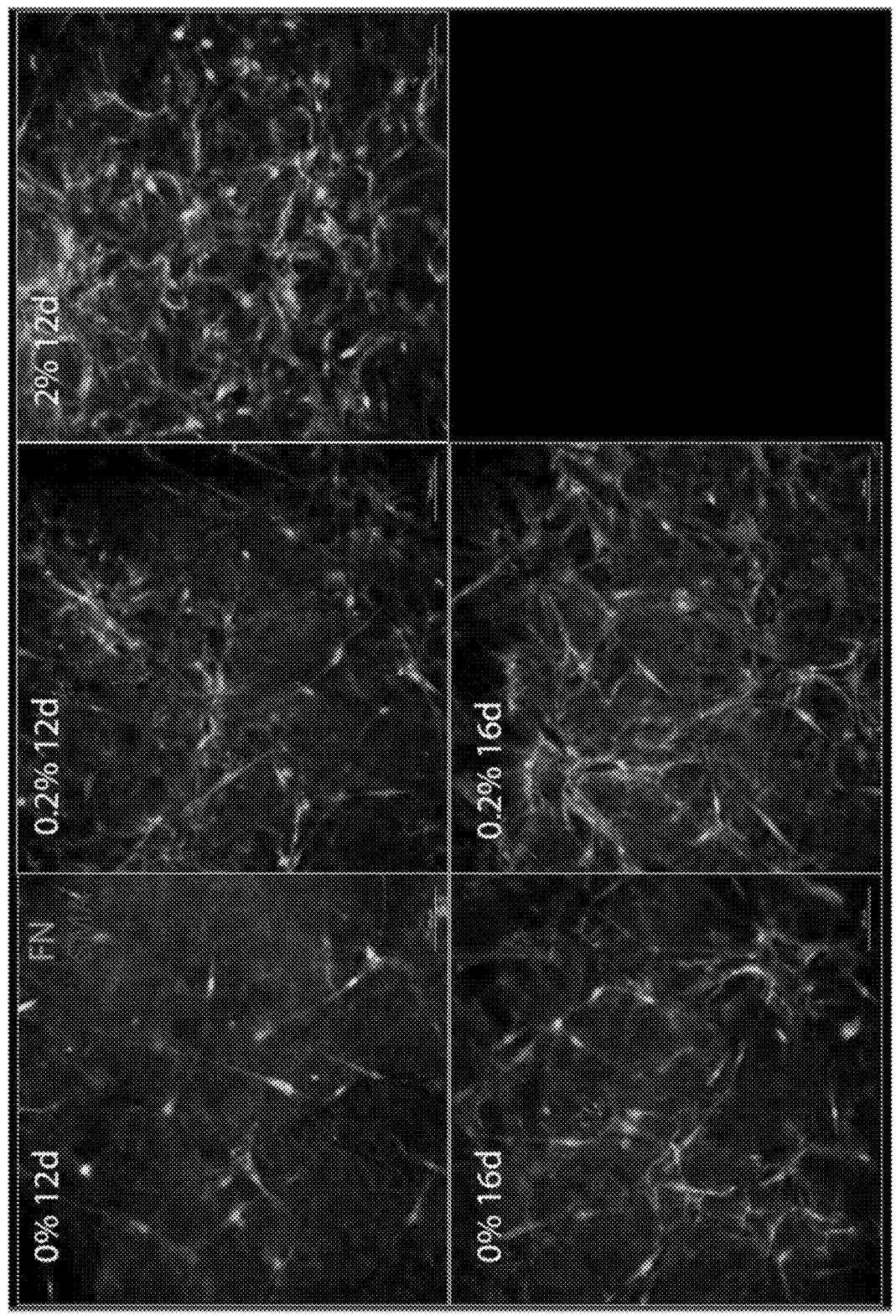
FIG. 42 depicts fibroblast proliferation induced by varying the serum concentration and culturing for 12 days or 16 days via staining of fibronectin (FN) and smooth muscle actin (SMA).
Figure 43:
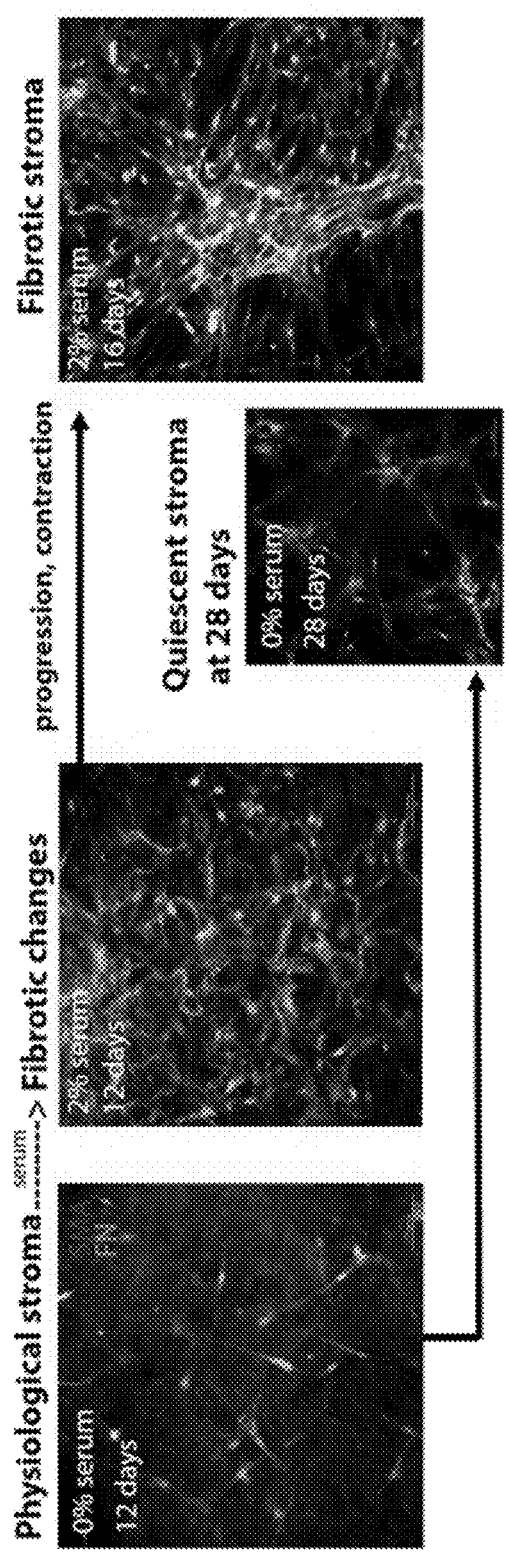
FIG. 43 depicts fibroblast proliferation induced by varying the serum concentration and culturing for 12, 16, or 28 days via staining of fibronectin (FN) and smooth muscle actin (SMA).
Figure 44:
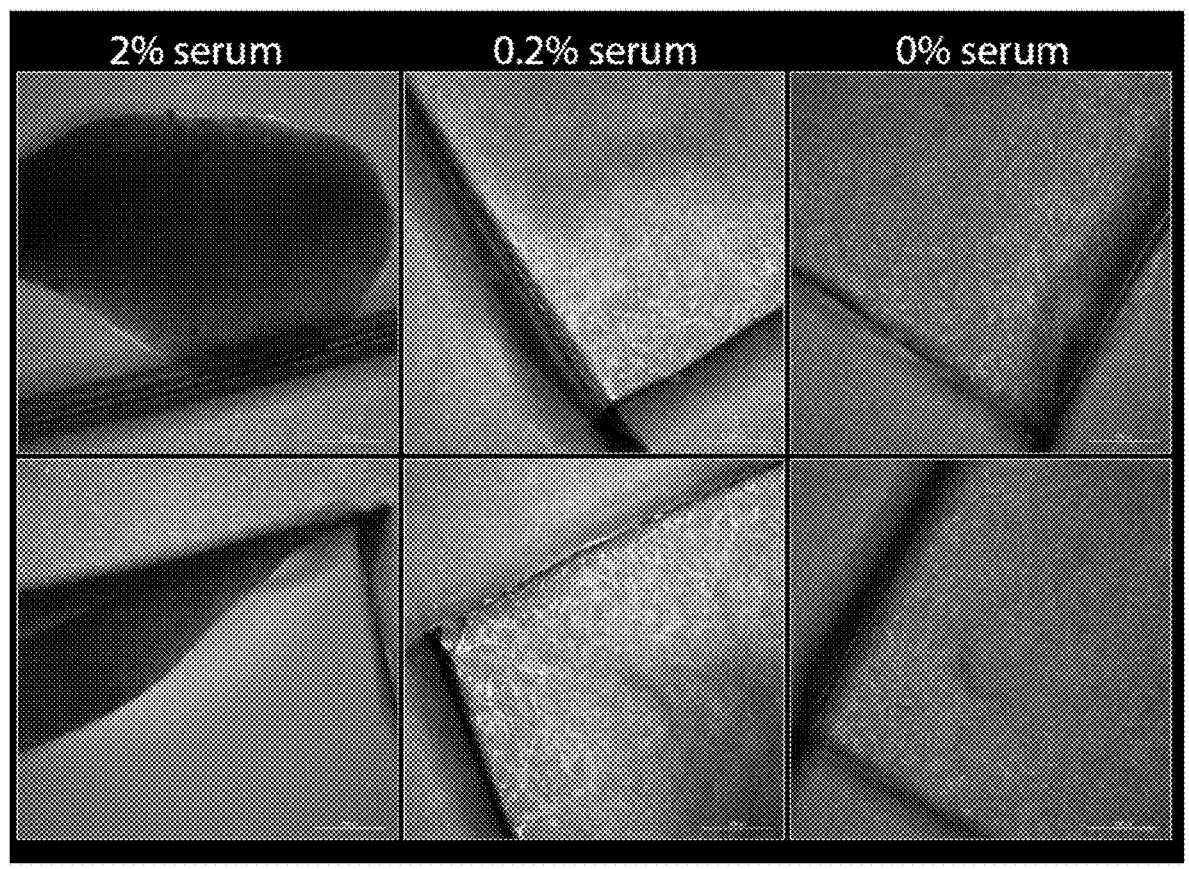
FIG. 44 depicts detachment of the gel layer from the chamber induced by varying the serum concentration and culturing for 16 days.
Figure 45:
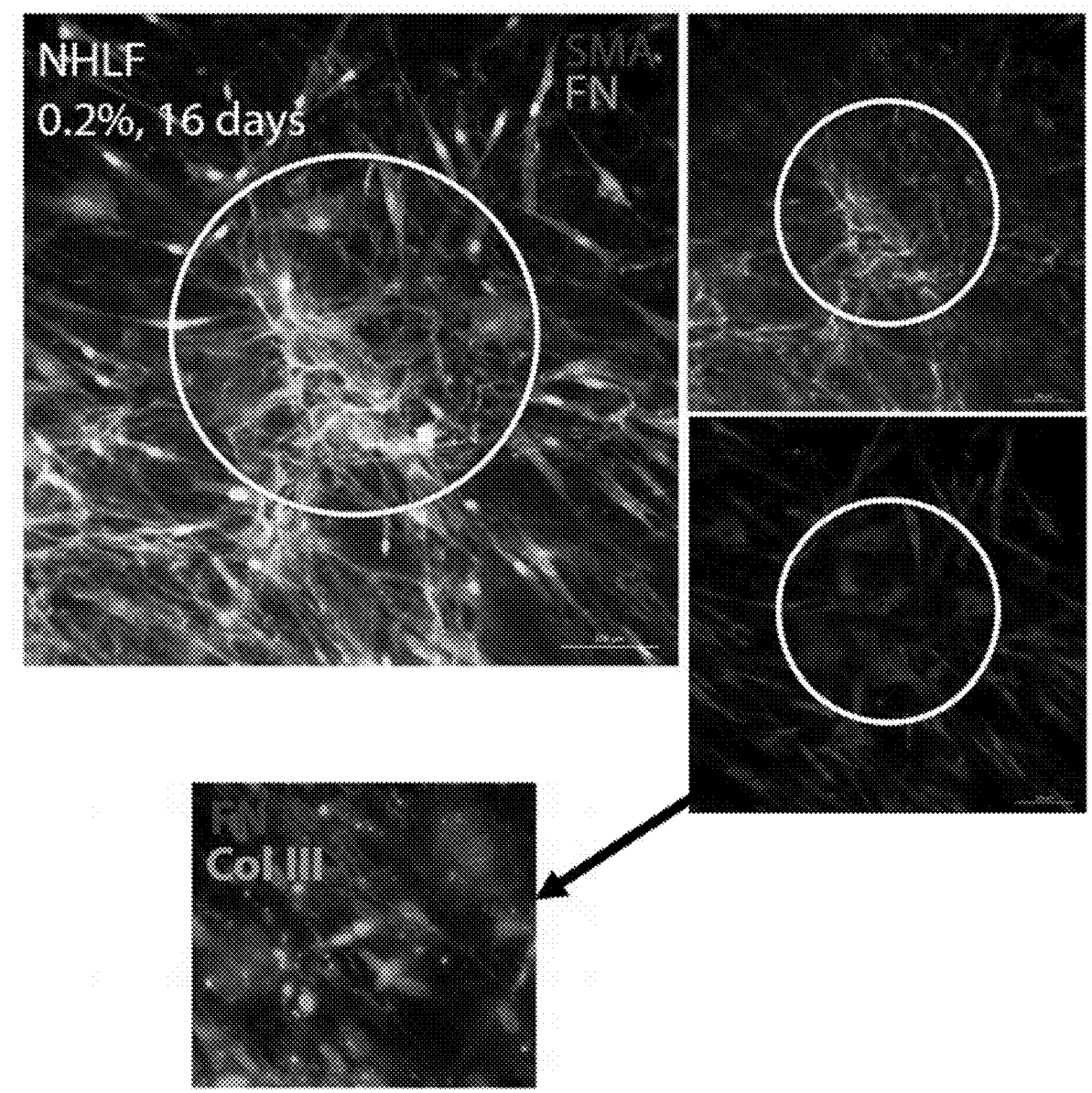
FIG. 45 depicts distinct stromal cell subsets and emergent fibrotic foci following culturing the gel layer in 0.2% serum for 16 days.

Fibrosis was induced by varying the serum concentration of the serum in the culture media. Incubating the gel layer containing the NHFL cells for 12 days in 2% serum lead to a fibrotic change as indicated by live/dead staining (FIG. 41) This was a marginal change. 2% serum lead to fibrotic cells, as the cells are very dense relatively and the gel has detached and begun to contract and fold over. By day 16, treatment with 0.2% serum lead to fibrotic changes and treatment with 2% serum lead to fibrotic stroma (FIGS. 42 and 43; stained for fibronectin (FN) and smooth muscle actin (SMA)). Changes with the 0.2% at day 16 were minor in comparison to 2% serum but more fibrotic than 0% serum. Detachment of the gel layer from the chamber was observed in most constructs cultured with 2% serum for 16 days (FIG. 44). Fibrotic foci-like structures with dense fibronectin matrix and collections of polygonal cells appeared in constructs cultured with 0.2% serum for 16 days (FIG. 45; stained for FN and SMA).

Figure 46:
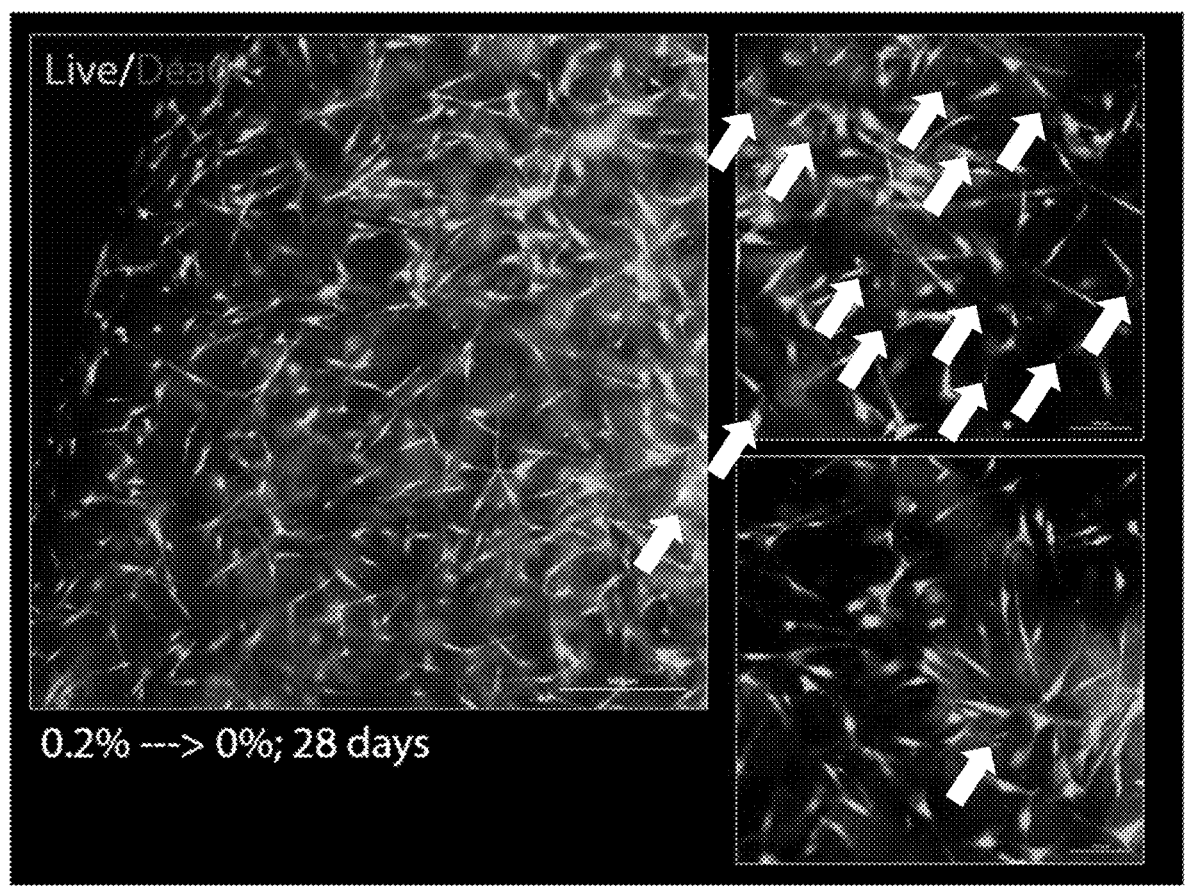
FIG. 46 depicts live/dead staining after long periods of culture. The arrows denote the few dead cells.

When the serum concentration was reduced from 0.2% to 0%, after 28 days the cells were quiescent and no contraction of the gel layer occurred (FIG. 46; arrows denote the few dead cells). Here, the cells were cultured in 0.2% in a 2D culture prior to use in the 3D model. The cells are normally grown in 2% serum but in this experiment they were cultured in 0.2% serum to slow down their rate of growth. They were placed in 0% serum concentration in the model, and they stay at 0% serum for up to 28 days as shown in FIG. with high viability. The live/dead staining in FIG. 46 demonstrated quiescence based on low cell density after a long period of culture.

The presence of glioblastoma-1 (Gli-1), a marker of myofibroblast cells, present in fibrotic lesions, indicated that this is a valid fibrosis model as activity of Gli-expressing cells is a relevant pathological feature of the in vivo disease (FIG. 47). In the gold standard model mouse bleomycin model depicted in FIG. 47, the staining pattern observed in the mouse model of lung fibrosis is similar to what is observed in the disclosed engineered human model.

Using different serum concentrations demonstrated the ability to measure increased in fibrotic outputs including cell proliferation, extracellular matrix ECM production, and changes in stromal cell shape in areas of intense ECM production. The 3D nature of the cell culture was important to modeling fibrosis.

Example 9: Five-Layer Injury Model

In this study, the development of the organ injury model was examined. A biomimetic lung model was fabricated as indicated in Example 7.

The serum concentration studies above in Example 8 is one example of tunable fibrosis in the model. In this study, we study an agent induced injury model. Injured epithelial cells release sonic hedgehog (SHH), so SHH was added exogenously to determine if a fibrotic response can be induced. The initial conditions (e.g., cell density, gel concentration, etc.) did not change from the previous examples (Examples 7 and 8). However, the agent used is different in Example 9 from Examples 7 and 8. For example, SHH was added at 500 ng/ml to produce the pro-fibrotic effect.

Figure 48:
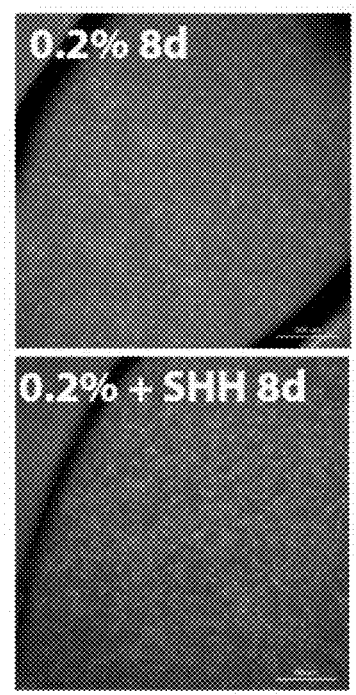
FIG. 48 depicts the use of a gel immobilization technique in connection with sonic hedgehog-driven (SHH) fibrosis, including sonic hedgehog, a pro-fibrotic signaling protein.

As demonstrated in FIG. 48, a fibrotic response can be induced by treating the cells with SHH.

Example 10: Regulation of the Fibrotic Pathway Using the Biomimetic Five-Layer Lune Fibrosis Model This example examined the regulation of the fibrotic pathway using inhibitors to reduce serum-induced fibrosis. In order to investigate this, PP2 and separately retinoic acid (RA) were added to the cell culture media. PP2 is a non-selective proto-oncogene tyrosine-protein kinase Src (SRC kinase) inhibitor. Src kinases transduce signals that control normal cellular processes such as cell proliferation, adhesion and motility. PP2 is known to promote a deactivated/quiescent state of cultured (myo)fibroblasts by inhibiting activation pathways. These kinases are found on integrin signaling complexes and have been shown to regulate integrin signals. Therefore, blocking SRC kinases effectively blocks integrin signaling intracelluarly without directly interfering with cell adhesion. Retinoic acid is involved in extracellular matrix biosynthesis.

A biomimetic lung model was fabricated as indicated in Example 7.

Figure 49:
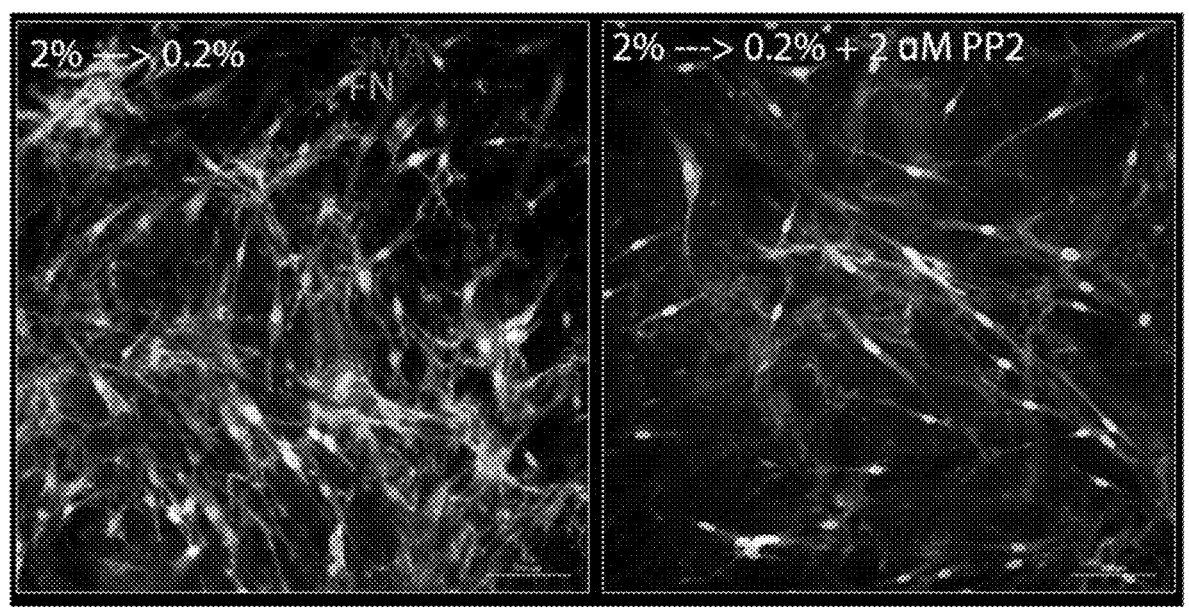
FIG. 49 depicts SRC kinase inhibition induced reduction in serum-induce fibrosis.

The cells for the PP2 study were cultured in 2D with 2% serum and then switched to 0.2% in the model. 2 µM of PP2 was added to the medium 24 hours after assembly of the model and maintained for the duration of the study. PP2 reduced fibrosis, demonstrating this could be used as a screening platform for inhibitors of fibrosis (FIG. 49). The initial conditions (e.g., cell density, gel concentration, etc.) did not change from the previous examples (Examples 7-9). However, the agent used is different in Example 10 from Examples 7-9.

Figure 50:
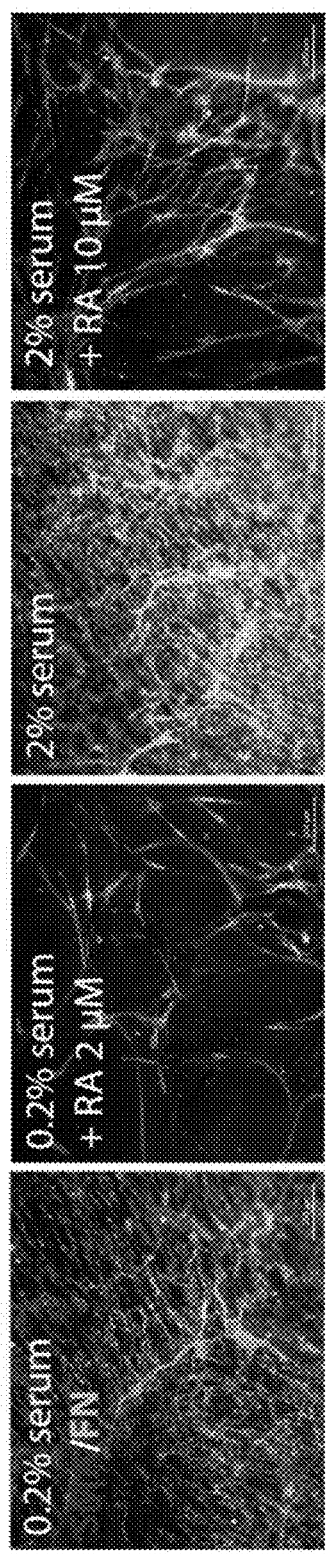
FIG. 50 depicts retinoic acid induced reduction in serum-induce fibrosis.

For retinoic acid treatment, the cells and densities were the same as indicated for FIG. 40 of Example 7. The cells were cultured in 0.2 or 2% serum with or without 2 µM RA (0.2% serum) or 10 µM RA (2% serum), following similar steps as the previous examples (e.g., Examples 7-9). FIG. 50 depicts the RA inhibited serum-induced fibrotic response.

Example 11: Modeling Injury Induced Fibrosis Using the Biomimetic Five-Layer Lung Fibrosis Model Typically organ fibrosis occurs secondarily to an organ injury. The biomimetic five-layer lung fibrosis model was used to examine injury induced fibrosis, including macrophage differentiation.

A biomimetic lung model was fabricated as indicated in Example 7, and the cells were plated and cultured as indicated for FIG. 40.

Figure 51:
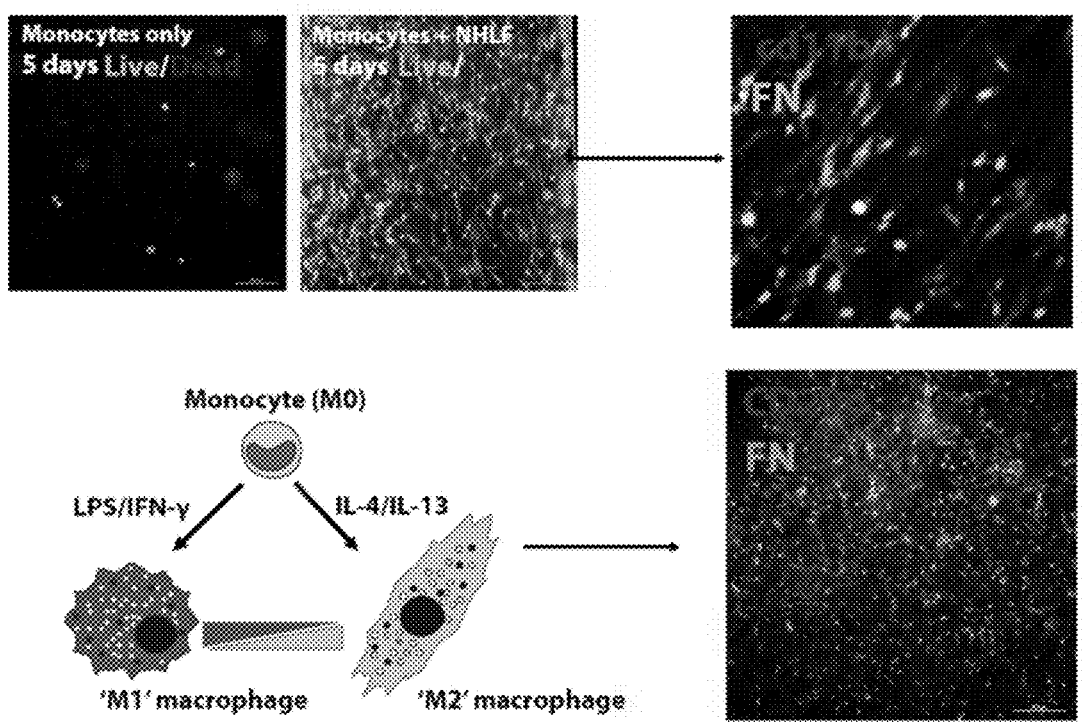
FIG. 51 depicts the presence of CD11b and CD206 in the stromal layer of the five-layer model.

In the absence of NHLF, monocytes did not proliferate and were not viable (FIG. 51). After the addition of NHLF and culturing for 7 days without serum, the cells began to differentiate and express CD11b (FIG. 51), which is an integrin complex that the cells use to adhere and migrate through the tissue. Under the same conditions, the cells also began to differentiate and express CD206 (FIG. 51), which is a marker of differentiated tissue macrophages.

Figure 52:
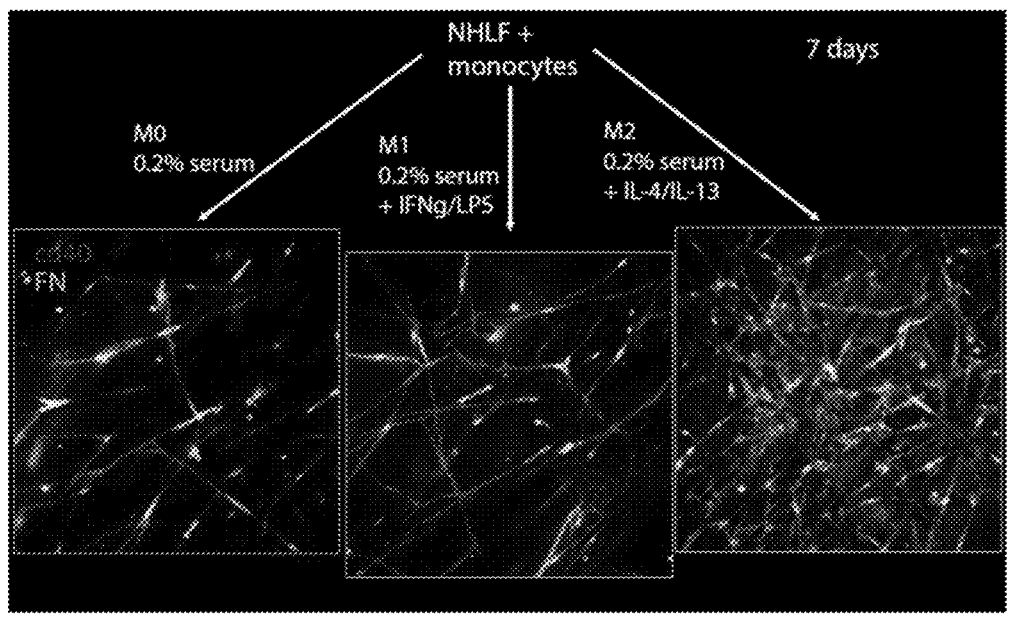
FIG. 52 depicts the effect of M2 microenvironment promotion of fibrosis.
Figure 53:
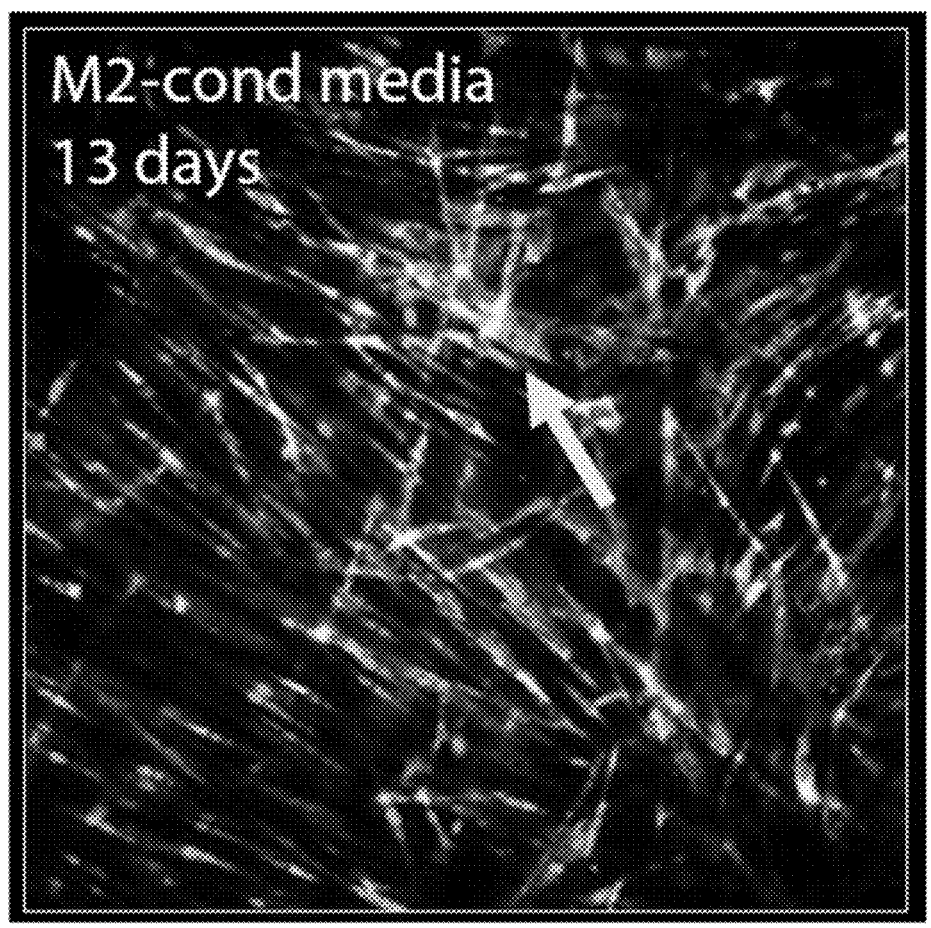
FIG. 53 depicts the presence of Gli-1 in the stromal layer of the five-layer model in M2 conditioned media.

M2 is a phenotype of tissue macrophages, and can be further elevated by IL-4 and produce high levels of IL-10, TGF-beta and low levels of IL-12. M2 macrophages are known to decrease inflammation, and would be present post tissue injury. Culturing the cells in the presence of M2-polarized macrophages promoted fibrosis in the microengineered stromal tissue gel layer, while M1-polarized macrophages did not (FIG. 52). Culturing the cells for 13 days in the M2 conditioned media (contains the natural mixture of factors secreted by M2 macrophases cells) induced the presence of Gli-1 marker of myofibroblast cells (FIG. 53). The arrow indicates a cluster of cells that co-express SMA and Gli-1 at high levels. These would be the cells that are found in fibrotic foci in vivo and serves as a validation of the model compared to what is known from organ fibrosis models in mice.

Example 12: Biomimetic Five-Layer Liver Fibrosis Model

The first and second channel slabs and the chamber slab of the model was formed using soft lithography techniques, in which the PDMF mixture was poured over the mold, and the slabs were allowed to cure. The microchannels were etched into each of the channel slabs, with the dimensions of 10 mm×1 mm×0.15 mm (length×width×height). The chamber was etched into the chamber slab, with the dimensions of 6 mm×3 mm×1 mm (length×width×height).

Figure 54:
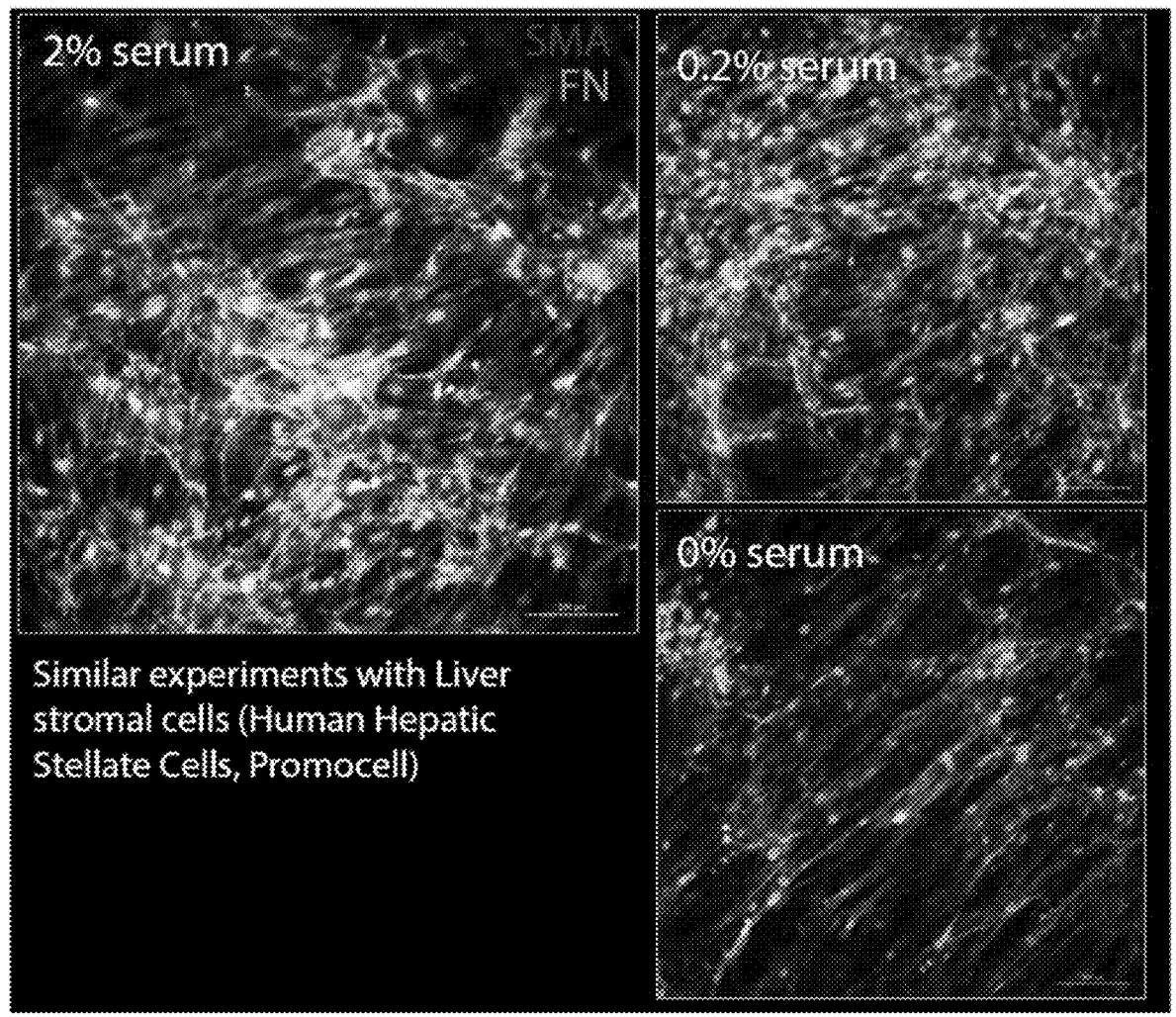
FIG. 54 depicts fibroblast proliferation in a five-layer liver model.

Increased levels of serum also induced fibrosis in the liver model (FIG. 53). FIG. 54 depicts fibroblast proliferation in a five-layer liver model.

The present disclosure is well adapted to attain the ends and advantages mentioned as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified and all such variations are considered within the scope and spirit of the present disclosure. Various publications, patents and patent application are cited herein, the contents of which are hereby incorporated by reference in their entireties.

REFERENCES

1. Jorgensen E et al., Cigarette smoke induces endoplasmic reticulum stress and the unfolded protein response in normal and malignant human lung cells. *BMC cancer* 8:229. (2008)
2. Kelsen et al., Cigarette smoke induces an unfolded protein response in the human lung: a proteomic approach. *American journal of respiratory cell and molecular biology* 38:541-550. (2008).
3. Kenche et al. Cigarette smoking affects oxidative protein folding in endoplasmic reticulum by modifying protein disulfide isomerase. *FASEB J* 27:965-977. (2013)

The invention claimed is:

1. A microengineered perfusable lumen sculpted from tissue comprising:
   a) a body having at least one microchannel, wherein walls of the at least one microchannel form a substrate for tissue growth; and
   b) a contractile tissue embedded in an extracellular matrix (ECM) gel layer adhered to each of three different walls of the microchannel, wherein the contractile tissue is not connected to a fourth wall of the microchannel, wherein the contractile tissue is shaped to create a semicircular opening within the microchannel, and wherein the semicircular opening extends through a length of the microchannel and forms a conduit.

2. The perfusable lumen of claim 1, wherein the substrate is poly-di-methyl-siloxane (PDMS).

3. The perfusable lumen of claim 1, wherein the ECM gel layer comprises extracellular matrix proteins, wherein the extracellular matrix proteins are selected from the group consisting of collagen, fibronectin, laminin, hyaluaronic acid, and mixtures thereof.

4. The perfusable lumen of claim 1, wherein the contractile tissue embedded within the ECM gel layer comprises fibroblasts.

5. The perfusable lumen of claim 1, wherein the contractile tissue embedded within the ECM gel layer comprises at least one of stromal tissue and stromal cells.

6. The perfusable lumen of claim 1, wherein the conduit is configured to be injected with the gel containing the contractile tissue, resulting in a tissue-to-tissue interface without using an intervening membrane.

\* \* \* \* \*